US012590130B2

(12) United States Patent
Tu et al.

(10) Patent No.: US 12,590,130 B2
(45) Date of Patent: Mar. 31, 2026

(54) BIPARTITE MOLECULES AND USES THEREOF IN TREATING DISEASES ASSOCIATED WITH ABNORMAL PROTEIN AGGREGATES

(71) Applicant: ACADEMIA SINICA, Taipei (TW)

(72) Inventors: Benjamin Pang-Hsien Tu, Taipei (TW); Rita Py Chen, Taipei (TW); Joseph Jen-Tse Huang, Taipei City (TW); Yijuang Chern, Taipei (TW); Yu-Song Jang, Kaohsiung City (TW); Xiang-Me Lai, Chiayi County (TW); Tai-Yan Liao, Tainan City (TW); Te-Hsien Kung, New Taipei City (TW)

(73) Assignee: Academia Sinica, Taipei (TW)

( * ) Notice: Subject to any disclaimer, the term of this patent is extended or adjusted under 35 U.S.C. 154(b) by 1443 days.

(21) Appl. No.: 17/105,858

(22) Filed: Nov. 27, 2020

(65) Prior Publication Data

US 2021/0198332 A1    Jul. 1, 2021

Related U.S. Application Data

(62) Division of application No. 15/328,593, filed as application No. PCT/US2015/041921 on Jul. 24, 2015, now Pat. No. 10,882,890.

(60) Provisional application No. 62/029,030, filed on Jul. 25, 2014.

(51) Int. Cl.
C07K 14/47    (2006.01)
A61K 38/00    (2006.01)

(52) U.S. Cl.
CPC ...... *C07K 14/4711* (2013.01); *C07K 14/4703* (2013.01); *A61K 38/00* (2013.01); *C07K 2319/00* (2013.01)

(58) Field of Classification Search
CPC ............ C07K 14/4711; C07K 14/4703; C07K 2319/00; A61K 38/00
See application file for complete search history.

(56) References Cited

U.S. PATENT DOCUMENTS

| | | |
|---|---|---|
| 6,632,616 B2 | 10/2003 | Burke et al. |
| 7,569,547 B2 | 8/2009 | Lindberg et al. |
| 8,003,612 B2 | 8/2011 | Lake et al. |
| 2005/0026165 A1 | 2/2005 | Orser et al. |
| 2006/0079447 A1 | 4/2006 | Wetzel |
| 2008/0031954 A1 | 2/2008 | Paris et al. |
| 2010/0047826 A1 | 2/2010 | Nonaka et al. |
| 2011/0182920 A2 | 7/2011 | Ugurbil et al. |
| 2012/0122790 A1 | 5/2012 | Drezner et al. |

FOREIGN PATENT DOCUMENTS

| | | |
|---|---|---|
| EP | 1676588 A1 | 7/2006 |
| WO | 9965516 A1 | 12/1999 |

OTHER PUBLICATIONS

Burke Ka et al., The interaction of polyglutamine peptides with lipid membranes is regulated by flanking sequences associated with Huntingtin. May 2013, J. Biol. Chem. 288(21), 14993-15005.

Chang Esh et al, A new amyloid-like beta-aggregate with ammyloid characteristics, except fibril morphology. J. Mol. Biol. 2009, 385, 1257-1265.

Darnell GD et al., Mechanism of Cis-inhibition of PolyQ fibrillation of PolyP: PPII oligomers and the hydrophobic effect. Biophysical J, 2009, 97, 2295-2305.

Didenko VV et al., Polyethyleneimine as a transmembrane carrier of fluorescently labeled proteins and antibodies. Anal. Biochem. 2005, 344(2), 168-173.

El-Agnaf et al., A strategy for designing inhibitors of alpha-synuclein aggregation and toxicity as a novel treatment for Parkinson's disease and related disorders. FASEB J. Aug. 2004; 18(11):1315-7. Epub Jun. 4, 2004.

Fuchs SM et al., Polyarginine as a multifunctional fusion tag. Protein Sci. 2005, 14, 1538-1544.

Funke et al., Peptides for therapy and diagnosis of Alzheimer's disease. Curr Pharm Des. 2012; 18(6):755-67.

Futaki S et al, Arginine-rich peptides. J. Biol. Chem, 276(8):5836-5840, 2001.

Futami J et al, Exploiting protein cationization techniques in future drug development. Expert Opinion Drug Discovery, 2(2): 261-269, 2007.

George RA and Heringa J, An analysis of protein domain linkers: their classification and role in protein folding. Protein Engineering, 2003, 15(11), 871-879.

Ghanta J et al., A strategy for designing inhibitors of beta-amyloid toxicity. J Biol Chem, 1996, 271(47), 29525-29528.

Gulyaeva NV and Sepanichev MY, Abeta(25-35) as proxyholder for amyloidogenic peptides: In vivo evidence. Exp. Neurol. 222:6-9, 2010.

Hughes et al., Inhibition of toxicity in the beta-amyloid peptide fragment beta-(25-35) using N-methylated derivatives. J. Biol. Chem. 275(33):25109-15, 2000.

Kahlem P et al., Peptides containing glutamine repeats as substrates for transglutaminase-catalyzed cross-linking: Relevance to diseases of the nervous system. Proc. Natl Acad. Sci. USA, 93, 14580-14585, 1996.

Lakhani VV et al., Polyglutamine induced misfolding of Huntingtin Exon1 is modulated by the flanking sequences. PLoS Copmput. Biol. 6(4):e1000772, 2010.

Lin CY et al, Intranasal administration of polyethylenimine-conjugated scavenger peptide reduces amyloid-beta accumulation in a mouse model of Alzheimer's disease. J. Alzheimer's Disease, 2016, 53, 1053-1067.

(Continued)

*Primary Examiner* — Kimberly Ballard
(74) *Attorney, Agent, or Firm* — Prosyla Group, PC

(57) ABSTRACT

Bipartite molecules comprising a peptide affinity moiety and at least one charged moiety and uses thereof in reducing formation of abnormal protein aggregate and treating diseases associated with such abnormal protein aggregate, including neurodegenerative disease characterized by formation of protein aggregates.

6 Claims, 38 Drawing Sheets

Specification includes a Sequence Listing.

(56) References Cited

OTHER PUBLICATIONS

Martin et al., Effect of the Alzheimer amyloid fragment Abeta(25-35) on Akt/PKB kinase and survival of PC12 cells. J. Neurochem. Sep. 2001;78(5):1000-8.

Mason et al., Design strategies for anti-amyloid agents. Curr Opin Struct Biol. 2003;13:1-7.

Millucci et al., Rapid aggregation and assembly in aquenos solution of A beta (25-35) peptide. J Biosci. Jun. 2009;34 (2):293-303.

Mitchell et al., Polyarginine enters cells more efficiently than other polycationic homopolymers. J. Peptide Rs. 56:318-325, 2000.

Nagarajan A et al., The effects of flanking sequences in the interaction of polyglutamine peptides with a membrane bilayer. J. Phys. Chem. B, 2014, 118, 6368-6379.

Pallitto et al., Recognition sequence design for peptidyl modulators of beta-amyloid aggregation and toxicity. Biochemistry. Mar. 23, 1999;38(12):3570-8.

Ren et al., Amino acid sequence requirements of peptides that inhibit polyglutamine-protein aggregation and cell death. Biochem Biophys Res Commun. Nov. 2, 2001;288(3):703-10.

Sun X et al., Hybrid peptides attenuate cytotoxicity of beta-amyloid by inhibiting its oliogomerization: implication from solvent effects. Peptides, 30:1282-87, 2009.

Tsai et al., The role of heat shock protein 70 in the protective effect of TC-1 on beta-amyloid-induced toxicity in differentiated PC12 cells. PLoS One. Jul. 26, 2013;8(7):e69320. doi: 10.1371/journal. pone.0069320. Print 2013.

Walters RH et al., Aggregation kinetics of interrupted polyglutamine peptides. J. Mol. Biol. 2011, 412, 505-519.

8R

PolyQ

D

E

J

K

D

☐ APP/PS1 + PEI     ▉ APP/PS1 + R$_8$-Aβ(25-35)-PEI

E

☐ APP/PS1 + PEI     ▉ APP/PS1 + R$_8$-Aβ(25-35)-PEI

Cortex

A. Cortex

B. Hippocampus

C. Cortex

D. Hippocampus

A    Figure 19
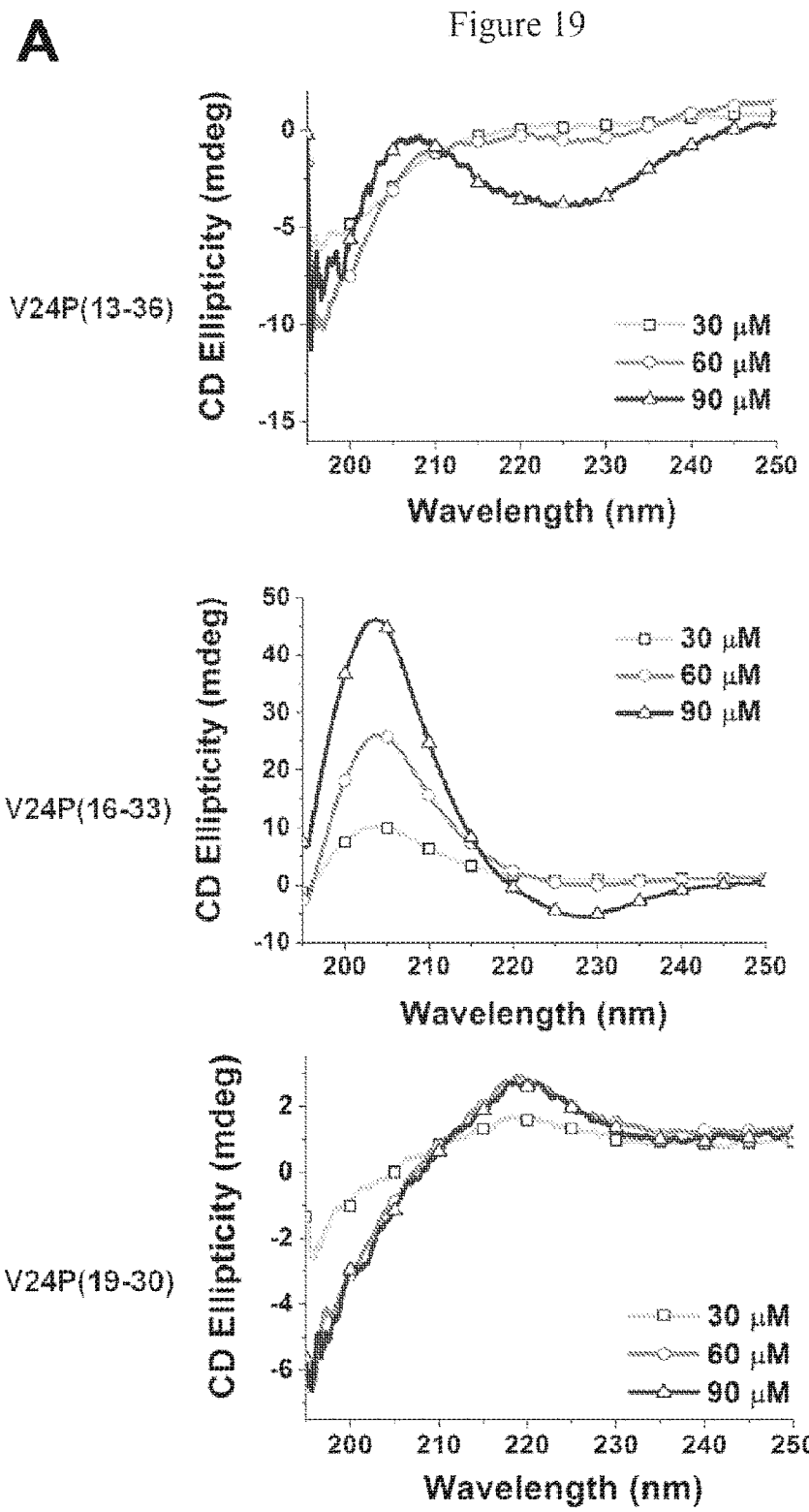

(A)

(B)

BIPARTITE MOLECULES AND USES THEREOF IN TREATING DISEASES ASSOCIATED WITH ABNORMAL PROTEIN AGGREGATES

CROSS REFERENCE TO RELATED APPLICATION

This application is a divisional of U.S. patent application Ser. No. 15/328,593, filed Jan. 24, 2017, which is a 371 National Phase of International Application No. PCT/US2015/041921, filed Jul. 24, 2015, which claims the benefit of U.S. Provisional Application No. 62/029,030, filed Jul. 25, 2014, under 35 U.S.C. § 119 the contents of which are incorporated by reference in their entirety.

BACKGROUND OF THE INVENTION

Neurodegenerative diseases, such as Alzheimer's disease (AD), Huntington's disease (HD), synucleinopathy (e.g., Parkinson's disease (PD) and dementia with Lewy bodies (DLB)), tauopathy (e.g., Pick's disease, progressive supranuclear palsy, corticobasal degeneration, and frontotemporal dementia with Parkinsonism linked to chromosome 17), TDP-43 proteinopathy (e.g., amyotrophic lateral sclerosis (ALS) and frontotemporal lobar degeneration with ubiquitinated inclusions (FTLD-U)), and Creutzfeldt-Jacob disease (CJD), are characterized by an abnormal aggregation of pathogenic proteins, leading to the formation of inclusion bodies (IBs). Recently, the prion-like behavior of abnormal protein aggregates has been established, showing that these IBs not only serve as a diagnostic pathological marker, but also play an important role in the pathogenesis of these diseases.

Because neurodegenerative diseases are usually age-related, they primarily affect patients in mid- to late-life. It is expected that their incidence will increase as the population ages. Since the processes of many neurodegenerative diseases are not well-understood, there is currently no cure for these diseases. It is therefore of great importance to develop effective therapies for neurodegenerative diseases.

SUMMARY OF THE INVENTION

The present disclosure is based, at least in part, on the unexpected discovery that a number of bipartite molecules, e.g., polyR-AB40-(25-35), PEI-V24P (10-40), and polyR-polyQ, successfully decreased abnormal protein aggregation and demonstrated beneficial therapeutic effects in murine models of Huntington's disease and Alzheimer's disease (APP/PS1). More specifically, polyR-polyQ was found to bind mutant huntingtin (mHtt) protein aggregates, decrease mHtt-mediated toxicity, and delay the onset and progress of neurologic dysfunctions observed in the R6/2 murine model of Huntington's disease. Furthermore, polyR-Aβ40 (25-35) and PEI-V24P (10-40) were found to ameliorate $A\beta_{40}$ cytotoxicity in mouse neuroblastoma cells, prevent memory deterioration, and decrease the level of Aβ plaque in the brains of the APP/PS1 transgenic murine model of Alzheimer's disease. The bipartite molecules described herein all contain an affinity moiety (e.g., the polyQ portion, the Aβ40 (25-35) portion, and the V24P (10-40) portion) capable of binding to an abnormal protein aggregate or a component thereof (e.g., a monomer of the aggregate) and a charged moiety (e.g., the polyR portion or the PEI portion).

Accordingly, one aspect of the present disclosure relates to a bipartite molecule comprising (i) a peptide affinity moiety that binds to a disease-associated abnormal protein aggregate, or component thereof; and (ii) at least one charged moiety. The affinity moiety is linked (e.g., covalently) to the at least one charged moiety. In some examples, the bipartite molecule described herein may contain one charged moiety (e.g., a charged peptide fragment), which may be conjugated to either the N-terminus or the C-terminus of the peptide affinity moiety. In other examples, the bipartite molecule described herein may contain two charged moieties (e.g., the same or different), one being conjugated to the N-terminus of the peptide affinity moiety and the other being conjugated to the C-terminus of the peptide affinity moiety.

In some embodiments, the peptide affinity moiety binds an abnormal protein aggregate or a component thereof that is associated with a neurodegenerative disease (e.g., Alzheimer's disease, Huntington's disease, synucleinopathy (e.g., Parkinson's disease, and dementia with Lewy bodies), tauopathy (e.g., Pick's disease, progressive supranuclear palsy, corticobasal degeneration, and frontotemporal dementia with Parkinsonism linked to chromosome 17), TDP-43 proteinopathy (e.g., amyotrophic lateral sclerosis (ALS), frontotemporal lobar degeneration-TDP-43 proteinopathy, frontotemporal lobar degeneration-tauopathy, Pick's disease, cortical basal degeneration, progressive supranuclear palsy, FTDP-17 with ubiquitinated inclusions (FTLD-U)), or Creutzfeldt-Jacob disease.

In some examples, the peptide moiety of the bipartite molecule is a fragment of amyloid β or TDP-43, which can interfere with amyloid β or TDP protein aggregation. The fragment of amyloid β may comprise the amino acid sequence of GSNKGAIIGLM (SEQ ID NO: 1) or YEVHHQKLVFFAED$^D$PGSNKGAIIGLMVGGVV (SEQ ID NO: 2) (PP refers to the D-form of proline), which is capable of interfering with amyloid β protein aggregation.

In other examples, the peptide affinity moiety of the bipartite molecule described herein can be a polyglutamine (PolyQ) fragment (containing, e.g., 5-20 Q residues such as 10 Q or 15 Q residues), which is capable of binding to the polyQ stretch of huntingtin protein, thereby preventing the formation of abnormal protein aggregates.

In any of the bipartite molecules described herein, the at least one charged moiety of the bipartite molecule can be a polyarginine (PolyR) fragment (containing, e.g., at least 5, 8, 10, or 12 R residues) or polyethylenimine (PEI). In some embodiments, the bipartite molecules may contain more than 2 charged moieties (e.g., 2, 3, or more). Examples of the bipartite molecules as described herein include, but are not limited to:

RRRRRRRRGSNKGAIIGLM (SEQ ID NO: 3),
YEVHHQKLVFFAED$^D$PGSNKGAIIGLMVGGVV-PEI (SEQ ID NO: 5),
RRRRRRRRWDQQQQQQQQQQ (SEQ ID NO: 6),
RRRRRRRRWDQQQQQQQQQQQQQQQQ (SEQ ID NO: 7), or
RRRRRRRRGSNKGAIIGLM-PEI (SEQ ID NO: 4).

In another aspect, the present disclosure provides a pharmaceutical composition comprising one or more bipartite molecules as described herein and a pharmaceutically acceptable carrier.

In yet another aspect, the present disclosure provides a method for reducing the formation of an abnormal protein aggregate associated with a disease (e.g., a neurodegenerative disease) or treating such a disease, the method comprising administering (e.g., via an intranasal route) to a subject in need of the treatment an effective amount of one or more bipartite molecules as described herein. In some examples, the subject is a human patient having, suspected of having, or at risk for, a neurodegenerative disease, e.g., Alzheimer's disease, Huntington's disease, Parkinson's disease, dementia with Lewy bodies, amyotrophic lateral sclerosis, frontotemporal lobar degeneration-TDP-43 proteinopathy, frontotemporal lobar degeneration-tauopathy, Pick's disease, cortical basal degeneration, progressive supranuclear palsy, FTDP-17, and/or Creutzfeldt-Jacob disease.

In some examples, the neurodegenerative disease is Alzheimer's disease (AD) and the bipartite molecule for use in treating AD comprises an affinity moiety having the amino acid sequence GSNKGAIIGLM (SEQ ID NO: 1) or YEVHHQKLVFFAED$^P$PPGSNKGAIIGLMVGGVV (SEQ ID NO: 2). Such a bipartite molecule can be RRRRRRRRGSNKGAIIGLM (SEQ ID NO: 3), RRRRRRRRGSNKGAIIGLM-PEI (SEQ ID NO: 4), or YEVHHQKLVFFAED$^P$PGSNKGAIIGLMVGGVV-PEI (SEQ ID NO: 5).

In another example, the neurodegenerative disease is Huntington's disease and the bipartite molecule for use in treating this disease comprise an affinity moiety having a PolyQ fragment. Such a bipartite molecule can be RRRRRRRRWDQQQQQQQQQQQ (SEQ ID NO: 6), or RRRRRRRRWDQQQQQQQQQQQQQQQQ (SEQ ID NO: 7).

Also within the scope of the present disclosure are (a) pharmaceutical compositions for use in interfering with abnormal protein aggregation associated with a disease (e.g., preventing the formation of, or disrupting existing, aggregates) or treating such a disease, the pharmaceutical composition comprising a pharmaceutically acceptable carrier and one or more bipartite molecule as described herein; and (b) uses of any of the pharmaceutical compositions or bipartite molecules for manufacturing a medicament for treating a disease associated with abnormal protein aggregation. Such a disease can be a neurodegenerative diseases characterized by abnormal protein, including, but not limited to, Alzheimer's disease, Huntington's disease, Parkinson's disease, dementia with Lewy bodies, amyotrophic lateral sclerosis, frontotemporal lobar degeneration-TDP-43 proteinopathy, frontotemporal lobar degeneration-tauopathy, Pick's disease, cortical basal degeneration, progressive supranuclear palsy, FTDP-17, and/or Creutzfeldt-Jacob disease.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

FIG. 16. MicroPET amyloid images of 12 month-old wild type (WT) control mice and transgenic (Tg) mice treated with PEI or $R_8$-Aβ(25-35)-PEI peptide for 8 months. Panel A: Representative PET images of the Tg mouse brains co-registered with a mouse T2-weighted MRI brain template. As shown, the brain of the PEI-treated Tg mouse had much higher amyloid signals at the cortex (CT), hippocampus (HP), and amygdala (AMY) compared with that of the WT mouse. $R_8$-Aβ(25-35)-PEI peptide treatment reduced the amyloid signal of the Tg mouse. Panel B: Quantitation of the signal of $^{11}C$-labeled Pittsburgh compound B (PIB) in regions as indicated. N=6 per group, $<0.001$; $*<0.0005$, statistics were conducted with the Student's t test.

7

Electron microscopy images of 60 µM V24P(1-28) and V24P(10-40) after incubation at 25° C. for about 1 month.

Figure 19:
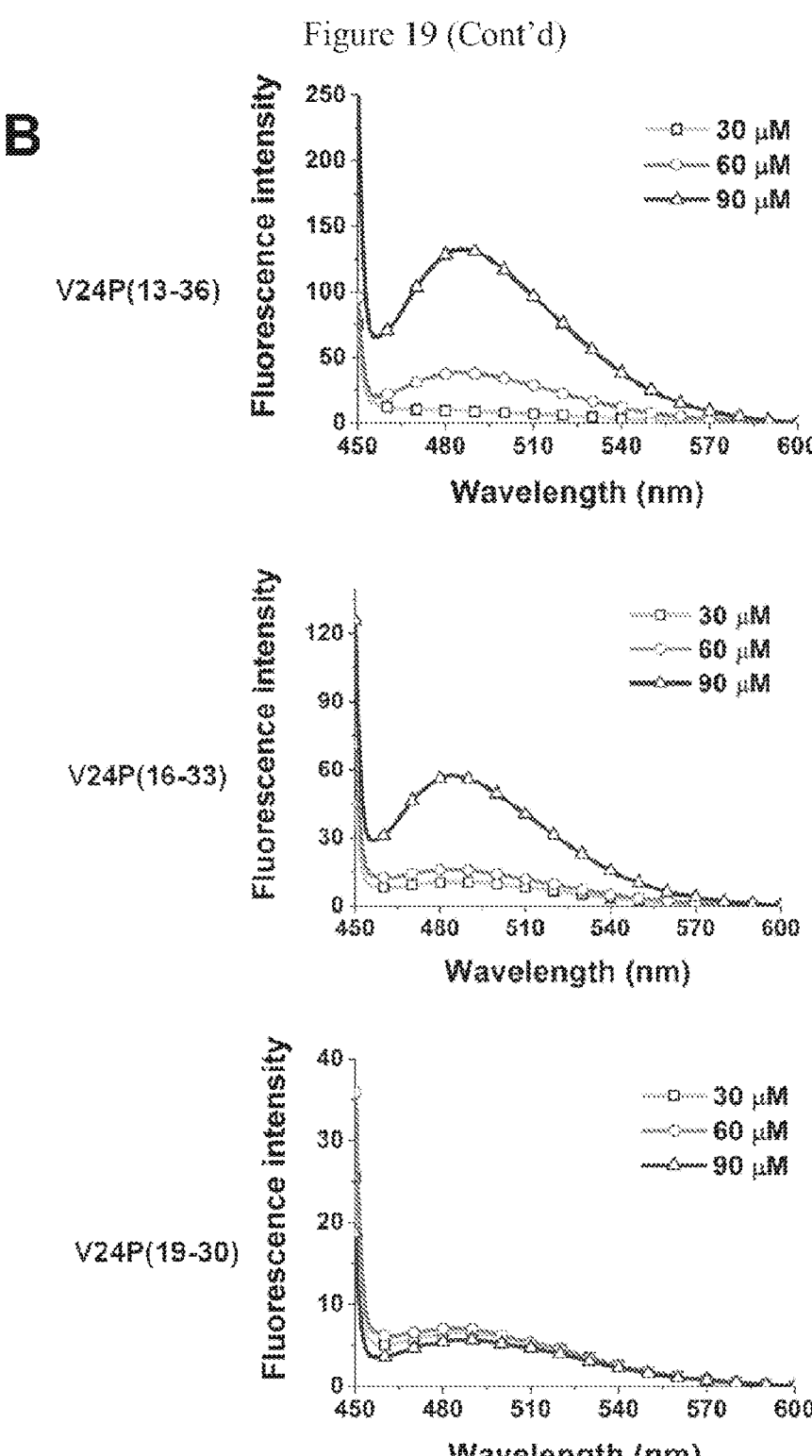

FIG. 19. Structural studies on V24P(13-36), V24P(16-33), and V24P(19-30). The peptides were dissolved at concentrations of 30, 60, or 90 µM and their CD spectra (panel A) and fluorescence spectra after binding ThT (panel B) were immediately recorded.

Figure 20:
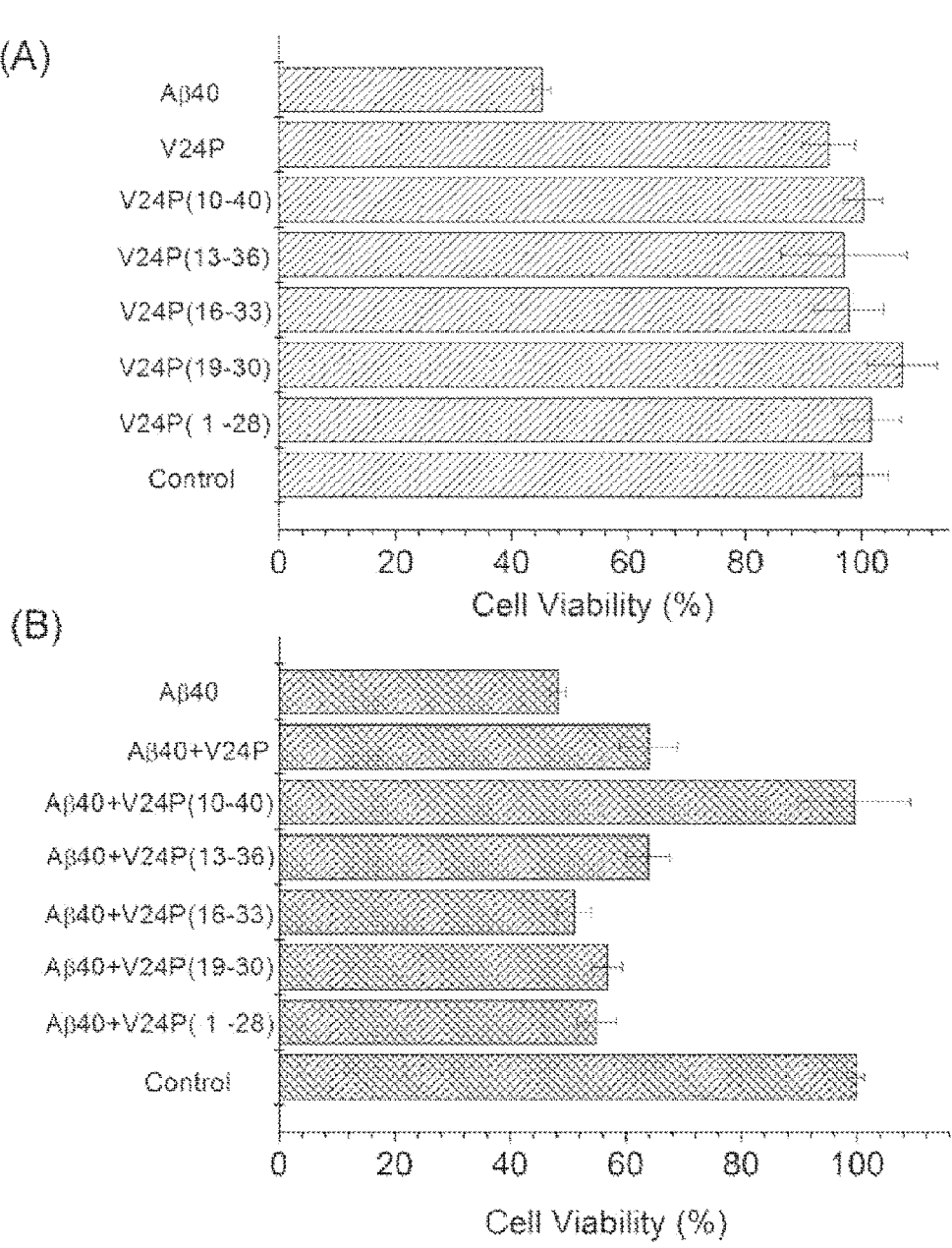

FIG. 20. Cell viability assay. The viability of mouse N2a cells incubated with the indicated peptide(s) was measured using the MTT assay. Panel A: Comparison of the viability of Aβ40 and the designed peptides containing the V24→$^D$P mutation. Panel B: Comparison of the viability of 30 µM Aβ$_{40}$ alone or together with 30 µM designed peptide. The standard deviations are shown as bars (compared with Aβ40, p<0.01 for all the other data by Student's t test). A: Cortex. B: Hippocampus.

Figure 21:
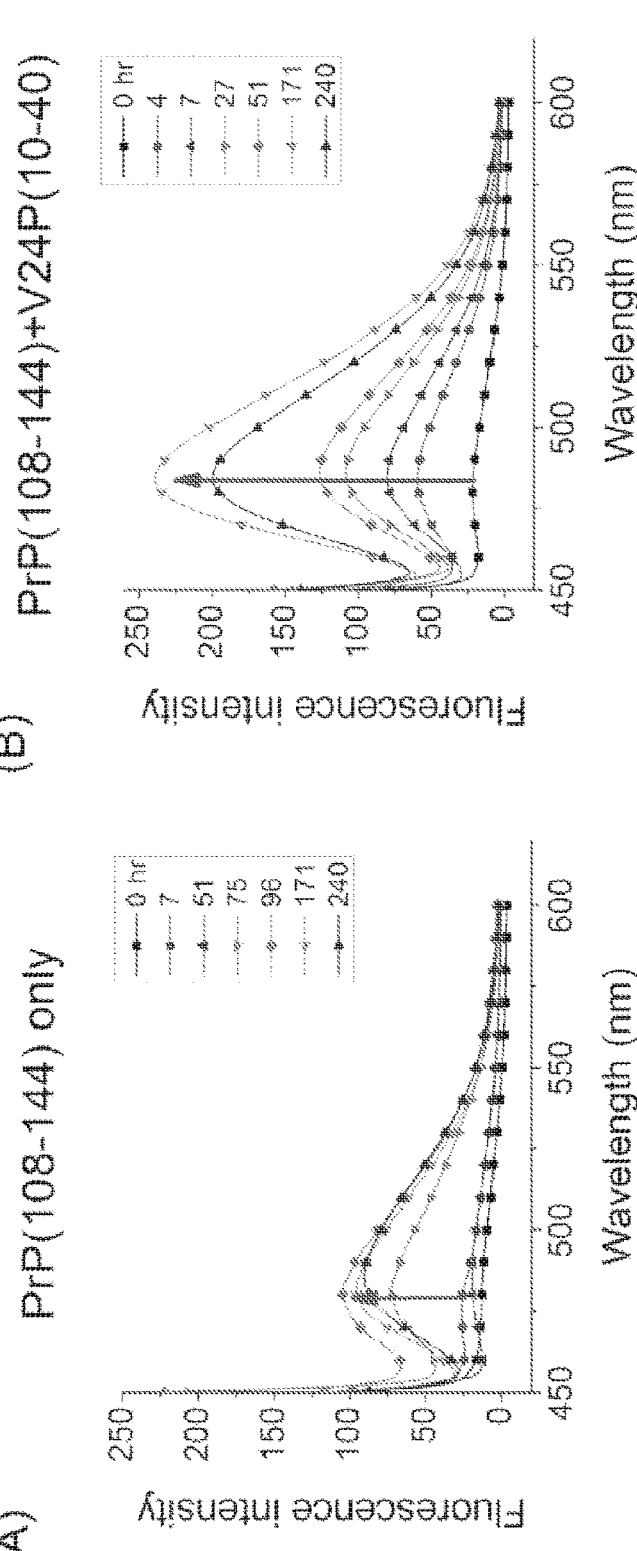

FIG. 21. Amyloid formation of hamster prion peptide PrP(108-144) in the absence (panel A) or presence of V24P(10-40) (panel B). Solutions of 50 µM PrP(108-144) with (panel B) or without (panel A) 50 µM V24P(10-40) were incubated in 20 mM NaOAc, pH 3.7/140 mM NaCl, at room temperature for different times. Samples were then removed and amyloid formation was measured using the ThT binding assay.

Figure 22:
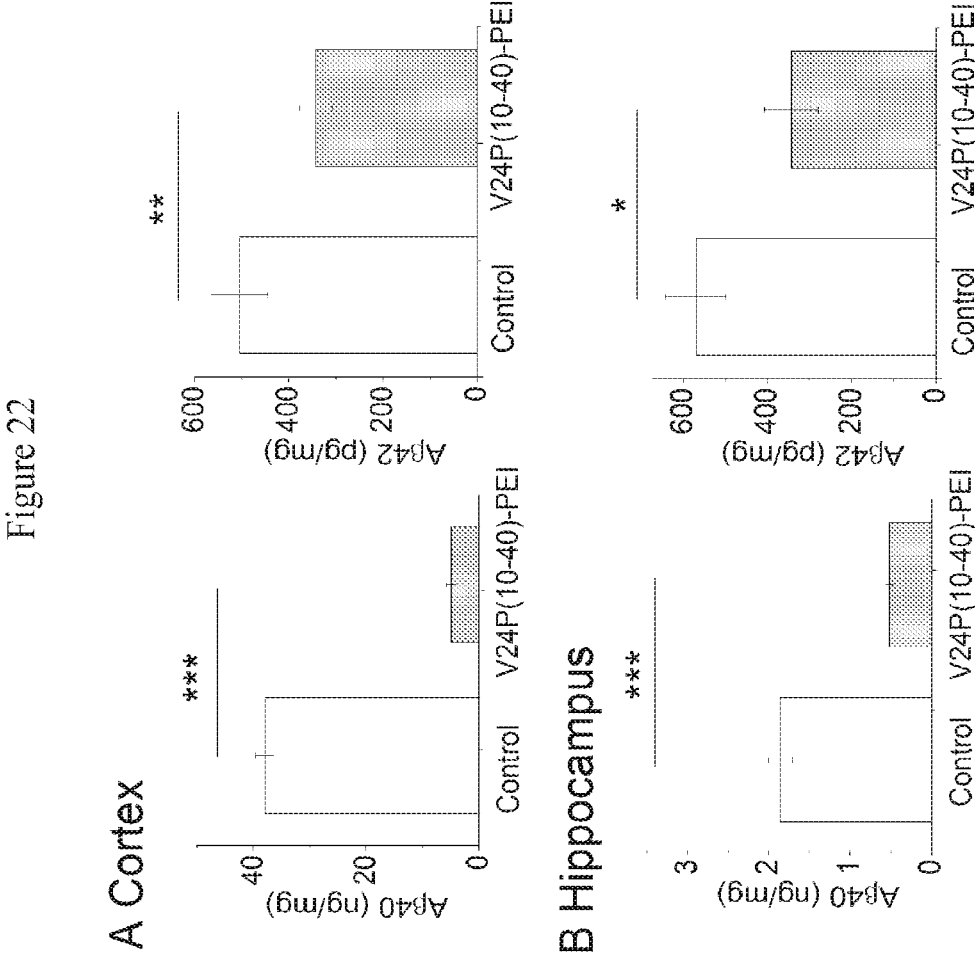

FIG. 22. Effect of V24P(10-40)-PEI on Aβ peptide levels. APP/PS1 mice were treated from the age of 4 months to 8 months with PEI (control) or V24P(10-40)-PEI as described in the Examples. The levels of Aβ40 and Aβ42 levels in the hippocampus and cortex were measured by ELISA. The data were presented as the mean±standard deviation for 3 mice per group (*p<0.05; p<0.01; *p<0.001, Student's t test).

Figure 23:
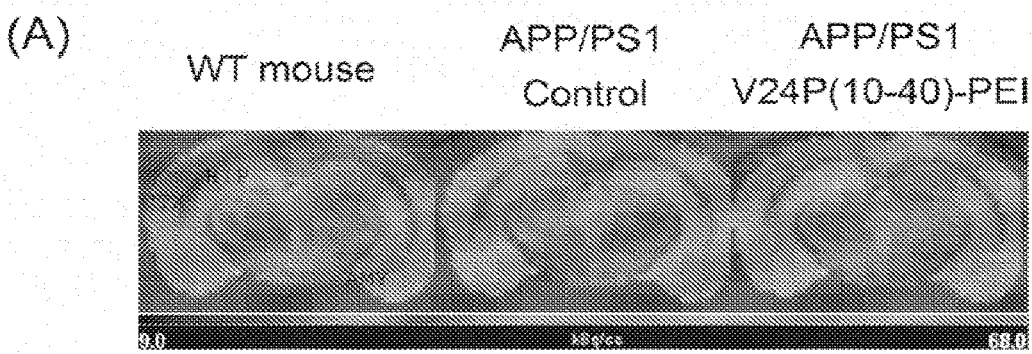
Figure 23:
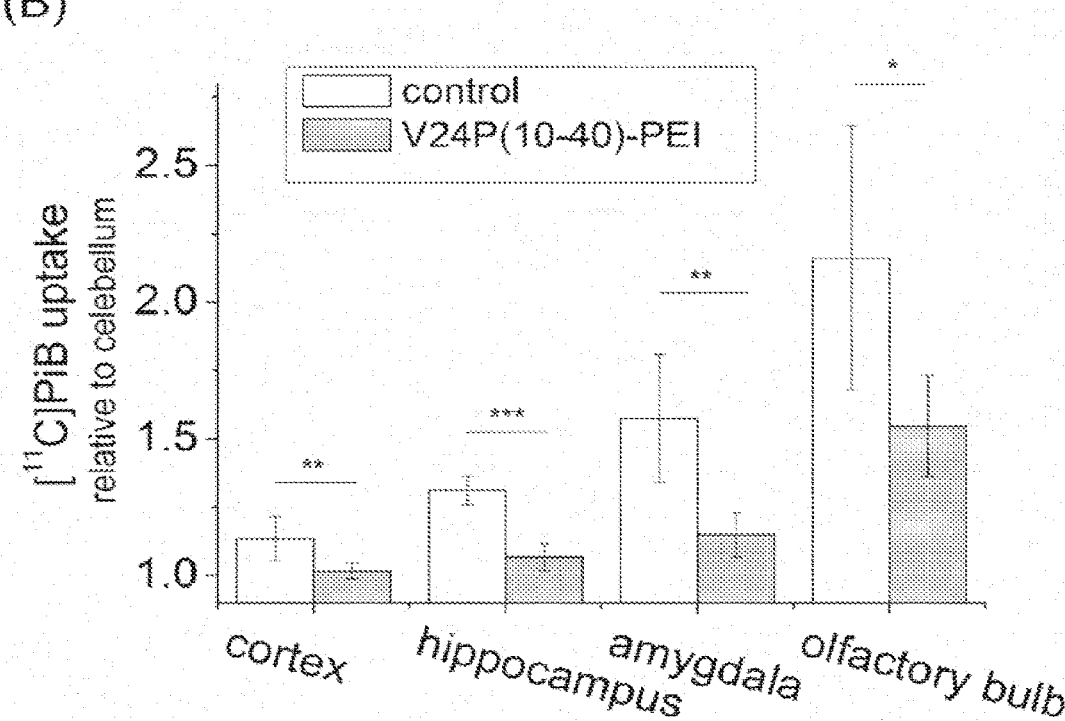

FIG. 23. V24P(10-40)-PEI decreases Aβ plaque accumulation in APP/PS1 mice. Panel A: Representative microPET images of APP/PS1 mice taken after treatment with either PEI (control) or V24P(10-40)-PEI for 8 months. A microPET image of a wild type mouse (WT) is included for comparison. Panel B: Quantitative analysis of [$^{11}$C]PiB uptake in the cortex, hippocampus, amygdala, and olfactory bulb. The data are presented as the mean±standard deviation for 6 mice per group (* p<0.05; p<0.01; *p<0.001, Student's t test).

DETAILED DESCRIPTION OF THE INVENTION

Neurodegenerative diseases are a group of neurological disorders characterized by a gradual loss of neurons in association with the formation of hallmark inclusion bodies (IBs), which results in dysfunction of the nervous system and the eventual demise of patients. Takalo et al., *Am J Neuro Degener Dis* (2013) 2:1-14. Neurodegenerative diseases such as Huntington's disease (HD), Alzheimer's disease (AD), Parkinson's disease (PD), and others are considered as diseases mediated by protein misfolding because of the formation of hallmark inclusion bodies (IBs). Yates, *Nature Reviews* (2012) 11:352-353.

For instance, HD is an autosomal dominantly-inherited neurodegenerative disease caused by an expansion of the CAG trinucleotide repeats in the gene Huntingtin (HTT), which encodes a mutant Htt (mHtt) protein containing a prolonged polyglutamine (polyQ) stretch. Zheng et al., *Progress in Mol Biol and Translational Sci* (2012) 107:189-214. Although having a seemingly simple etiology, HD in fact, is very complex in its pathogenesis (Li et al., *Mol Neurodengener* (2006) 1:19) which involves a large number of important biological processes and signaling pathways that have gone awry. Munoz-Sanjuan et al., *J Clin Invest* (2011) 121:476-83. Currently, no disease-modifying treatment for HD or other neurodegenerative diseases is available. Thus, finding an effective therapeutic regimen is a focus of the neurodegenerative disease community. The aberrant pathways or processes may serve as valuable therapeutic targets (Munoz-Sanjuan et al., *J Clin Invest* (2011) 121:476-83); however, attempts to target these processes would produce undesired side effects as illustrated in the Semagacestat clinical trial for AD. Doody et al., *N Eng J Med* (2013) 369:341-50.

Alzheimer's disease (AD), pathologically defined by the amyloid plaques and neurofibrillary tangles (Nelson et al., *J Neuropathol Exp Neurol* (2012) 71:362-81), is the most common neurodegenerative disease that causes dementia across multiple cognitive domains, and its incidence increases exponentially among people ≥65 years of age. Reitz et al., *Nat Rev Neurol* (2011) 7:137-52. Despite the remarkable scientific advancements and the huge amount of resources invested in drug development based on these discoveries, no effective disease-modifying therapy is currently available for AD. Castellani et al., *Biochem Pharmacol* (2014) 88:671-6. Thus, it is one of the major unmet medical needs worldwide.

Although the etiology of AD remains unclear, alterations in multiple processes have been proposed as important causes and/or contributors, including the amyloid cascade hypothesis. Yamashima *Prog Neurobiol* (2013) 105:1-23; Swerdlow et al., *Biochim Biophys Acta* (2014) 1842:1219-31; Erickson et al., *J Cereb Blood Flow Metab* (2013) 33:1500-13; Clavaguera et al., *Neuropharmacol* (2014) 76 Pt A: 9-15; Castello et al., *Ageing Res Rev* (2013) 12:282-8; Sutherland et al., *Redox Rep* (2013) 18:134-41; Tiiman et al., *Neurochem Int* (2013) 62:367-78; Puglielli *Neurobiol Aging* (2008) 29:795-811; Hardy, *J Alzheimer's Dis* (2006) 9:151-3; and Checler et al., *J Neurochem* (2012) 120 Suppl 1: iii-iv. The amyloid cascade hypothesis proposes that "amyloid β-protein" (Aβ), a peptide of different lengths (39-43 amino acids) with variations and modifications at both termini, plays a central and initiative role in AD pathogenesis and/or progression. Hardy et al., *Science* (1992) 256:184-5; Hardy et al., *Science* (2002) 297:353-6; Tanzi et al., *Cell* (2005) 120:545-55. Aβ is derived from amyloid precursor protein (APP). During normal or non-amyloidogenic catabolism APP is cleaved by α- and γ-secretases, while, in amyloidogenic catabolism, it is cleaved by β- and γ-secretases. The difference in length of the Aβ peptide is partially due to the variance in the cutting sites of γ-secretase. Aβ peptides tend to self-aggregate into amyloid fibrils and more cytotoxic oligomers. Walsh et al., *J Neurochem* (2007) 101:1172-84. Aβ40 and Aβ42 are two main species of Aβ peptides recovered from amyloid plaques with the latter being more prone to aggregate and cytotoxic.

Amyloid plaques belong to a large family of inclusion bodies (IBs), which are characteristics of a variety of neurodegenerative diseases, including Parkinson's disease (PD), Huntington's disease (HD), and amyotrophic lateral sclerosis (ALS). In spite of the differences in the constituent proteins and complexity of the assembly mechanism, the co-existence of different neurodegenerative diseases and associated IBs is well-recognized in a substantial subset of patient cohorts. Keith-Rokosh *Can J Neurol Sci* (2008) 35:602-8; Tada et al., *Acta Neuropathol* (2012) 124:749-60; Schwab et al., *J Neuropathol Exp Neurol* (2008) 67:1159-65; Amador-Ortiz et al., *Ann Neurol* (2007) 61:435-45; Arai et al., *Acta Neuropathol* (2009) 117:125-36; Szpak et al., *Folia Neuropathol* (2001) 39:63-71. In addition, abundant evidence demonstrates that misfolded proteins from different diseases can cross-seed each other to co-aggregate. Jucker et al., *Ann Neurol* (2011) 70:532-40; Ma et al., *J Mol Biol* (2012) 421:172-84; Guo et al., Cell (2013) 154:103-17; Waxman et al., *J Neurosci* (2011) 31:7601-18; Vitrenko et al., *J Biol Chem* (2007) 282:1779-87; Wasmer et al., *J Mol Biol* (2010) 402:311-25; Yan et al., *Am J Pathol* (2007) 171:172-80. These findings suggest that the formation of IBs may be governed, at least in part, by a common set of thermodynamic principles (Jucker et al., *Ann Neurol* (2011) 70:532-40), and interference with the association pathway toward the most thermodynamically stable oligomers or fibrils sheds light on amyloidosis therapy.

Conceptually, reducing the toxic species (the abnormal aggregates) formed by the misfolded protein or its derivative may be a practical and safe therapeutic strategy. Mielcarek et al., *PLOS Biol* (2013) 11: e1001717; Appl et al., *Drug Discovery Today* (2012) 17:1217-23. In HD, the prolonged polyQ confers an aberrant propensity for self-aggregation to form neurotoxic species to the mHtt protein. Oligomer or large fibrillary aggregates in nuclei and processes of neurons and glia are linked with HD pathogenesis. Olshina et al., *J Biol Chem* (2010) 285:21807-16; Ren et al., *Nat Cell Biol* (2009) 11:219-25; Hoffner et al., *Prion* (2007) 1:26-31; Marcellin et al., *PLOS One* (2012) 7: e44457; and Legleiter et al., *J Biol Chem* (2010) 285:14777-90. Indeed, this approach has been tested in several neurodegenerative disease models including HD (Kordasiewicz et al., *Neuron* (2012) 74:1031-44; Sontag et al., *J Neurosci* (2012) 32:11109-19) and AD (Aisen et al., *Current Alzheimer Research* (2007) 4:473-78; Frisardi et al., *Current Alzheimer Research* (2010) 7:40-55) with encouraging results.

Since the formation of toxic misfolded proteins/derivatives is governed by a common set of thermophysical laws across different diseases, a common strategy as described herein be used to develop therapeutic tools by reducing the formation of the misfolded species in these neurodegenerative diseases.

Figure 1:
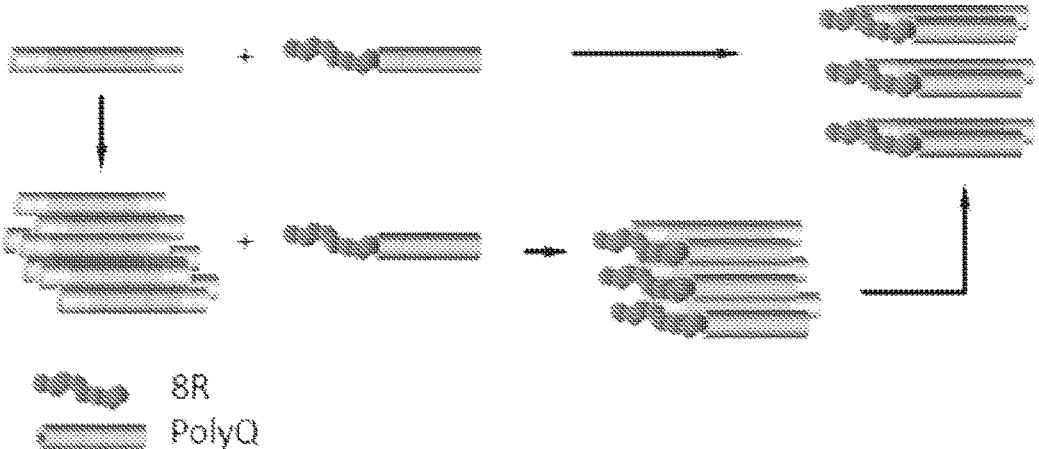
FIG. 1. Schematic illustration of the modular design of the therapeutic peptide for HD.

Accordingly, described herein is a rational design of therapeutic peptides that are expected to reverse the pathogenic process of IB formation in a neurodegenerative disease as those described herein. Here, novel bipartite molecules containing at least one affinity module and at least one charged module were designed and their efficacy was demonstrated using cellular, APP/PS1 AD models, and R6/2 HD models. The bipartite molecules would reduce toxic abnormal protein aggregates across various neurodegenerative diseases. The rational design is built on a principle of modular assembly of an affinity portion (e.g., a peptide affinity moiety) and at least one charged moiety, e.g., positively charged or negatively charged. Without being bound by theory, the affinity moiety would facilitate binding of such therapeutic molecules (bipartite molecules) to a protein component of an abnormal protein aggregate or a monomer of the abnormal protein aggregate and the charged portion(s) would prevent or reduce the formation of the abnormal protein aggregate by, e.g., the repulsion force of charges (FIG. 1).

The approach described herein possesses several unique features and advantages as compared with current therapeutic approaches for neurodegenerative diseases. Some examples are provided below. First, the affinity moiety, which may be taken from the pathogenic peptide/protein forming the abnormal aggregate not only significantly reduces laborious work finding and optimizing suitable peptide sequences, but also guarantees high affinity with IBs through its self-aggregating property. Second, the multiple charges in the charged moiety (e.g., a polyR fragment) render the bipartite molecules described herein (a) soluble in an aqueous environment, thereby simplifying the synthesis and delivery processes and (b) cell-penetrable (Mitchell et al., *J Pept Res* (2000) 56:318-25), making them suitable for inhibiting both extracellular and intracellular IB formation. Further, the charged moiety in the bipartite molecules can prevent or reduce IB formation by charge repulsion after binding of the bipartite molecules to the pathogenic peptide/ protein or protein aggregate. Third, the combination of the charged moiety with the affinity moiety provides great feasibility and flexibility in applying this design across different IB-containing diseases.

Accordingly, the present disclosure provides bipartite molecules comprising an affinity moiety that binds an abnormal protein aggregate associated with a disease or a component thereof (e.g., a protein monomer that forms the abnormal protein aggregate) and at least one charged moiety, and uses of such bipartite molecules in preventing or reducing the formation of the abnormal protein aggregates and/or in treating diseases (e.g., neurodegenerative diseases) involving such abnormal protein aggregates.

I. Bipartite Molecules

The bipartite molecule described herein comprise (i) a peptide affinity moiety, which is capable of binding to an abnormal protein aggregate, or a component of that abnormal aggregate, and (ii) at least one charged moiety (e.g., positively charged or negatively charged), which facilitates the bipartite molecule to cross cell membranes and prevent or decrease formation of the abnormal protein aggregation associated with a disease, such as a neurodegenerative disease as those described herein.

(i) Peptide Affinity Moiety

The peptide affinity moiety of the bipartite molecule can be any peptide-based (e.g., comprising a peptide) molecule capable of binding to a targeted abnormal protein aggregates or a protein component thereof (e.g., a monomer capable of forming the abnormal protein aggregates or a fragment thereof which is involved in the aggregate formation). The peptide affinity moiety may contain a peptide having up to 100 (e.g., 80, 60, 50, 40, 30, 20, or 10) amino acid residues, which can contain either naturally-occurring amino acids or modified ones such as D-amino acids, or a combination thereof. In some examples, the peptide affinity moiety may contain a peptide having 5-10, 5-20, 5-30, 10-15, 10-20, 10-30, or 20-30 amino acid residues. The peptide affinity moiety may be methylated or acetylated at the N-terminus, amidated at the C-terminus, or both to enhance stability.

Disease-associated abnormal protein aggregates and the corresponding protein constituents are known in the art. Some examples are provided in Table 1 below:

TABLE 1

Exemplary Neurodegenerative Diseases and Abnormal Protein Aggregates Associated with such Diseases

| Exemplary Diseases involving abnormal protein aggregates | Aggregate type | Associated protein components |
|---|---|---|
| Alzheimer's disease [AD] | amyloid plaques, neuro-fibrillary tangles | amyloid precursor protein, amyloid β, presenilin 1&2, tau, neurofilament protein, alpha B-crystallin, transthyretin |

TABLE 1-continued

Exemplary Neurodegenerative Diseases and Abnormal Protein Aggregates Associated with such Diseases

| Exemplary Diseases involving abnormal protein aggregates | Aggregate type | Associated protein components |
|---|---|---|
| Huntington's disease [HD] | inclusion bodies | uintingtin protein, expanded polyglutamine tract in huntingtin protein, alpha B-crystallin |
| Parkinson's disease [PD] | Lewy bodies | alpha-synuclein, ubiquitin, neurofilament protein, alpha B-crystallin |
| Dementia with Lewy body [DLB] | Lewy bodies | alpha-synuclein, ubiquitin |
| Amyotrophic lateral sclerosis [ALS] | inclusion bodies | SOD-1, TAR DNA binding protein (TDP-43, or TARDBP), FUS, ubiquitin, neurofilament protein |
| Frontotemporal lobar degeneration [FTLD]-TDP-43 proteinopathy | inclusion bodies | ubiquitin, TDP-43 |
| Frontotemporal lobar degeneration [FTLD]-Tauopathy | Pick bodies | tau, fused in sarcoma (FUS), alpha B-crystallin |
| Cortical basal degeneration [CBD] | Astroglial inclusions | tau |
| Progressive supranuclear palsy [PSP] | neurofibrillary tangles, Lewy bodies | tau, Tau H1 halotype |
| Frontotemporal dementia and parkinsonism linked to chromosome 17 [FTDP-17] | Lewy bodies | microtubule-associated protein tau [MAPT], tau |
| Creutzfeldt-Jacob disease [CJD] | Aggregates and spongiform change | prion protein (PRNP), prion in the Scrapie form (PrP$^{SC}$) |

In some embodiments, the peptide affinity moiety may contain an amino acid sequence derived either from a disease protein, which forms the abnormal protein aggregate or from the region of other proteins that interact with the disease protein or the abnormal protein aggregate formed thereby. In some embodiments, the peptide affinity moiety comprises a fragment of the disease protein (e.g., any of those listed in Table 1 above) that is involved in self-aggregation (formation of the abnormal protein aggregates).

In some examples, the peptide affinity moiety comprises a polyQ fragment. Such a peptide affinity moiety can bind to and reduce/disrupt formation of protein aggregates involving polyQ, for example, the aggregation of mHtt involved in HD. The polyQ moiety may comprise at least 2, at least 5, at least 10, at least 15, at least 20 at least 25, at least 30, or at least 50 glutamine (Q) amino acid residues (e.g., 5-10, 5-15, 5-20, 5-30, or 10-20 Q residues). In some embodiments the peptide affinity moiety is 5Q, 10Q, 15Q, or 20Q.

The protein affinity moiety may contain a fragment derived from a wild-type disease protein (as those listed in Tables 1, 3, and 4 and described herein) or from a mutant form or modified form of the disease protein, particularly those involved in disease pathogenesis. The modified form of the protein may include post translational modifications such as phosphorylation. For example, neurofibrillary tangles (NFTs) may be formed by hyperphosphorylation of the microtubule-associated protein Tau. Accordingly, the peptide affinity moiety may contain the hyperphosphorylated form, or a portion of the hyperphosphorylated form of Tau. Hyperphosphorylation may be achieved by employing the use of various known kinases or by phosphomimetic amino acid substitutions that mimic a phosphorylated protein. For example, aspartic acid (D) is chemically similar to phospho-serine. Therefore, when aspartic acid replaces a serine, it is a phosphomimetic of phospho-serine.

In some embodiments, the peptide affinity moiety may contain a fragment derived from amyloid β-protein, SOD1, Tau, TDP-43, α-synuclein, ubiquitin, neurofilament protein, alpha B crystalline, PrP$^{SC}$, or transthyretin. Such a fragment may involve in formation of protein aggregate containing the disease protein. For example, fragment Aβ25-35 from amyloid β-protein, which may contain an N-methylated Gly33, can interact with amyloid plaques. Hughes et al., *J Biol Chem* (2000) 275:25109-115. In another example, an Aβ40 mutant peptide, V24P, with the V24 replaced by D-form proline ($^{D}$P), remains as random coils in buffer and forms amorphous aggregates at a high peptide concentration. Chang et al., *J Mol Biol* (2009) 385:1257-65. Mixing V24P with Aβ40 at a 1:1 molar ratio inhibits amyloid formation and the cytotoxicity of Aβ40. Iwata et al., *Pharmacol Therapeut* (2005) 108:129-48.

In some examples, the peptide affinity moiety may comprise the amino acid sequence GSNKGAIIGLM (SEQ ID NO: 1), which is derived from amyloid β-protein. Alternatively, the affinity moiety may comprise the amino acid sequence YEVHHQKLVFFAED$^{D}$PGSNK-GAIIGLMVGGVV (SEQ ID NO: 2), in which $^{D}$P refers to the D-form of proline. In another example, the affinity moiety may comprise RPRTRLHTHRNR (SEQ ID NO: 8), which may be an Aβ$_{42}$-binding 12-mer D-form peptide as described in Wiesehan et al. (*Chem Bio Chem* (2003) 4:748-53), the relevant teachings therein are incorporated by reference herein. Other exemplary amyloid β-protein fragments for use as the peptide affinity moiety in making the bipartite molecules described herein are provided in Table 3 below.

Any of the peptide affinity moieties as described herein can be prepared by, e.g., chemical synthesis or recombinant technology.

(ii) Charged Moiety

The charged moiety of the bipartite molecule may prevent or reduce the formation of abnormal protein aggregates by misfolded disease proteins or may lead to dissociation of existing abnormal protein aggregates by the force of charge repulsion. See, e.g., FIG. 1. Further, the charged moiety may facilitate the bipartite molecule containing such to cross cell membranes and/or blood brain barrier (BBB).

In some embodiments, the charged moiety may contain a peptide comprising up to 100 (e.g., 80, 60, 50, 40, 30, 20, or 10) amino acid residues, which may contain at least 2, at least 4, at least 5, at least 8, at least 10, at least 15, at least 20, at least 25, or at least 30 charged amino acids. In some examples, the charged moiety may be a peptide having all charged amino acid residues. For example, the peptide may contain at least one (e.g., at least 2, 4, 5 or 10) negatively charged amino acid, e.g., aspartic acid (e.g., a polyD fragment) or glutamic acid (e.g., a polyE fragment), or a combination of D and E amino acids. Alternatively, the peptide may contain at least one (e.g., at least 2, 4, 5, or 10) positively charged amino acid, e.g., arginine, histidine, lysine, or a combination thereof. In some examples, the charged moiety contains a stretch of arginine (e.g., a polyR fragment) or lysine residues (e.g., a polyK fragment). As used herein, a polyR, polyK, polyD, or polyE fragment refers to a stretch of R, K, D, or E residues. Such a fragment may contain up to 30 (e.g., 25, 20, 15, 10 or 5) R, K, D, or E residues. In some examples, the charged moiety may be a peptide containing a combination of different negatively charges amino acids or a combination of different positively charged amino acids.

In addition to preventing the misfolded target protein from forming abnormal protein aggregates or to dissociate it from existing aggregates, a charged moiety described herein, for example, a polyR fragment, can facilitate a bipartite molecule comprising such to penetrate through cell membranes, the blood brain barrier (BBB), or both. In some embodiments, the charged moiety has the amino acid sequence RRRRRRRR (SEQ ID NO: 9).

In some embodiments, the charged moiety can be a cell-penetrating peptide (CPP) such as TAT, referring to a peptide comprising the amino acid sequence of GRKKRRQRRRPQ (SEQ ID NO: 10), which is derived from the transactivator of transcription (TAT) of human immunodeficiency virus. Cell-penetrating peptides (CPPs) have been used to overcome the lipophilic barrier of the cellular membranes and deliver both large molecules and even small particles (e.g., proteins, DNA, antibodies, contrast (imaging) agents, toxins, and nanoparticular drug carriers including liposomes) inside the cell for their biological actions. A peptide-based charged moiety may be prepared by chemical synthesis or recombinant technology.

In other embodiments, the charged moiety may be a non-peptide polymer, such as a polyethylenimine (PEI) molecule. Methods for synthesizing PEI-conjugated peptides are well known in the art. For example, PEI conjugated peptides may be synthesized by the batch fluorenylmethoxycarbonyl (fmoc)-polyamide method.

(iii) Configurations of the Affinity and Charged Moieties in the Bipartite Molecules In any of the bipartite molecules as described herein, the peptide affinity moiety and the charged moiety or moieties are linked (e.g., covalently) and may be configured in a suitable manner. In some embodiments, the bipartite molecule contains a peptide affinity moiety as described herein and a single charged moiety. The charged moiety can be attached to either the N-terminus or the C-terminus of the peptide affinity moiety, either directly or via a suitable linker. If the charged moiety is also peptide based, the peptide affinity moiety and the charged peptide may be linked via a peptide bond. If the charged moiety is a non-peptide polymer, such as PEI, the non-peptide polymer may be linked to either the N-terminus or the C-terminus of the peptide affinity moiety via a suitable bond (e.g., a suitable covalent bond).

In some embodiments, the bipartite molecule may contain two charged moieties, which can be either identical or different. In other examples, the two charged moieties are both polyR fragments. For example, a poly-arginine (polyR) moiety having eight arginine residues is linked to the amino-terminus of the peptide affinity moiety and another poly-arginine (polyR) moiety having eight arginine residues can be linked to the carboxy-terminus of the peptide affinity moiety.

In some embodiments, the two charged moieties can be different. For example, one of the charged moieties can be a peptide-based moiety such as a polyR fragment and the other charged moieties can be a non-peptide polymer such as PEI. The polyR fragment and PEI may be linked to the N-terminus and C-terminus of the peptide affinity moiety, respectively, or vice versa. In some embodiments the two charged moieties may have opposing charges. For example, a positively charged poly-arginine (polyR) moiety may be linked to the amino-terminus and a negatively charged poly-aspartate (polyD) moiety may be linked to the carboxy-terminus of the peptide affinity moiety. In some examples, the charged moieties may both carry a positive charge or both carry a negative charge. For example, a positively charged poly-arginine (polyR) moiety may be linked to the amino-terminus and a positively charged poly-lysine (polyK) moiety may be linked to the carboxy-terminus of the peptide affinity moiety. In some embodiments the bipartite molecule is RRRRRRRRRGSNKGAIIGLM-PEI (SEQ ID NO: 4). It should be appreciated that the charged moiety, or moieties, of the bipartite molecule, as described herein, may be configured in any number of ways with respect to the peptide affinity moiety.

In some examples, the peptide moiety or moieties may be modified at the C-terminus (e.g., acetylation), the N-terminus (e.g., methylation), or both for at least enhancing stability of the bipartite molecule containing such.

II. Pharmaceutical Compositions

The bipartite molecules described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the bipartite molecules (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No.

5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The bipartite molecules may also be entrapped in microcapsules prepared, for example, by coacervation techniques or by interfacial polymerization, for example, hydroxymethylcellulose or gelatin-microcapsules and poly-(methyl-methacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the bipartite molecule, which matrices are in the form of shaped articles, e.g., films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic bipartite molecule compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing bipartite molecules with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

III. Methods of Treatment

Any of the bipartite molecules are useful in preventing/reducing the formation of protein aggregates associated with a disease such as a neurodegenerative disease as described herein, or disrupting such a protein aggregate. The bipartite molecule can also be used for treating a disease or disorder, particularly a neurodegenerative disease or disorder, characterized by abnormal protein aggregates.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the bipartite molecules as described herein can be aerosolized using a fluorocarbon formulation and a metered dose inhaler, or inhaled as a lyophilized and milled powder. In one example, the bipartite molecule is administered via an intranasal route, e.g., by nasal drops.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as Alzheimer's disease (AD), Huntington's disease (HD), Parkinson's disease (PD), dementia with Lewy bodies (DLB), amyotrophic lateral sclerosis (ALS), frontotemporal lobar degeneration-TDP-43 proteinopathy, frontotemporal lobar degeneration-tauopathy (Pick's disease, cortical basal degeneration, progressive supranuclear palsy, FTDP-17), Creutzfeldt-Jacob disease (CJD), or another disease. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced abnormal protein aggregates, or the prevention of abnormal protein aggregate formation. Determination of whether an amount of the bipartite molecule achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a bipartite molecule may be appropriate. Various formulations and devices for achieving sustained release are known in the art.

In one example, dosages for a bipartite molecule as described herein may be determined empirically in individuals who have been given one or more administration(s) of the bipartite molecule. Individuals are given incremental dosages of the antagonist. To assess efficacy of the antagonist, an indicator of the disease/disorder can be followed.

Generally, for administration of any of the bipartite molecules described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the bipartite molecule, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the bipartite molecule used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a bipartite molecule as described herein will depend on the specific bipartite molecule, bipartite molecules, the type and severity of the disease/disorder, whether the bipartite molecule is administered for preventive or therapeutic purposes, previous therapy, the patient's clinical history and response to the antagonist, and the discretion of the attending physician. A clinician may administer a bipartite molecule, until a dosage is reached that achieves the desired result. In some embodiments, the desired result is a decrease in abnormal protein aggregates. Methods of determining whether a dosage resulted in the desired result would be evident to one of skill in the art. Administration of one or more bipartite molecules can be continuous or intermittent, depending, for example, upon the recipient's physiological condition, whether the purpose of the administration is therapeutic or prophylactic, and other factors known to skilled practitioners. The administration of an bipartite molecule may be essentially continuous over a preselected period of time or may be in a series of spaced dose, e.g., either before, during, or after developing a target disease or disorder. In some examples, the amount of the bipartite molecule is effective in reducing the formation of an abnormal protein aggregate by at least 20%, e.g., 30%, 40%, 50%, 60%, 70%, 80%, 90%, 95%, or above.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the bipartite molecules described herein are administered to a subject in need of the treatment at an amount sufficient to reduce abnormal protein aggregates by at least 5% (e.g., 10%, 20%, 30%, 40%, 50%, 60%, 70%, 80%, 90% or greater) in vivo. In other embodiments, the bipartite molecules are administered in an amount effective in reducing the activity level of a target antigens by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical compositions is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble bipartite molecules can be administered by the drip method, whereby a pharmaceutical formulation containing the bipartite molecule and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the bipartite molecule, can be dissolved and administered in a pharmaceutical excipient such as Water-for-Injection, 0.9% saline, or 5% glucose solution.

In one embodiment, a bipartite molecule is administered via site-specific or targeted local delivery techniques. Examples of site-specific or targeted local delivery techniques include various implantable depot sources of the bipartite molecule or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the bipartite molecules described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

In some examples, patients with or at risk for Huntington's disease may be treated with a bipartite molecule having an affinity moiety that comprises polyQ attached to at least one charged moiety. In some embodiments the bipartite molecule is RRRRRRRRWDQQQQQQQQQQQ (SEQ ID NO: 6), or RRRRRRRRWDQQQQQQQQQQQQQQQQ (SEQ ID NO: 7). Alternatively, a patient with or at risk for Alzheimer's disease may be treated with a bipartite molecule having an affinity moiety that comprises a portion of the amyloid β-protein attached to at least one charged moiety. In some embodiments the bipartite molecule is RRRRRRRRRGSNK-GAIIGLM (SEQ ID NO: 3), RRRRRRRRRGSNK-GAIIGLM-PEI (SEQ ID NO: 4), or YEVHHQKLVFFAE-D$^D$PGSNKGAIIGLMVGGVV-PEI (SEQ ID NO: 5).

The particular dosage regimen, i.e., dose, timing and repetition, used in the method described herein will depend on the particular subject and that subject's medical history.

In some embodiments, more than one bipartite molecule, or a combination of a bipartite molecule and another suitable therapeutic agent, may be administered to a subject in need of the treatment. The bipartite molecule can also be used in conjunction with other agents that serve to enhance and/or complement the effectiveness of the agents.

Treatment efficacy for a target disease/disorder can be assessed by, e.g., a method described in the Examples below.

IV. Kits for Use in Alleviating Neurodegenerative Diseases Associated Abnormal Protein Aggregates The present disclosure also provides kits for use in alleviating diseases/disorders associated abnormal protein aggregates, such as Alzheimer's disease (AD), Huntington's disease (HD), Parkinson's disease (PD), dementia with Lewy bodies (DLB), amyotrophic lateral sclerosis (ALS), frontotemporal lobar degeneration-TDP-43 proteinopathy, frontotemporal lobar degeneration-tauopathy (Pick's disease, cortical basal degeneration, progressive supranuclear palsy, FTDP-17), or Creutzfeldt-Jacob disease (CJD). Such kits can include one or more containers comprising a bipartite molecule, e.g., any of those described herein.

In some embodiments, the kit can comprise instructions for use in accordance with any of the methods described herein. The included instructions can comprise a description of administration of the bipartite molecule to treat, delay the onset, or alleviate a target disease as those described herein. The kit may further comprise a description of selecting an individual suitable for treatment based on identifying whether that individual has the target disease. In still other embodiments, the instructions comprise a description of administering a bipartite molecule to an individual at risk of the target disease.

The instructions relating to the use of a bipartite molecule generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with the presence of abnormal protein aggregates, such as those described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a bipartite molecule as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P.

Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described herein may be more fully understood, the following examples are set forth. The examples described in this application are offered to illustrate the molecules, pharmaceutical compositions, and methods provided herein and are not to be construed in any way as limiting their scope.

Figure 2:
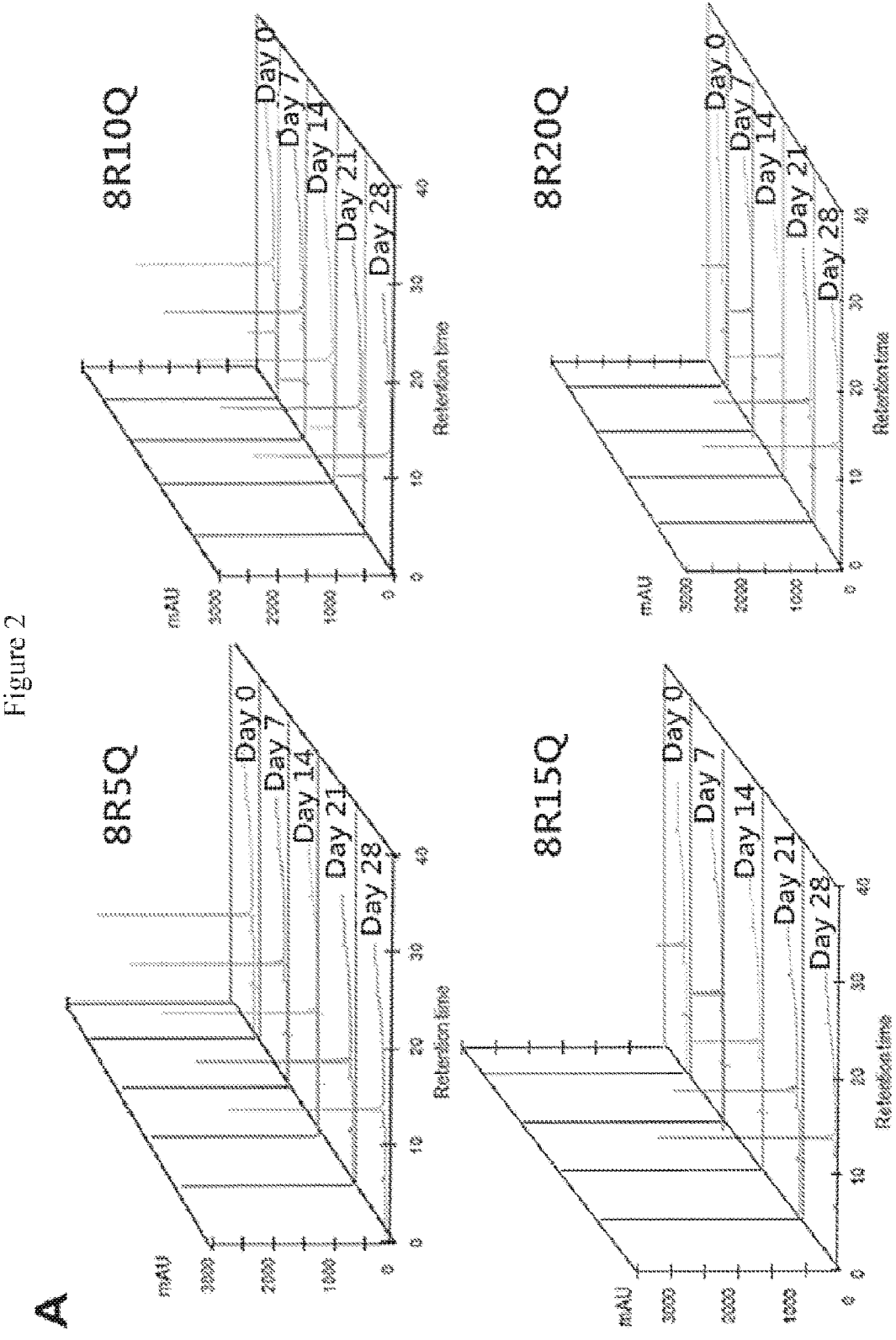
FIG. 2. Stability of the therapeutic peptides determined by HPLC. A: diagrams showing the retention time of the tested peptides from day 0 to day 28. B: charts showing the amount of the tested peptides at day 0 and day 28. Note the 8R5Q and 8R10Q remained stable in water for 28 days, but the soluble 8R15Q and 8R20Q gradually decreased with time.
Figure 2:
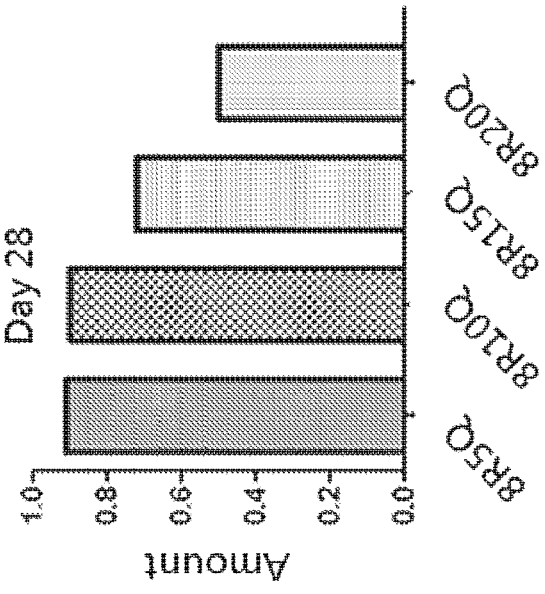
Figure 2:
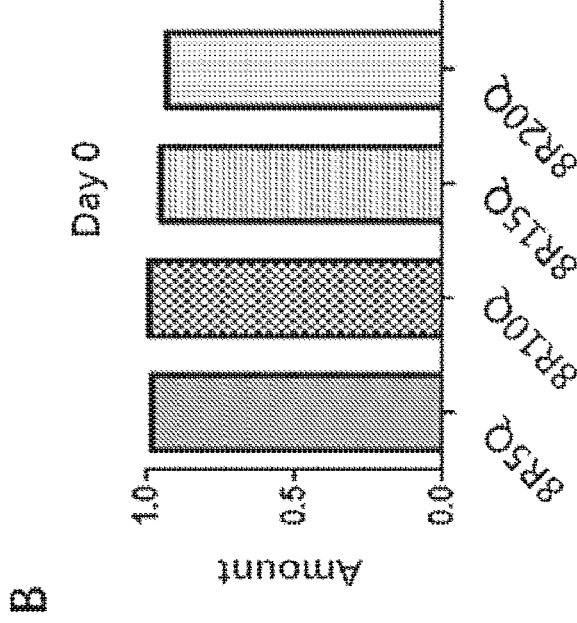

Example 1: Exemplary Bipartite Therapeutic Peptides and Uses Thereof in Treating Huntington's Disease Huntington's disease (HD) is caused by an expansion of the CAG trinucleotide repeats in the Huntingtin (HTT) gene. The expanded CAG repeats encode an elongated polyglutamine stretch (polyQ) within the mutant Htt (mHtt) protein, which leads to the misfolding and aggregation of mHtt. Provided herein is a series of therapeutic peptides, for example, 8R5Q, 8R10Q, 8R15Q and 8R20Q, which contains polyarginines (e.g., 8R) and a short stretch of polyQ (e.g., 5Q, 10Q, 15Q, or 20Q). The polyQ sequence was expected to confer a specific affinity for the therapeutic peptides to bind to mHtt and the polyarginine fragment possesses the capability to penetrate neurons and prevent mHtt/peptide self-aggregation charge repulsion. This was demonstrated by the observation that in Neuro2a cells (mouse neuroblastoma), 8R10Q co-localized with 109QmHtt aggregates. Both 8R10Q and 8R15Q significantly decreased the size of 109QmHtt aggregates. In addition, 8R10Q reduced the level of 109QmHtt, which was blocked by the proteasome inhibitor MG132, indicating that the peptide enhanced cellular ability to degrade 109QmHtt. Functionally, 8R10Q attenuated the 109QmHtt-induced toxicity in the growth of undifferentiated Neuro2a cells by a MTT assay and the retinoic acid-mediated neurite outgrowth of Neuro2a cells. In vivo, 8R10Q significantly delayed the motor and memory deterioration of R6/2 transgenic mice, a HD mouse model. Histopathologically, 8R10Q also reduced the aggregation of mHtt and neuronal loss, and ameliorated the activation of astrocytes and microglia. Intriguingly, 8R10Q decreased the diabetic phenotype, inflammatory index, and abnormal liver function of R6/2 mice. Altogether, the therapeutic peptides designed by this modular principle two peptides were quite stable. In contrast, 8R15Q was partially soluble, but 8R20Q was insoluble, and both underwent a time-dependent decrease in the retention time and amount (FIG. 2, panels A and B) during HPLC analysis, indicating their high stability. Thus, 8R10Q was selected as the lead peptide for subsequent studies given its superior biochemical properties.

TABLE 2

The sequence and biochemical properties of therapeutic peptides.

| Peptide | Sequence | Formula | MALDI-TOF Calculated | Found | Solubility (DMEM/10% FBS) |
|---|---|---|---|---|---|
| 8R | $NH_2$-(R)$_8$-W-D-$CONH_2$ | $C_{63}H_{113}N_{35}O_{13}$ | 1567.8 | 1568.0 | Soluble |
| 8R5Q | $NH_2$-(R)$_8$-W-D-(Q)$_5$-$CONH_2$ | $C_{88}H_{153}N_{45}O_{23}$ | 2208.5 | 2208.5 | Soluble |
| 8R10Q | $NH_2$-(R)$_8$-W-D-(Q)$_{10}$-$CONH_2$ | $C_{63}H_{113}N_{35}O_{13}$ | 2849.2 | 2849.2 | Soluble |
| 8R15Q | $NH_2$-(R)$_8$-W-D-(Q)$_{15}$-$CONH_2$ | $C_{63}H_{113}N_{35}O_{13}$ | 3489.8 | 3489.8 | aggregated |
| 8R20Q | $NH_2$-(R)$_8$-W-D-(Q)$_{20}$-$CONH_2$ | $C_{63}H_{113}N_{35}O_{13}$ | 4130.5 | 4130.5 | aggregated |
| s8R10Q | $NH_2$-RQQRRQQDQRQWQRQRQQRR-$CONH_2$ | $C_{63}H_{113}N_{35}O_{13}$ | 2849.2 | 2849.5 | Soluble |
| TAMRA-8RWD | TAMRA-NH-(R)$_8$-W-D-$CONH_2$ | $C_{63}H_{113}N_{35}O_{13}$ | 1982.3 | 1981.0 | Soluble |
| TAMRA-8R10Q | TAMRA-NH-(R)$_8$-W-D-(Q)$_{10}$-$CONH_2$ | $C_{63}H_{113}N_{35}O_{13}$ | 3264.7 | 3264.6 | Soluble |
| TAMRA-s8R10Q | TAMRA-NH-RQQRRQQDQRQWQRQRQQRR-$CONH_2$ | $C_{63}H_{113}N_{35}O_{13}$ | 3264.7 | 3264.6 | Soluble | s8R10Q: scrambled 8R10Q worked against HD, which may also shed light on the development of a therapeutic strategy against other neurodegenerative diseases.

Design and Synthesis of the Bipartite Peptides

The rational design of therapeutic peptides to reduce the toxic misfolded proteins/derivatives across different neurodegenerative diseases based on the principle of modular assembly was attempted. The conjectured therapeutic peptides would assume a bipartite or tripartite structure composed of a full or partial sequence from the self-aggregating region of the misfolded protein (e.g., mHtt or amyloid β peptide, etc.) flanked either upstream or downstream (bipartite) or both (tripartite) by a stretch of charged amino acids. The rationale behind this design was that the self-aggregating sequence would provide a specific affinity between the peptide and the misfolded protein/derivative through its self-aggregating property. The charged amino acid chosen in the study may be arginine. Polyarginine stretch enabled the therapeutic peptides to penetrate through cell membrane into cytoplasmic and nuclear compartments (Mitchell, *J Pept Res* (2000) 56:318-25). It was also expected to prevent therapeutic peptides from self-aggregation. Moreover, polyarginine can prevent the mHtt/peptide hybrids from self-aggregation by charge repulsion force (FIG. 1).

In this study, the rational design was tested for HD. Several bipartite therapeutic peptides containing 8 consecutive arginines (8R) attached to a stretch of consecutive glutamines (polyQ) were synthesized and their biological activity of decreasing the aggregation propensity of the mHtt protein was investigated. The length of the polyQ of these bipartite peptides was 5 (8R5Q), 10 (8R10Q), 15 (8R15Q) or 20 (8R20Q) (Table 2). Peptides 8R5Q and 8R10Q were highly soluble in water or culture medium (Table 2), and remained unchanged in their retention time and amount for at least 28 days (FIG. 2, panels A and B), indicating these The sequence in Table 2, from top to bottom, correspond to SEQ ID NOs: 11-19.

Decreasing mHtt Aggregation by PolyR-PolyQ Peptide

Figure 3:
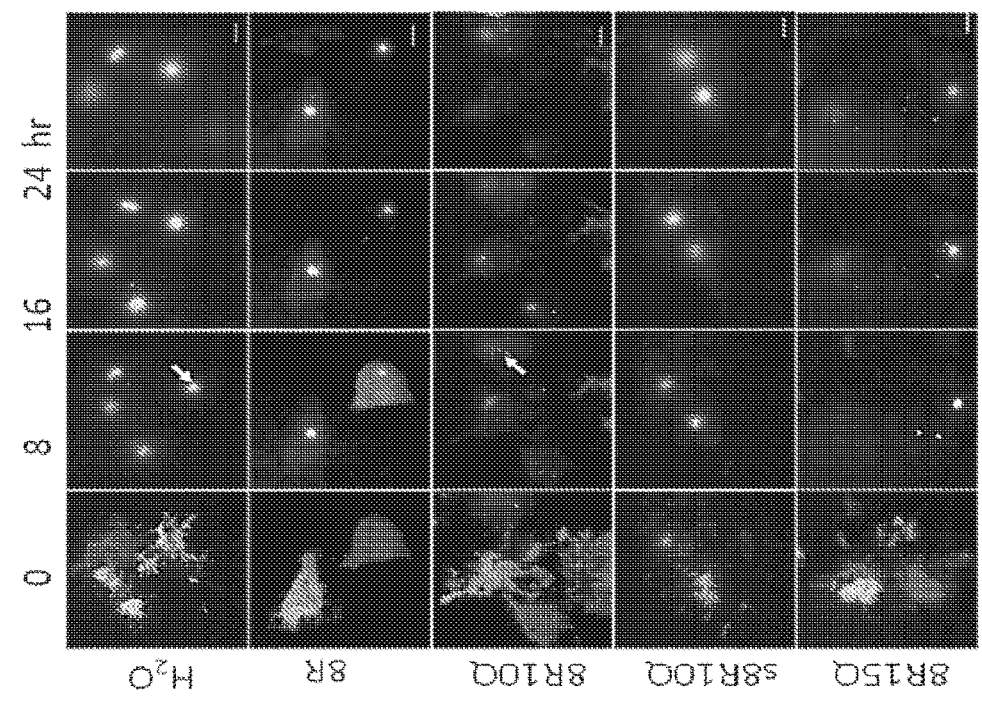
FIG. 3. Diagrams showing the co-localization of tested bipartite peptides with the 109QmHtt aggregates. Panel A: Structure of TAMRA-labeled 8R10Q used in this study. Panel B: Epifluorescence micrographs of Neuro2a cells expressing 109QmHtt treated with TAMRA-8R10Q (8R10Q) at various time points. Note the co-localization of 8R10Q and 109QmHttGFP aggregates (GFP) from 8-24 hours (arrows). Scale bar: 10 μm. Panel C: TIRF micrographs of the Neuro2a expressing 109QmHtt treated with water or peptides as indicated at various time points. Note the decrease in aggregate size in 8R10Q and 8R15Q-treated cells. Panel D: Quantitation of the size of individual aggregates in Neuro2a at 8 hours (left) and 24 hours (right) after peptide treatment. The size was significantly decreased by 8R10Q or 8R15Q peptide at both time points. Panel E: Quantitation of the number of aggregates in 20 Neuro2a cells at 12 hours (left) and 24 hours (right) after peptide treatment. Both the 8R10Q and 8R15Q increased the number of aggregates. Statistics performed with one way ANOVA. $p<0.01$; *$p<0.001$.
Figure 3:
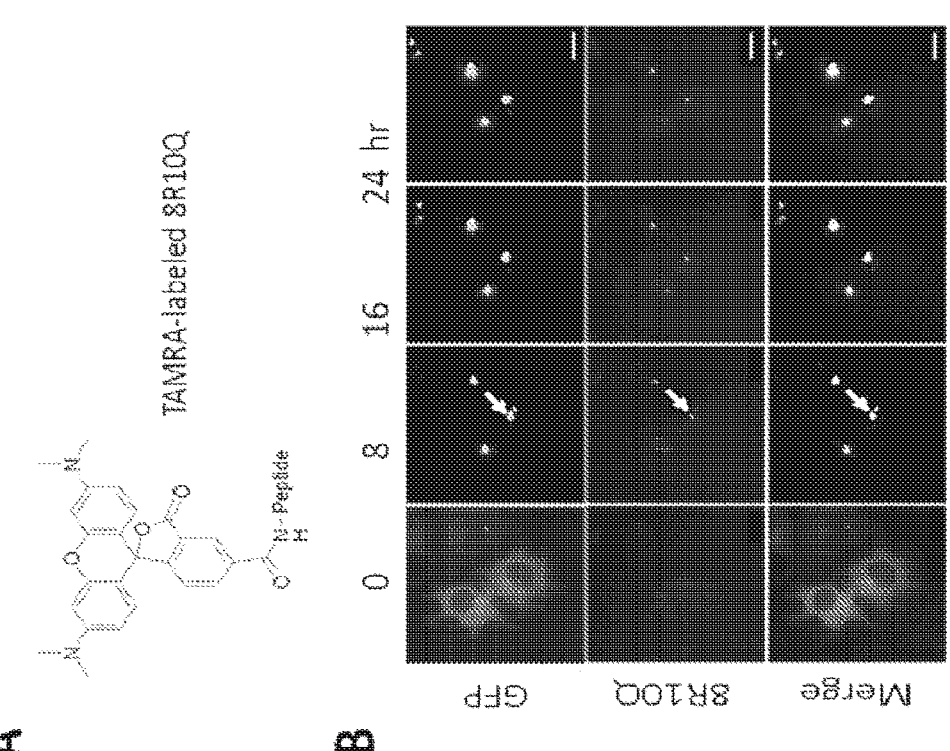
Figure 3:
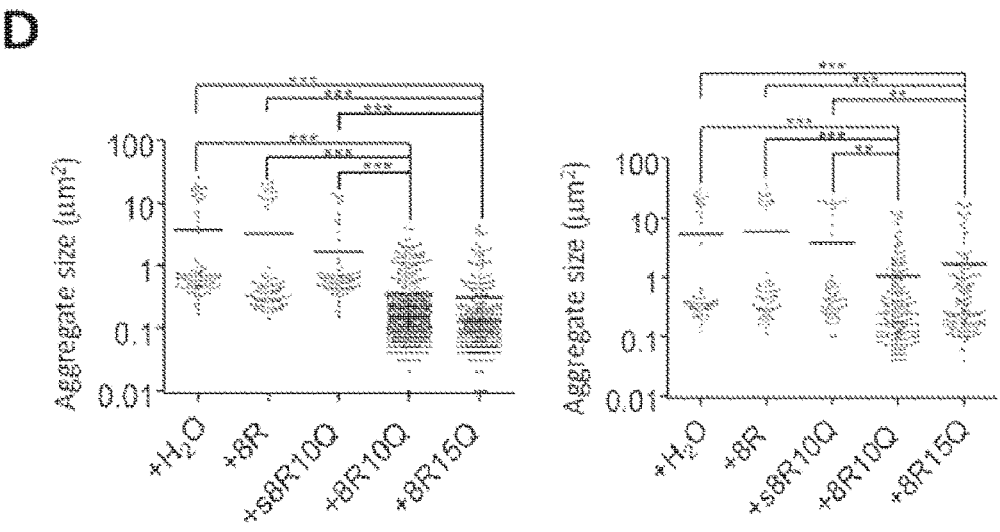
Figure 3:
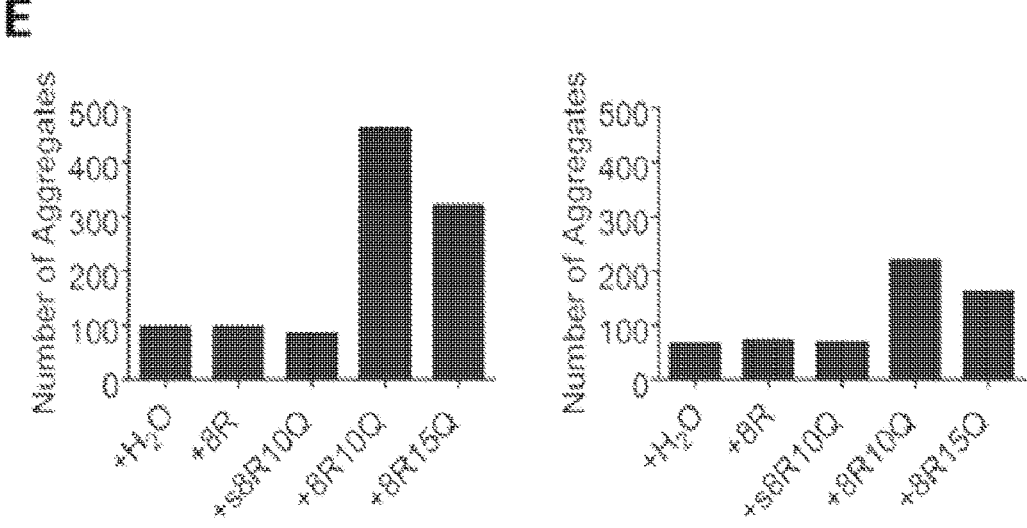

The ability of 8R10Q to bind to the 109QmHtt was examined by determining its co-localization with the 109QmHtt aggregates. The 8R10Q peptide was labeled with carboxytetramethylrhodamine (TAMRA) dye (FIG. 3, panel A), and added into Neuro2a cells expressing 25QHtt or 109QmHtt. The TAMRA dye alone failed to associate with the 109QmHtt aggregates, and the labeled 8R10Q also failed to conform to the pattern of 25QHtt. In contrast, the TAMRA-labeled 8R10Q peptide was co-localized with the aggregates (FIG. 3, panel B). These results clearly validated the ability of 8R10Q to interact with the mHtt, as expected.

To probe into the details of the effect of peptide on the mHtt aggregates, the parameters of the mHtt aggregates were visualized and measured using the Total Internal Reflection Fluorescence (TIRF) microscopy. As shown in FIG. 3, panel C, large solid 109QmHtt aggregates were readily observed in the Neuro2a cells treated with water, 8R, or a scrambled peptide (s8R10Q); however, mainly small punctate aggregates were seen in cells treated with 8R10Q, which remained so throughout the tested time points. Quantitative data showed that the average size of the aggregates from water, 8R or scrambled peptide-treated cells were 3.6 $\mu m^2$, 3.3 $\mu m^2$, 1.7 $\mu m_2$, respectively; while those from the 8R10Q- or 8R15Q-treated cells were dramatically reduced to 0.3 $\mu m^2$ and 0.2 $\mu m^2$, respectively (FIG. 3, panel D). Notably, a subset of the aggregates in the former control groups were larger than 10 $\mu m^2$, which were never identified in the latter. The number of aggregates in 20 cells was also calculated. 8R10Q and 8R15Q increased the number of the aggregates by 4-5 fold (FIG. 3, panel E). These results suggested that 8R10Q or 8R15Q prevented the small punctate structures from forming large conglomerates of 109QmHtt.

The small aggregates were tracked for 24 hours using live cell imaging. As expected, multiple small punctuates within one cell fused with each other with time, and eventually formed one dominant or several large aggregates. 8R10Q or 8R15Q treatment rendered these punctuates unchanged throughout the observation time period.

Figure 4:
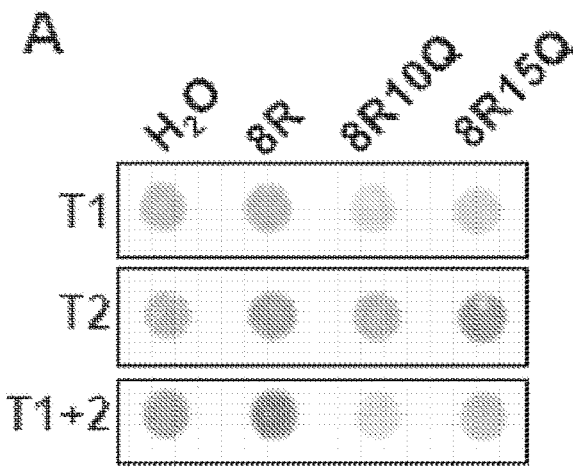
FIG. 4. Testing the ability of therapeutic peptides to decrease mHtt aggregation in Neuro2a cells overexpressing mHtt. Panel A: Filter trap assays and corresponding quantitation of cells (panel B) treated as indicated at 8 hours (T1), 24 hours (T2), or both (T1+2) after transfection with the 109QmHtt construct. Both 8R10Q and 8R15Q significantly decreased mHtt aggregates when treated at T1 or both time points, but not at T2 alone. Panel C: Western blots and quantitation (panel D) of RIPA-soluble (sol) and -insoluble (ins) fractions of Neuro2a cells overexpressing 25QHtt or 109QmHtt and treated as indicated. The levels of 109QmHtt in both the soluble and insoluble fractions were significantly decreased by 8R10Q. Panel E: Western blot of the 109QmHtt in cells treated as indicated. Note that MG132 blocked the effect of 8R10Q peptide with respect to decreasing insoluble 109QmHtt. Panel F: Quantitation of ratio of 109QmHtt in cells treated MG132 (+) over DMSO (−) in relationship to peptides. Statistical analysis conducted with one way ANOVA, *$<0.05$, $<0.01$, *$<0.001$, ns: not significant.
Figure 4:
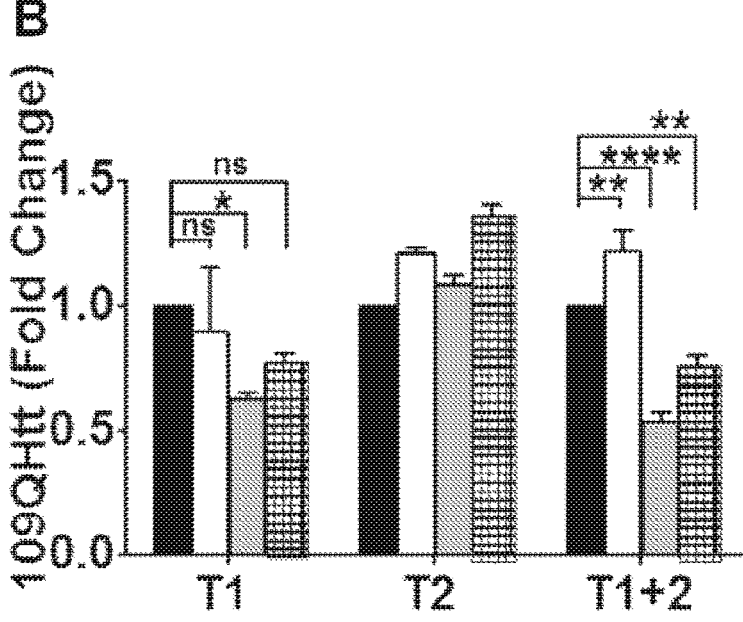
Figure 4:
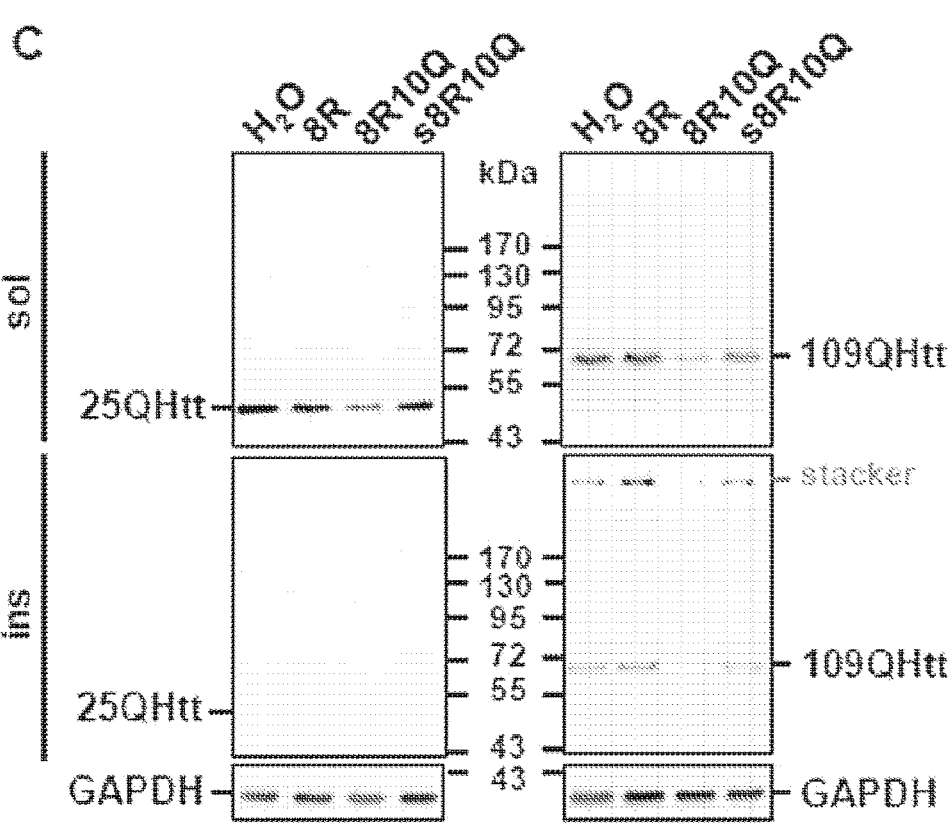
Figure 4:
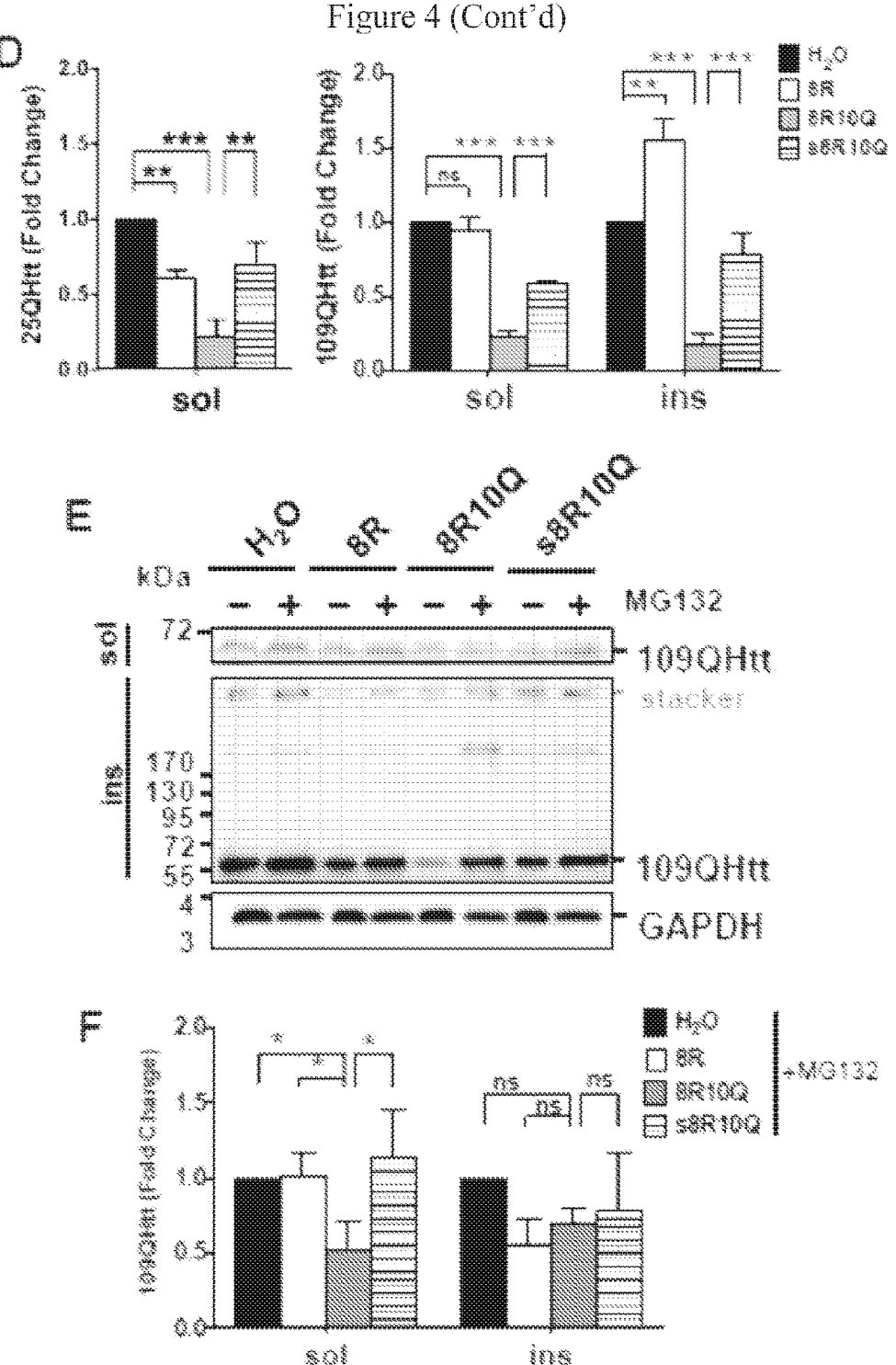

Whether the peptides could modulate the aggregation propensity of mHtt was next investigated. As shown in FIG. 4, panels A and C, 20 μM of peptide 8R10Q or 8R15Q, added at 8 hours (T1) or 8 plus 24 hours (T1+T2) after transfection significantly reduced the aggregated 109QmHtt as compared with water or the 8R peptide control by filter trap assay. However, when the peptide was added at 24 hours alone, no obvious effects were observed. These results showed that 8R10Q and 8R15Q peptides effectively prevented the mHtt from aggregation.

For further characterization, Neuro2a lysates were separated into the RIPA-soluble (sol) and insoluble (ins) fractions (FIG. 4, panel B). 8R10Q peptide decreased the level of mHtt in both the soluble and insoluble fractions as compared with water, 8R, or the scrambled (s8R10Q) control (FIG. 4, panel D). Since the ubiquitin proteasomal system (UPS) had been previously shown to be important for mHtt degradation (Martin-Aparicio, *J Neurosci* (2001) 21:8772-81; Jana, *Hum Mol Genet* (2001) 10:1049-59), MG132, an inhibitor of the UPS, was used to block the peptide-induced decrease in the mHtt. MG132 reversed the level of the 109QmHtt in the peptide group (FIG. 4, panel E). A quantitative assay showed that MG132 treatment increased the level of mHtt across all groups, indicating a basal turnover of 109QmHtt by UPS. However, the ratio of the MG132: DMSO 109QmHtt was much higher for the 8R10Q treated samples (FIG. 4, panel F). These results indicated that the peptide reduced the mHtt through enhancement of its degradation by UPS.

Figure 5:
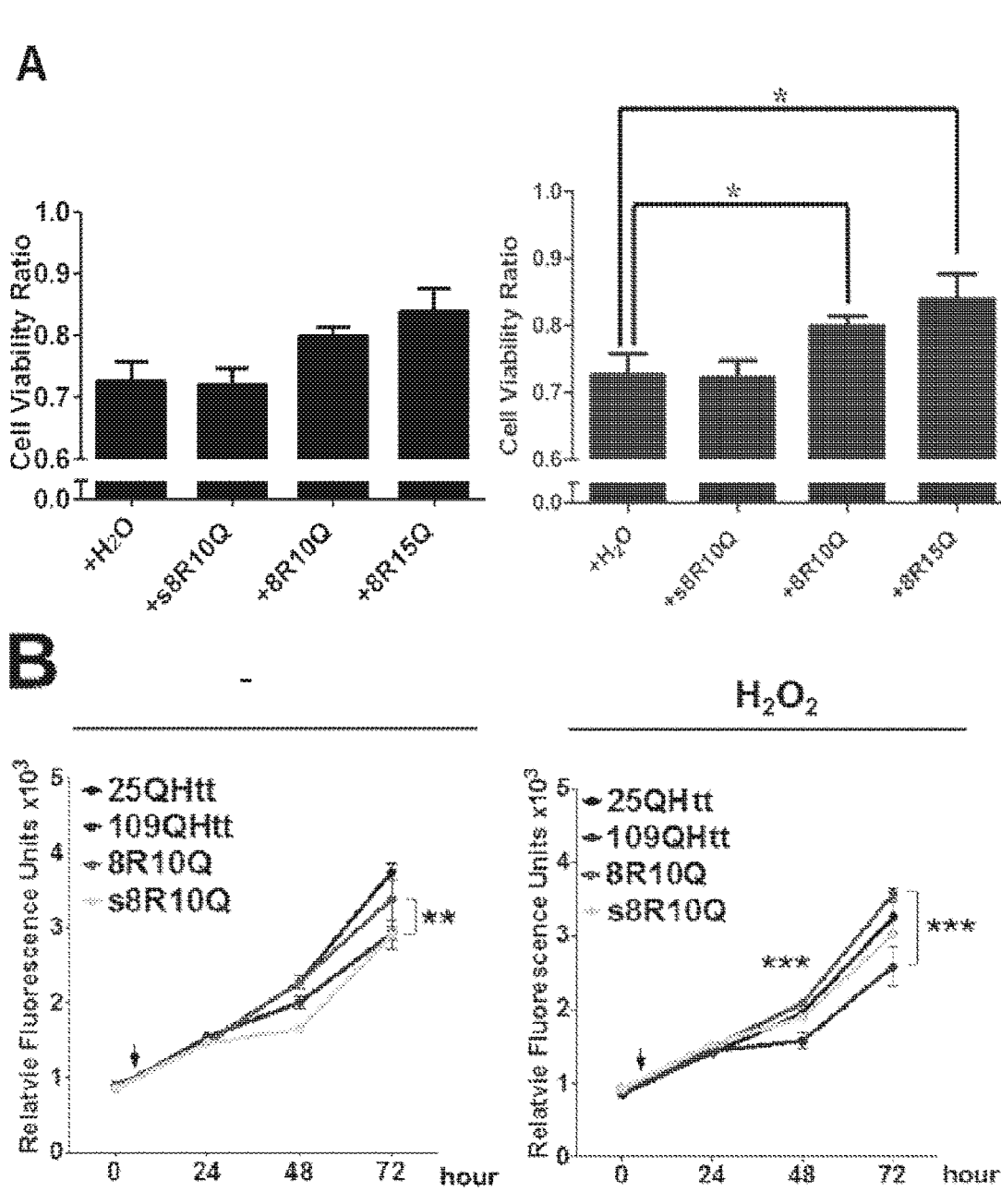
FIG. 5. Therapeutic effect of 8R10Q and 8R15Q in 109QmHtt-expressing cells. Panel A: Cell viability assay by MTT in Neuro2a cells expressing 25QHtt (left) or 109QmHtt (right) treated with $H_2O_2$ at 50 μM and the indicated peptide. Panel B: Cell growth curve of Neuro2a cells expressing 25QHtt or 109QmHtt treated with indicated peptide. The cells in right subpanel were further treated with $H_2O_2$ at 12.5 μM 16 hours after transfection. 109QmHtt cells growth was slower than that of the 25QHtt cells. 8R10Q treatment rescued the slow growth of Neuro2a cells by 109QmHtt with or without $H_2O_2$. Panel C: Micrographs of the phase contrast and fluorescent images of retinoic acid-differentiated Neu2a cells expressing GFP-25QHtt or GFP-109QmHtt (GFP) treated with the indicated peptide. Note the neurites of the differentiated cells. Panel D: Quantitation of the percentage of differentiated cells with neurites. Fewer 109QmHtt-expressing cells had neurites vs. 25QHtt-expressing cells. 8R10Q treatment could significantly rescue the defect in neurite outgrowth. The experiments were conducted in triplicate and repeated twice. Statistical analysis was performed with one way ANOVA, *$p<0.05$; $p<0.01$; *$p<0.001$, ns: not significant.
Figure 5:
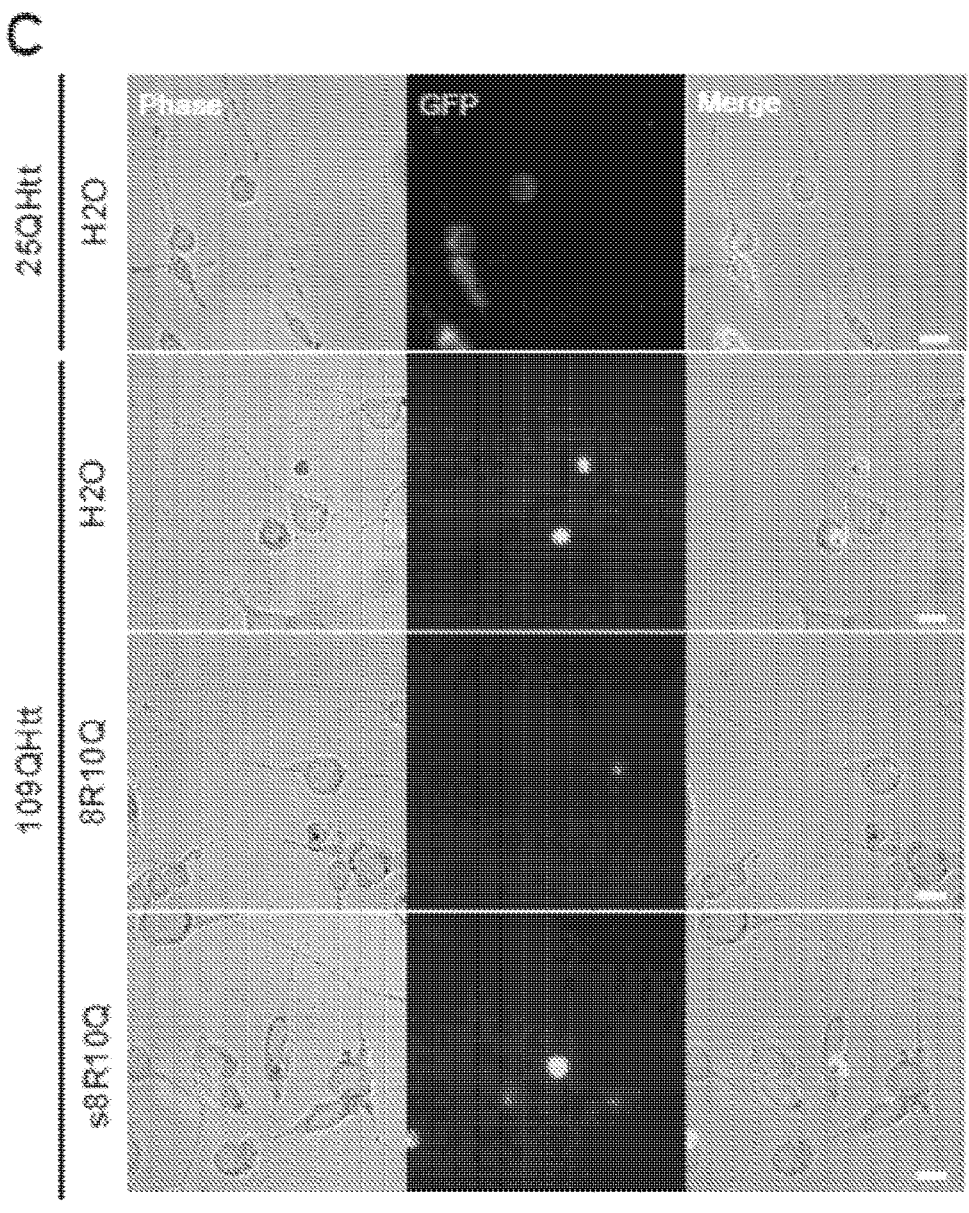
Figure 5:
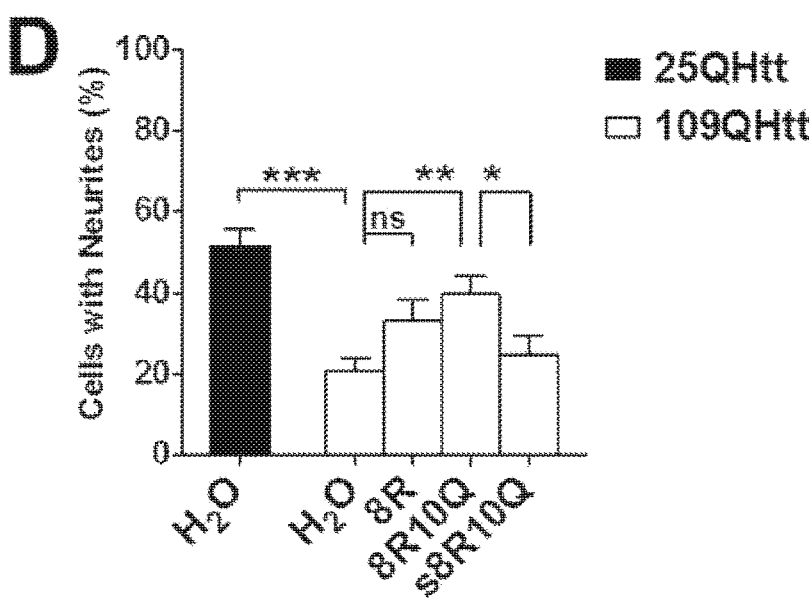

Protection of Cells Against the Neurotoxicity of 109QmHtt and $H_2O_2$ by Bipartite Peptides It has long been reported that HD patients have higher levels of oxidative stress linked with mitochondrial dysfunction induced by mHtt. Browne, Brain *Pathol* (1999) 9:147-63; and Tasset, *Revista de Neurologia* (2009) 49:424-9. mHtt and oxidative stress may form a self-reinforcing vicious cycle in HD. In the present study, approximately 83% of Neuro2a cells expressing 25QHtt treated with 50 μM $H_2O_2$ with or without scrambled or bipartite therapeutic peptides survived (FIG. 5, panel A). On the other hand, the survival rate of Neuro2a cells expressing 109QmHtt decreased to ~72%, indicating that the 109QmHtt rendered cells more vulnerable to the oxidative stress of $H_2O_2$. 8R10Q or 8R15Q treatment increased the survival rate to levels above 80% (FIG. 5, panel A).

The expression of 109QmHtt reduced the growth of Neuro2a cells, and so did the lower levels of $H_2O_2$ (12.5 μM) (FIG. 5, panel B). Peptide 8R10Q ameliorated the reduction in growth induced not only by the toxicity of 109QmHtt, but also by $H_2O_2$, as compared with 8R or the scrambled control.

Retinoic acid (RA) induced the differentiation of Neuro2a cells with neurite outgrowth. 109QmHtt decreased the number of cells bearing RA-induced neurites relative to 25QHtt (FIG. 5, panels C and D). 8R10Q treatment significantly reversed the defect in neurite outgrowth caused by 109QmHtt as compared with water or the scrambled control. The 8R peptide also rescued the cells from this toxicity to some extent, but the results were not statistically significant.

These results clearly showed that the bipartite peptides could protect Neuro2a cells against the toxicity caused either by 109QmHtt and/or by $H_2O_2$.

Therapeutic Effect of 8R10Q on R6/2 Transgenic Mice

Figure 6:
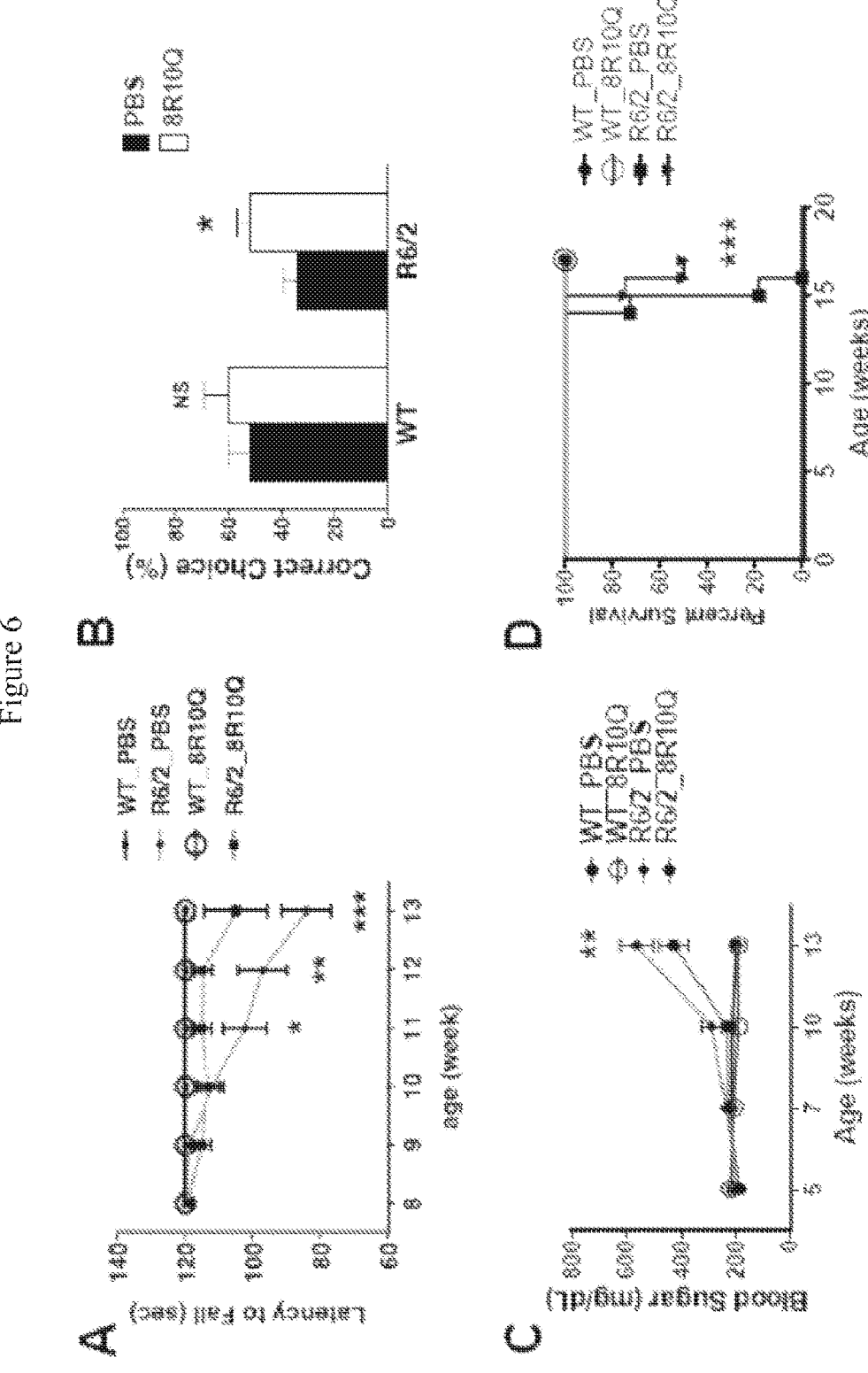
FIG. 6. 8R10Q ameliorated functional deterioration of R6/2 transgenic mice. Panel A: Longitudinal rotarod performance of wild type (WT) and R6/2 mice treated with PBS or 8R10Q peptide. Note the significant delay in motor deterioration of R6/2 mice treated with 8R10Q from 11 weeks of age. Panel B: T maze test of WT and R6/2 mice at 13 weeks of age. The 8R10Q significantly rescued the memory deficit in R6/2 mice. Panel C: The curves of blood sugar in serum of WT and R6/2 mice treated as indicated. Note 8R10Q treatment significantly decreased the rise in blood sugar in R6/2 mice. Panel D: Lifespan of WT and R6/2 mice treated with PBS vs. 8R10Q. 100% of R6/2 mice died before 16 weeks of age. 8R10Q significantly extended the lifespan of R6/2 mice. WT mice N=6/group; R6/2 mice N=10/group; statistical analysis performed with two way ANOVA (panels A and C), one way ANOVA (panel B), $*p<0.05$; $p<0.01$; $*p<0.001$, ns: not significant, and log-rank (Mantel-Cox) Test (D), $***p<0.0001$.

To test the therapeutic effect of the peptide in vivo, the 8R10Q peptide was delivered 6 days/week into the wild type (WT) or R6/2 transgenic mice through intranasal aspiration or continuously with the Alzet osmotic minipumps into the neostriatum. The body weights of the WT or R6/2 mice treated with 8R10Q through either route remained comparable to those treated with PBS. As shown in FIG. 6, panel A, the motor deterioration assessed by the rotarod of R6/2 mice became significant from 11 weeks of age, but the 8R10Q treatment effectively delayed the phenotype until 13 weeks. In fact, the 8R10Q-treated R6/2 mice performed even better than the 11 week-old PBS-treated mice on average. The 8R10Q peptide delivered intracerebrally exhibited a very similar therapeutic effect to that given intranasally. These results showed that administration route does not affect this effect. In addition, intranasal 8R10Q also corrected the memory deficit of 13 week-old R6/2 mice as shown in the T maze test (FIG. 6, panel B). The R6/2 mice were previously reported to have diabetes. Bjorkqvist et al., *Hum Mol Genet* (2005) 14:565-74; and Hunt et al., *Experimental Brain Res* (2005) 166:220-9. The intranasal administration of 8R10Q peptide delayed the rise and decreased the level of blood sugar (FIG. 6, panel C). Similarly, 8R10Q given intracerebrally also significantly corrected the diabetes phenotype. Lastly, all R6/2 mice treated with PBS died before or at 16 weeks of age; however, 8R10Q given intranasally prevented premature death by 41% at 16 weeks of age (FIG. 6, panel D). To sum up, the 8R10Q peptide effectively delayed the onset of disease and ameliorated the pathological phenotypes.

Decrease of Neuropathology by 8R10Q Peptide

Figure 7:
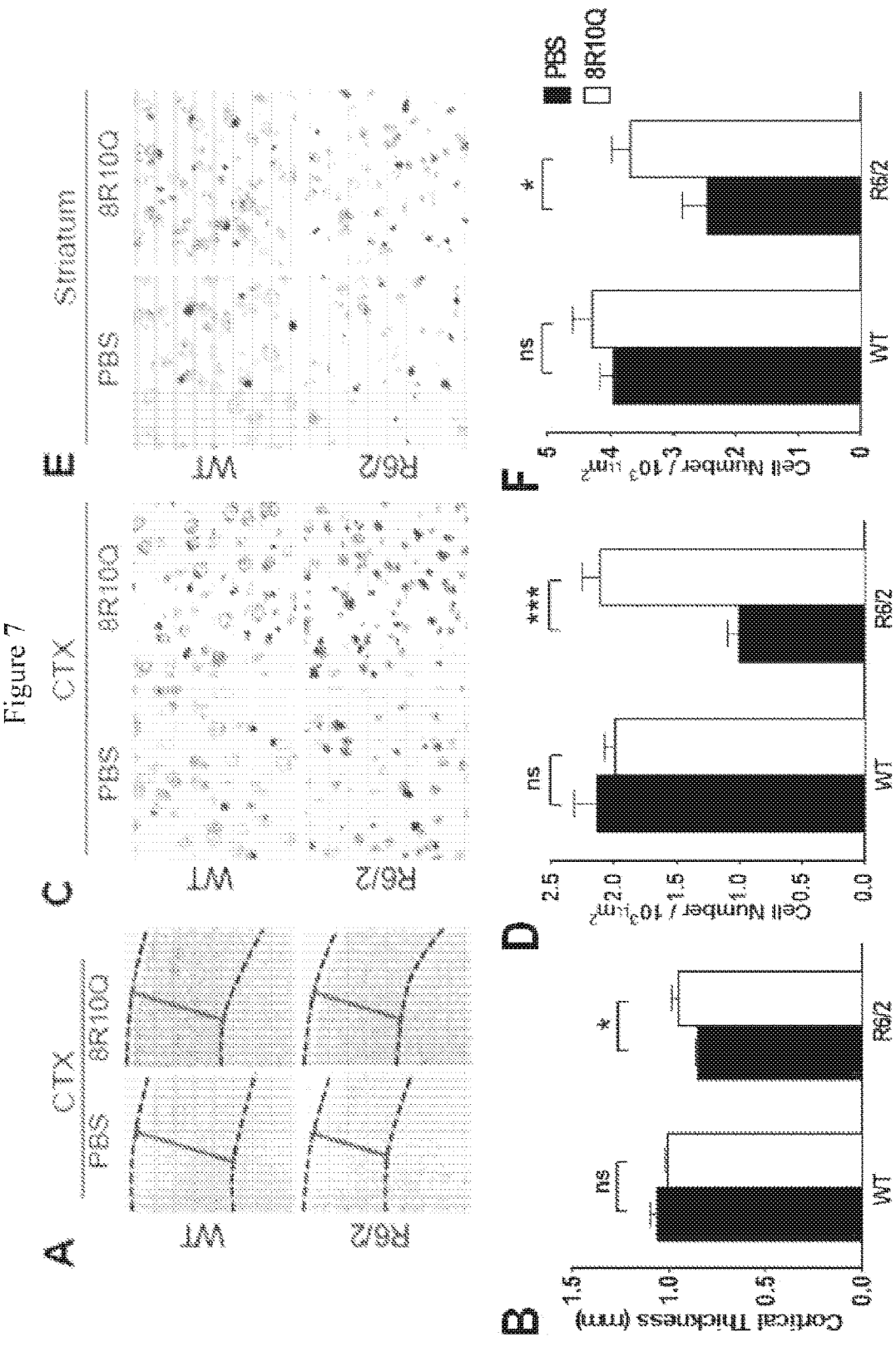
FIG. 7. Amelioration of neuronal damage of 13 week-old R6/2 mice by 8R10Q peptide. Panel A: Micrographs of the Nissl stain sections of cortex (CTX) of WT and R6/2 mice. The cortex and its thickness are highlighted by the dashed lines and red solid lines, respectively. Panel B: Quantitation of the cortical thickness. Note the decrease in cortical thickness in R6/2 mice which was reversed by the 8R10Q. Panels C and F: Micrographs (panel D) and (panel F) show the corresponding quantitation of the Nissl stained sections of the cortex and striatum, respectively. Note the decrease in the number of neurons, which was reversed by 8R10Q. N=3/group, each bar represents the average of 5 sections. Statistical analysis performed with one way ANOVA, $*p<0.05$; $***p<0.001$, ns: not significant.

R6/2 transgenic mice exhibited a decrease in cortical thickness due to the loss of cortical neurons. Interestingly, 8R10Q peptide prevented cortical thinning (FIG. 7, panels A and B), suggesting that this peptide could rescue neurons from death. Indeed, the neuronal count revealed that the loss of neurons in both the cortex (FIG. 7, panels C and D) and striatum (FIG. 7, panels E and F) of the R6/2 mice was significantly prevented by the intranasal 8R10Q treatment.

Figure 8:
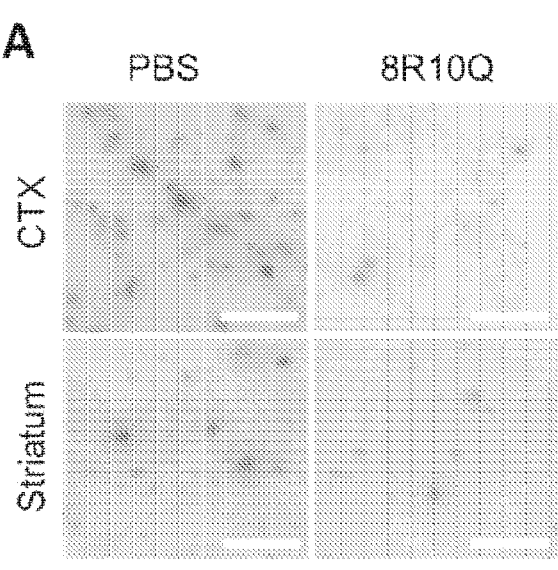
FIG. 8. Decrease in mHtt aggregates and glial pathology in 13-week-old R6/2 mice by 8R10Q peptide treatment. Panel A: Micrographs and corresponding quantitation (panel B) of the immunostained sections of cortex (CTX) and striatum with EM48 antibody. The brown dots show the mHtt aggregates. The left subpanels of panel B show the quantitative data with respect to the total area occupied by the aggregates, and the right, the intensity of individual aggregates. Panel C: Photographs of the immunofluorescent-stained sections of the cortex of R6/2 mice with anti-GFAP antibody. Panel D: Quantitation of the GFAP intensity showed a significant decrease in 8R10Q treated mice. Panel E: Micrographs of the immunostained sections of the cortex (CTX) and striatum of WT and R6/2 mice with anti-Iba1 antibody. Panel F: Quantitation of Iba1 intensity revealed an obvious increase in Iba1 immunoreactivity in R6/2 mice which was reversed by the 8R10Q. N=3/group. Each bar represented an average of 15 sections/mouse group. Statistics were performed with Student's t test for panels B and D, but with one way ANOVA, $*p<0.05$; $p<0.01$; $*p<0.001$, ns: not significant.
Figure 8:
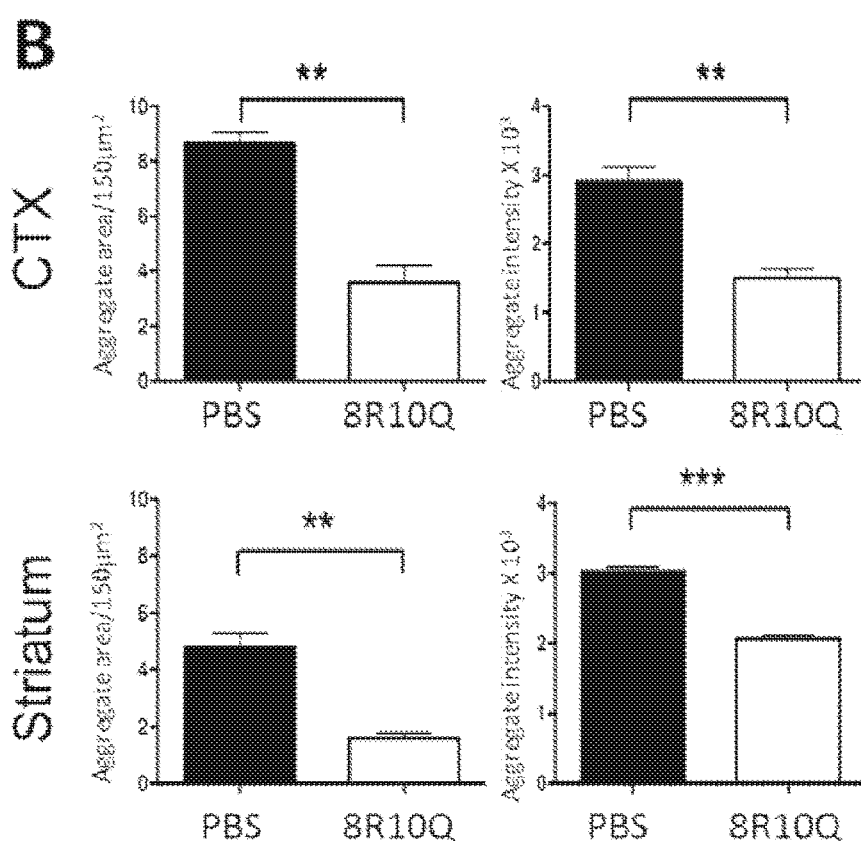
Figure 8:
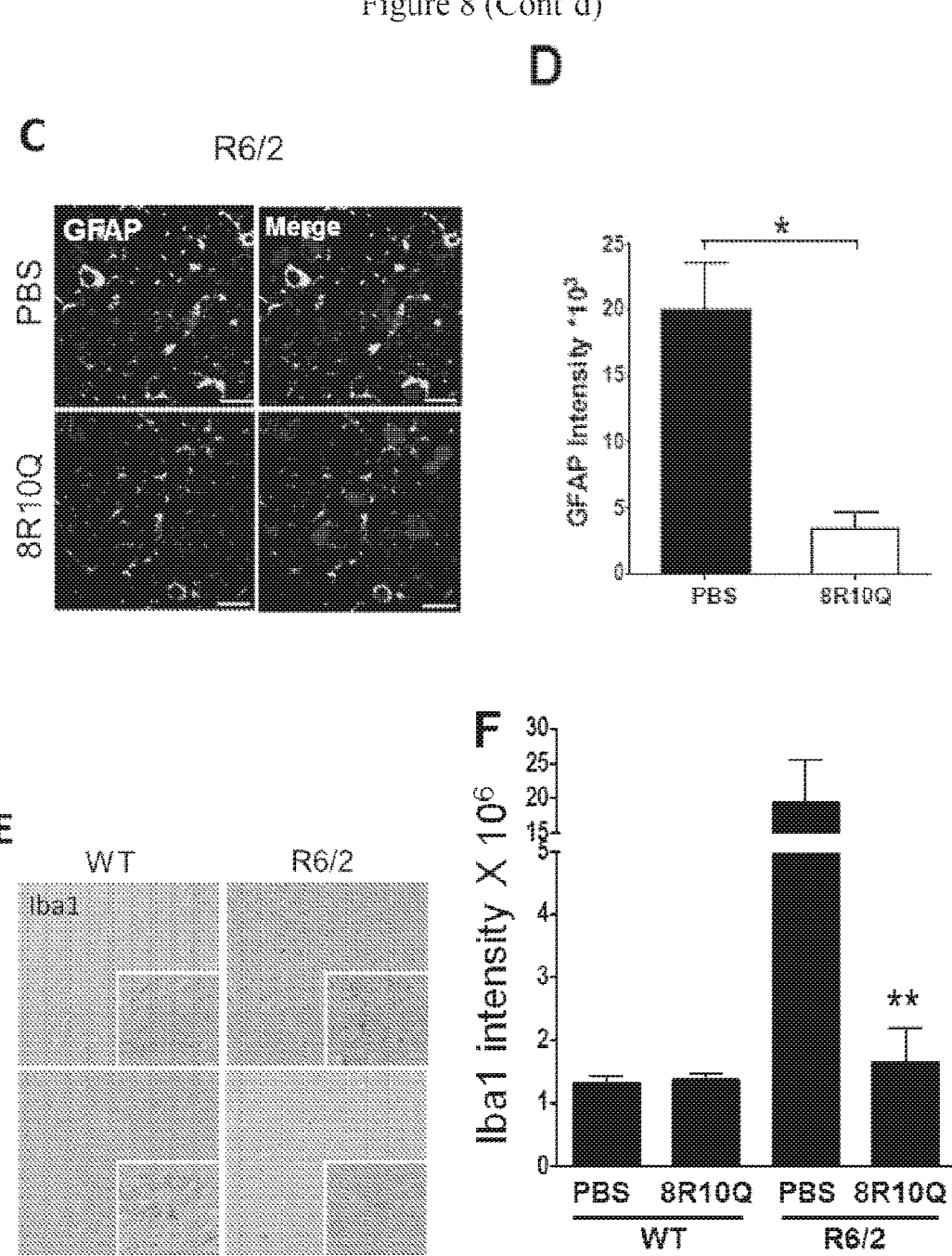
Figure 9:
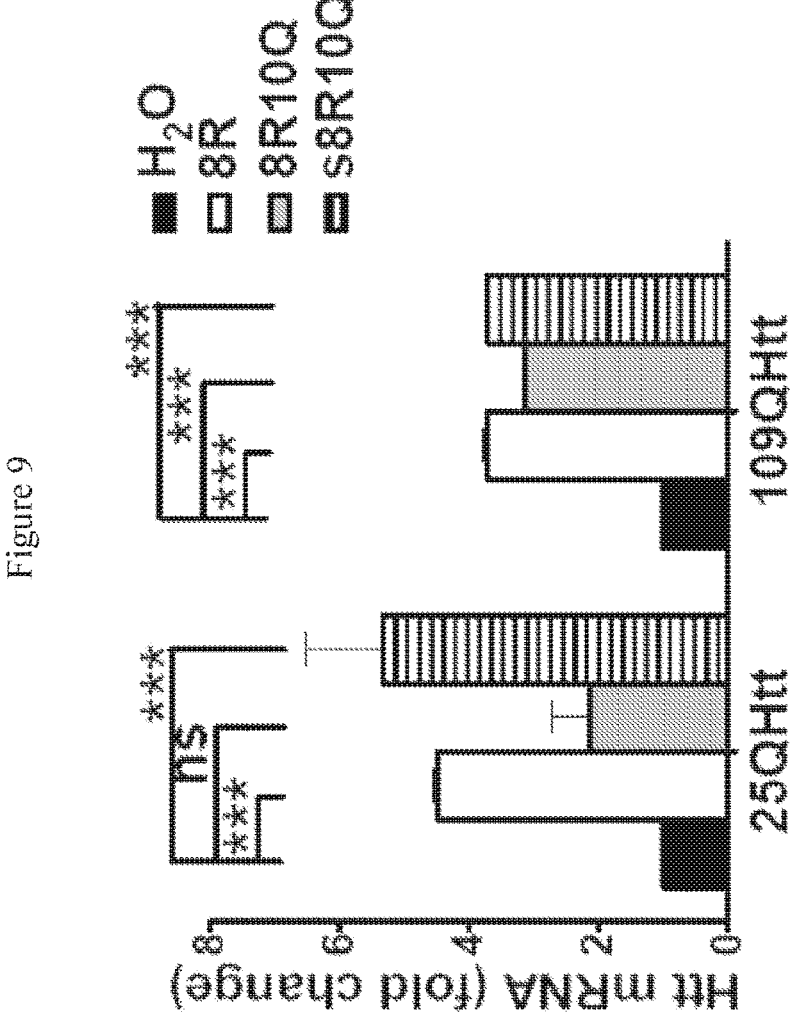
FIG. 9. Changes in the levels of Htt mRNA by quantitative RT-PCR in Neuro2a transfected with 25QHtt or 109QmHtt and treated with the indicated peptide. Statistical analysis was performed with one way ANOVA, $***p<0.001$, ns: not significant FIG. 10. Effect of the designed bipartite peptides on inhibition of fibrillization. The peptides were dissolved in 20 mM sodium phosphate buffer with 150 mM KCl (pH 7) and incubated at 25° C. CD spectra and TEM images were taken for Aβ40 (panels A and D), $R_8Aβ$ (25-35) (panels B and E), $^DR_8$-Aβ (25-35) (panels C and F), and the 1:1 mixture of $Aβ_{40}$ with $R_8$-Aβ (25-35) (panels G and J) or $^DR_8$-Aβ (25-35) (panels H and K). The CD spectra were recorded at the indicated incubation time. The TEM images were taken after prolonged incubation. Panel I: The time course of amyloidogenesis of $Aβ_{40}$ with and without the designed bipartite peptides.

To correlate the beneficial effect with the aggregates of mHtt, immunohistochemistry was performed to calculate the areas occupied by the aggregates per unit area (150 μm$^2$). The method was selected because the frequent clustering of the aggregates into conglomerates rendered an accurate count of the aggregate number very difficult. As shown in FIG. 8, panels A and B, the 8R10Q peptide decreased the areas of aggregates by ~60% in both the cortex and striatum as compared with the PBS control. In addition, the intensity which represented the amount of mHtt in the aggregates was also significantly decreased by the 8R10Q peptide in both areas. Corresponding Western blot analysis revealed that the RIPA-insoluble or aggregate fraction was decreased by the 8R10Q peptide as compared with PBS. The rescue effect with respect to the neuronal loss and aggregation was accompanied by a significant decrease in the numbers of GFAP-positive astrocytes (FIG. 8, panels C and D) and that of Iba-1-positive microglia (FIG. 8, panels E and F) in the cortex of the 8R10Q-treated R6/2 mice. Furthermore, the R6/2 mice had weak tau signals compared with the WT mice, but 8R10Q treatment significantly enhanced this in both cortex and striatum, indicating restoration of the axonal processes. Taken together, these results showed that the 8R10Q peptide effectively decreased the aggregated species of mHtt, and prevented the neurotoxicity induced by the mHtt.

DISCUSSION

In this study, bipartite therapeutic peptides like 8R10Q were shown to bind to mHtt aggregates, decrease mHtt-mediated toxicity, and delay the onset and progress of neurologic dysfunction in HD models. In addition, the therapeutic effect of 8R10Q was observed in a mouse cell line transiently expressing mHtt, R6/2 transgenic mice, and human HD iPS-derived neurons; its therapeutic effect was independent of the animal species or length of polyQ in mHtt.

In the bipartite peptide design, the charged sequence played an essential role in preventing the therapeutic peptide itself or misfolded target/peptide hybrid from aggregating. To identify peptides that may decrease mHtt toxicity, studies using various approaches, such as phage display (Kawasaki et al., *Biosci, Biotech, and Biochem* (2012) 76:762-6; Lecerf et al., *Proc Natl Acad Sci USA* (2001) 98:4764-9; Nagai et al., *Hum Mol Genet* (2003) 12:1253-9; Magai et al., *J Biol Chem* (2000) 275:10437-42) or other screening methods (Arribat et al., *PLOS One* (2013) 8: e68775; Lakhani et al., *PLOS Computational Biol* (2010) 6: e1000772; Skogen et al., *BMC Neurosci* (2006) 7:65) and sequence modifications (Lanning et al., *Biochem* (2010) 49:7108-18; Kazantsev et al., *Nat Genet* (2002) 30:367-76) have previously been conducted. Compared with those approaches, inclusion of the repulsion force by the charged sequence into peptide design provides several advantages. First, previous studies were mainly target- or disease-specific. In contrast, the present study renders designing therapeutic peptides against various neurodegenerative diseases possible by choosing a partner sequence with a specific affinity for the misfolded protein/derivative of the disease-of-interest. This possibility is supported by a separate study, which showed that therapeutic peptides designed by the same principle yielded a similar beneficial outcome in APP/PS1 transgenic mice, a widely used mouse model for AD. Second, it may significantly simplify the work spent in searching for or in modifying candidate sequences for the therapeutic peptides. Previous approaches required one to find peptides of dual functions that would both bind to the misfolded protein/derivative, and at the same time, stop the latter from aggregation, which might require a considerable amount of effort. Also, these efforts would likely need to be reinstated for a different disease. In the present design, the affinity sequences could be directly taken from the misfolded protein/derivative of the particular disease-of-interest, as already demonstrated in both of the studies. Thus, much work could be eliminated. Furthermore, the strategy may be applied to the peptides identified in the previous studies to further enhance their therapeutic effects.

Example 2: Exemplary Bipartite Therapeutic Peptides for Use in Delaying Disease Onset in APP/PS1 Transgenic Mice Adult neurodegenerative diseases (NDs) comprise a heterogeneous group of neurological disorders characterized by disease-specific inclusion bodies (IBs) formed by misfolded peptides/proteins. Alzheimer's disease (AD) is the most common ND, with signature IBs, amyloid plaques, and neurofibrillary tangles. An imbalance in the production and clearance of misfolded amyloid $\beta$ (A$\beta$) peptide and its variants is considered the primary cause for the pathogenesis of AD. A modular peptidic design combining polyarginines (PolyR) and a peptide derived from the pathogenic peptide/protein forming IBs is discussed below. The designed bipartite peptides were expected to have target-specific affinity and to be able to prevent misfolded peptide/protein self-aggregation by the charge repulsion conferred by PolyR. A designed bipartite peptide $R_8$-A$\beta$(25-35) and its D form derivative $^D R_8$-A$\beta$(25-35) were found to prevent A$\beta_{40}$ from forming amyloid fibrils by circular dichroism and electron microscopy. When mixed at a 1:1 ratio, both peptides significantly decreased the toxicity of A$\beta_{40}$ to the Neuro2a cells. Daily intranasal administration of PEI-conjugated $R_8$-A$\beta$(25-35) peptide from 4 months of age significantly ameliorated the memory deficits of the 8 month-old APP× PS1 double transgenic mice compared with PEI-treated control group as demonstrated by a Morris water maze test. The level of total A$\beta_{40}$ and A$\beta_{42}$ in the cortex and hippocampus were remarkably reduced; also, the number of amyloid plaques were consistently reduced. Taken together, the modular design combining polyR with a peptide from the pathogenic peptide/protein, like $R_8$-A$\beta$(25-35), produced desirable therapeutic effects and could be easily adopted to design therapeutic peptides for other diseases characterized by IBs.

Methods and Materials

Peptide Synthesis

The peptides were prepared by the batch fluorenyl-methoxycarbonyl (fmoc)-polyamide method. Chen et al., *Protein Sci* (2001) 10:1794-1800. The sequence of A$\beta$ 40: DAEFRHDSGYEVHHQKLVFFAEDVGSNK-GAIIGLMVGGVV (SEQ ID NO: 20). The sequence of R8A $\beta$ 25-35: RRRRRRRRGSNKGAIIGLM (SEQ ID NO: 3); $^D$R8A $\beta$ 25-35 had the same sequence as R8A $\beta$ 25-35, but the L-form arginines were replaced by D-form arginines. The C-terminal carboxyl group was amidated using Rink Amide AM resin (Novabiochem, Billerica, MA, USA) as the solid support. Fmoc-amino-acid derivatives (4 equivalents) (Anaspec, Freemont, CA, USA) were coupled on the resin (1 equivalent) using benzotriazole-1-yl-oxy-tris-pyrrolidino-phosphonium hexafluorophosphate (4 equivalents) and 4.45% (v/v) N-methyl morpholine in dimethylformamide (DMF). The Fmoc cleavage step was performed using 20% piperidine in DMF. Side-chain deprotection and peptide cleavage from the resin were performed simultaneously by stirring the resin with a mixture of 9.4 ml of trifluoroacetic acid, 0.25 ml of water, 0.25 ml of ethanedithiol, and 0.1 ml of triisopropylsilane at room temperature for 1-2 hours, then the resin was removed by passing the reaction mixture through a G2 glass funnel. The crude peptide was precipitated from the filtrate by the addition of three volumes of ice-cold methyl t-butyl ether (MTBE) and centrifugation at 2000 g for 15 minutes at 4° C., then washed twice with MTBE, and dried under a vacuum. The precipitated peptide was purified by reverse-phase HPLC using a Vydac C18 column (10 mm×250 mm) and acetonitrile-water mixtures containing 0.1% trifluoroacetic acid. Peaks were analyzed on a matrix-assisted laser desorption ionization (MALDI) mass spectrometer and those containing the desired product were lyophilized and stored at −20° C. To synthesize the PEI-conjugated peptide R8-A $\beta$ (25-35)-PEI, PEI was conjugated to the C-terminal carboxyl group of the peptide. Fmoc-Met-Wang resin (Anaspec) was used as the solid support during synthesis. To avoid interference with PEI conjugation by the N-terminal amino group, the N-terminal group of the peptide was acetylated using 4 equivalents of acetic anhydride instead of an amino acid derivative in the final synthetic step.

Circular Dichroism (CD) Spectroscopy

The peptide samples were dissolved in 75% trifluoroethanol as 1.4 mM stock solutions, then diluted into 20 mM sodium phosphate buffer with 150 mM KCl (pH 7) to a final peptide concentration of 30 μM and incubated at 25° C. After the indicated times, the samples were placed in a 1-mm cell and the CD spectra between 200 and 250 nm were recorded on a J-715 CD spectrometer (JASCO, Japan). The band width was set to 2 nm and the step resolution was 0.05 nm. Each sample was scanned twice and the recorded spectra were averaged to get the final spectrum.

Transmission Electron Microscopy

The samples were deposited on carbon-coated 300-mesh copper grids, incubated for 3 min for absorption, and then washed by water. Negative staining was carried out by staining with 2% uranyl acetate for 1.5 min. After air drying, the samples were viewed using a Hitachi H-7000 electron microscope (Hitachi, Tokyo, Japan).

Cell Viability Assay

Mouse N2a neuroblastoma cells (ATCC) were cultured in Dulbecco's modified Eagle's medium (DMEM) (HyClone, USA) supplemented with 10% fetal bovine serum (FBS; HyClone, USA) in 5% CO2 at 37° C. For the cell viability assay, the cells were harvested, suspended at a density of 350,000 cells/mL in DMEM, and 100 μL of each sample was plated in each well of a 96-well CellBIND polystyrene microplate (Corning, USA). Because the cytotoxicity experiments lasted for up to 4 days, cell proliferation was blocked using a medium without FBS. The plates were then incubated at 37° C. under 5% CO2 for 24 h to allow the cells to attach to the well. The peptides were dissolved in DMSO as 6 mM stock solutions. Five microliters of the stock solution (6 mM) was diluted with 95 μL of PBS (20 mM sodium phosphate buffer, 150 mM KCl, pH 7.0), and then the sample was immediately added to 900 μL of fresh DMEM medium to give a peptide concentration of 30 μM. To test the efficacy of the peptide inhibitor, equal volumes of Aβ40 and peptide inhibitor stock solutions were pre-mixed and then diluted into PBS to make a final concentration of 30 μM for each peptide. The diluted peptide solutions were pre-incubated for 24 h at room temperature with shaking (50 rpm) before being added to the cultures. The medium in the well of the 96-well plate was replaced with 100 μL of peptide-containing medium and the plate was incubated for 48 h. Cell viability was determined using the MTT (3-[4,5-dimethylthiazol-2-yl]-2,5-diphenyltetrazolium bromide) toxicity assay. Shearman et al., *J Neurochem* (1995) 65:218-27. Ten microliters of 5 mg/mL of MTT in PBS was added to each well, and then, after incubation for 4 h, the medium was removed and the MTT crystals were dissolved in 100 μL of 90% isopropanol, 0.5% SDS, and 40 mM HCl, and their absorption at 570 nm was measured. Cell viability was calculated by dividing the absorbance of the wells containing peptide samples by that of the wells without any added peptide. The experiment was repeated at least four times and eight replicate wells were used for each sample and control in each independent experiment.

Synthesis of PEI-Conjugated Peptide

Three milligrams of acetylated $R_8$-A β (25-35) dissolved in 2.5 mL dimethyl sulfoxide (DMSO) was slowly mixed with 150 μL 1-ethyl-3-(3-dimethylaminopropyl) carbodiimide (EDC) (600 mM in 0.1 M MES, 0.5 M NaCl, pH 6) and with 150 μL N-hydroxysuccinimide (NHS) (1200 mM in 0.1 M MES, 0.5 M NaCl, pH 6) subsequently. The reaction mixture was reacted at room temperature for 30 min with gentle shaking (70 rpm). To the mixture, 180 μL polyethylenimine (PEI) was added and reacted at room temperature overnight with gentle shaking (70 rpm). The PEI-conjugated peptide, named $R_8$-A β (25-35)-PEI, was separated from unreacted PEI and $R_8$-A β (25-35) by reverse-phase HPLC using a Vydac C18 column (10 mm×250 mm) and acetonitrile-water mixtures containing 0.1% trifluoroacetic acid. Peaks were analyzed on a matrix-assisted laser desorption ionization (MALDI) mass spectrometer and those containing the desired product were lyophilized and stored at −20° C.

Intranasal Administration

APP×PS1 transgenic mice (B6C3-Tg (APPswe, PSEN1dE9) 85Dbo/Mmjax, purchased from Jackson Laboratories (USA), were bred and genotyped following the vendor's protocols. Borchelt et al., *Neuron* (1996) 17:1005-13; and Jankowsky et al., *Biomol Eng* (2001) 17:157-65. The mice had access to food and water ad libitum and were kept on a 12:12 h light-dark cycle. PEI and R8A β 25-35-PEI were dissolved in 100 mM $NaH_2PO_4$/138 mM KCl (pH 5) to a final concentration of 400 μM. For intranasal administration, 2.5 μL PEI or $R_8$-A β (25-35)-PEI was given to each nostril of one mouse when they were 3 months of age for six days/week until they were 8 months of age. Mice were then tested with a Morris water maze. Treatment were resumed after a 6-week break for the water maze test, and continued until the mice were 12 months of age.

ELISA Assays for Total Aβ40 and Aβ42

The levels of Aβ40 and Aβ42 in mouse brain homogenate were detected using ELISA kits (Invitrogen, MD, USA) according to the manufacturer's instructions. Briefly, the cortical or hippocampal tissue was weighed and homogenized at 4° C. in the cell extraction buffer provided in the kit, supplemented with protease inhibitor cocktail (Sigma, St. Louis, USA). The homogenates were then centrifuged in Eppendorf tubes at 13000 rpm at 4° C. for 10 min and the concentration of proteins in the supernatant was measured using the microBCA protein assay (Thermo, IL, USA). The APP levels were adjusted in accordance with the protein levels.

ELISA Assays for Insoluble Aβ40 and Aβ42

Half of the frozen cortical and hippocampal tissue samples were homogenized in 1 mL tapered tissue grinders in 400 μL of ice-cold TBS containing a protease inhibitor cocktail (P8340, Sigma). The homogenates were then transferred to 1.5 mL Eppendorf tubes and centrifuged at 20000 g for 20 min at 4° C. The supernatant contained soluble Aβ, whereas the TBS-insoluble pellet contained insoluble Aβ proteins. The TBS-insoluble pellet was suspended in 70% formic acid, sonicated for 1 min, and then centrifuged at 20000 g for 20 min at 4° C. The final supernatant containing the solubilized Aβ was removed and neutralized with 20 volumes of 1M Tris base. The protein concentrations of the samples containing the solubilized "insoluble" Aβ was quantified using the Bradford protein assay (Bio-Rad #500-0006).

Morris Water Maze Task

The maze was made of white opaque plastic with a diameter of 120 cm and contained 40 cm high walls. It was filled with milk/water at 25° C. A small escape platform (10×6.5×21.5 cm) was placed at a fixed position in the center of one quadrant, 25 cm from the perimeter, and was hidden 1 cm beneath the water's surface. The room contained a number of fixed visual cues on the walls. The acquisition trial phase consisted of 5 training days (Days 1-5) and four trials per day with a 15 min inter-trial interval. Four points equally spaced along the circumference of the pool (North, South, East, and West) served as the starting positions, which were randomized across the four trials daily. If an animal did not reach the platform within 90 s, it was guided to the platform, where it stayed for 15 s. The path length and escape latencies were recorded (n=10 per group). Acquisition data, such as time taken to reach the escape platform and path length were analyzed by two-way repeated measures ANOVA. On Day 5, after finishing three trials, a probe trial was performed in order to assess the mouse's spatial memory. The platform was removed from the maze and animals were allowed to swim freely for 90 s and the swimming path was recorded and analyzed.

Cytometric Bead Array

A cytometric bead array (CBA, mouse inflammation kit; BD Biosciences) was used to quantitatively measure cytokine expression levels in the control and treated mouse brain tissue lysates. CBA was also performed to measure the cytokines from different brain regions (cortex and hippocampus). This method quantifies soluble particles, in this case, cytokines, using a fluorescence-based detection mechanism. The beads, coated with the desired cytokine, IL-6 and IL-1B, reacted with the test lysates and standards, to which fluorescence dyes were then added. The assay was performed according to the manufacturer's instructions and analyzed on the FACS Calibur (Becton Dickinson). Analysis was performed using CBA software that allows the calculation of cytokine concentrations in unknown samples. Soldan et al., *J Neuroimmunol* (2004) 146:209-15.

Thioflavin S Staining

The mice were perfused with ice-cold PBS (136.89 mM NaCl, 2.68 mM KCl, 1.62 mM $KH_2PO_4$, and 10.14 mM $Na_2HPO_4$, pH 7.4) buffer and 4% paraformaldehyde (PFA)/PBS. Brains of the perfused mice were then post-fixed in 4% PFA/PBS with gentle shaking in a cold room for another 24 hours. Post-fixation, the brain samples were washed with PBS buffer and preserved in a 70% ethanol solution. PFA-fixed brain tissues were dehydrated by a semi-enclosed benchtop tissue processor (Leica TP1020). Paraffin blocks containing the dehydrated brain samples were prepared by a Leica EG1150 H. Coronal sections with 5 μm thickness were cut on a microtome (Leica RM2235). Two brain sections were transferred with a brush, put onto the surface of a water bath, floated onto the surface of clean glass slides, and placed on a 34° C. warming block for several hours. Paraffin slides were deparaffinized and rehydrated with xylene, absolute ethanol, 95% ethanol, 70% ethanol, and water, sequentially. Rehydrated slides were given 1% (w/v) thioflavin S (ThS) solution for 10 min at room temperature while protected from light. The slides were washed with 80% ethanol and water to remove excess ThS and to facilitate visualization. ThS-positive signals were then visualized with a fluorescence microscope equipped for evaluation of green fluorescence, and the plague number, plague area, and plague size were analyzed by ImageJ.

Radiosynthesis of [$^{11}$C] PIB

The radiosynthesis of [$^{11}$C] PIB was performed by using [$^{11}$C] methyltriflate according to the method described previously with minimal modification. Takalo et al., *Am. J. Neurodeger. Dis.* (2013), 2:1-14. Briefly, [$^{11}$C] methyl bromide was produced by the multi-pass bromination of [$^{11}$C] methane. Subsequently, [$^{11}$C] methyl bromide was eluted from a trap and converted to [$^{11}$C] methyltriflate by passing through a preheated silver triflate column. [$^{11}$C] methyltriflate was carried by a helium stream (20 ml/min) into 350 μl of anhydrous methylethylketone containing 1.5 mg of 2-(4'-aminophenyl)-6-hydroxybenzothiazole. After the trapping was finished, the reaction mixture was heated at 75° C. for 2 min and then 0.4 ml of the HPLC mobile phase was added to the reaction mixture for HPLC purification. HPLC purification was performed on a Waters Bondapak column (10 m, 7.8 mm ID×300 mm) using a mobile phase of acetonitrile/0.01M $H_3PO_4$ (40/60) at a flow rate of 5.0 ml/min. The radioactive fraction corresponding to [$^{11}$C] PIB was collected in a bottle containing 30 ml of pure water and passed through a C18 Sep-Pak Plus cartridge, then washed with 10 ml of pure water, eluted with 1 ml of ethanol and 10 ml of sterile normal saline, and passed through a 0.22 μm sterile filter for quality analysis and animal experiments. Radiochemical purity was greater than 99%, as determined by analytical HPLC. The specific activity was 152±52 GBq/μmol at the end of the synthesis.

In Vivo Small-Animal Positron Emission Tomography Imaging

All PET scans were performed using Triumph pre-clinical tri-modality (LabPET/X-SPECT/X-O CT) imaging system (TriFoil Imaging, USA), which provides 31 transaxial slices 1.175 mm (center-to-center) apart, a 100 mm transaxial FOV, and a 37 mm axial FOV for the LabPET sub-system. The digital APD detector technology delivers high spatial resolution better than 1 mm and a high recovery coefficient. Before the scans, all of the mice were kept warm with a heating lamp. After induction with 2.0% isoflurane, the mice were placed with their heads in the center of the field of view and were fixed in the prone position. A 20 min static data acquisition was performed in the 3D list mode with an energy window of 350-650 keV at 20 min following a [$^{11}$C] PIB (36.7±2.6 MBq; volume <0.25 ml) injection via the tail vein. The emission data were normalized and corrected for the tracer decay time. All list mode data were sorted into 3D sinograms, which were then single-slice Fourier rebinned into 2D sinograms. Summation images from 20 to 40 min after the [$^{11}$C] PIB injection was reconstructed using a MLEM algorithm, and the resulting image volume consisted of 240×240×31 voxels, with voxel size of 0.25×0.25×1.175 $mm^3$.

PET Data Analysis

All imaging data were processed and analyzed with PMOD 3.5 software package (Pmod Technologies, Zürich, Switzerland). The PET image dataset were converted to an absolute measure of radioactivity concentration (kBq/cc) using a phantom-derived calibration factor before being normalized to the injected dose (ID) of [$^{11}$C] PIB and the body mass of the animal. This normalization enabled the comparison of the brain radioactivity concentration of animals of different weights. Static PET images were co-registered with a mouse T2-weighted MRI brain atlas based on PMOD as an anatomic reference. Image origins were set to Bregma (0, 0) according to the MRI atlas and the atlas was used for VOI definition. [$^{11}$C] PIB uptake was evaluated in the 4 regions of interest, namely: the cortex, the hippocampus, the amygdala, and the olfactory bulb. Standardized uptake values (SUV) were obtained for each VOI by dividing the mean [$^{11}$C] PIB activity by the injection dose and the body weight (gram in grams). Thereafter, regional [$^{11}$C] PIB uptake in the target region was normalized by [$^{11}$C] PIB uptake in the cerebellum which was taken as the reference region (ratio to cerebellum). Manook et al., *PLOS One* (2012) 7: e31310; Poisnel et al., *Neurobiol Aging* (2012) 33:2561-71.

Results

Affinity Plus Charge Modular Design for Therapeutic Peptides

A rational design to synthesize therapeutic peptides that might reduce toxic misfolded protein/derivative across various neurodegenerative diseases was proposed. The design was built on a principle of modular assembly of sequences with affinity and charge. The conjectured peptide was composed of an affinity sequence derived from the self-aggregating region of the misfolded protein/derivative flanked on one side or both sides by a stretch of charged amino acids. The rationale behind this design was that the affinity sequence would facilitate the binding of therapeutic peptides to the misfolded protein/derivative because of its propensity to aggregate; the charged sequence would then prevent the therapeutic peptide itself and the misfolded protein/peptide hybrid from aggregation by the repulsion force of charges (FIG. 1). Theoretically, an amino acid with either a positive or negative charge could achieve the goal. In the present design, positively charged arginine was chosen because polyarginine (poly-Arg) had been shown to facilitate the penetration of therapeutic peptides into the cytoplasmic and nuclear compartments of target cells or organs. Mitchell et al., *J Pept Res* (2000) 56:318-25.

Conformational study of $A\beta_{40}$, $R_8$-$A\beta$(25-35), and $^D R_8$-$A\beta$(25-35)

Polyethylenimine (PEI) cationized proteins can transduce across cell membranes. Futami et al., *J Biosci Bioeng* (2005) 99:95-103; Futami et al., *Expert Opin Drug Discov* (2007) 2:261-9; Kitazoe et al., *J Biochem* (2005) 137:693-701; Kitazoe et al., *Biotechnol J* (2010) 5:385-92; Murata et al., *J Biochem* (2008) 144:447-55; Murata et al., *J Biosci Bioeng* (2008) 105:34-8. PEI is protease resistant and has higher charger density than a poly-Arg or poly-lysines fragment. PEI-conjugated green fluorescent protein could pass through the blood-brain barrier, and enter into brain by intranasal administration. Loftus et al., *Neurosci* (2006) 139:1061-7.

Figure 10:
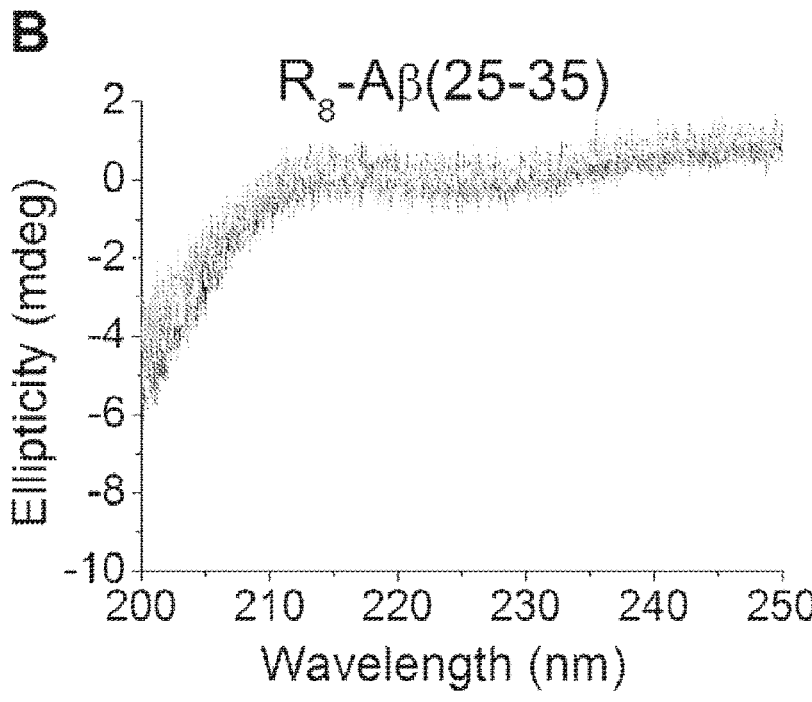
Figure 10:
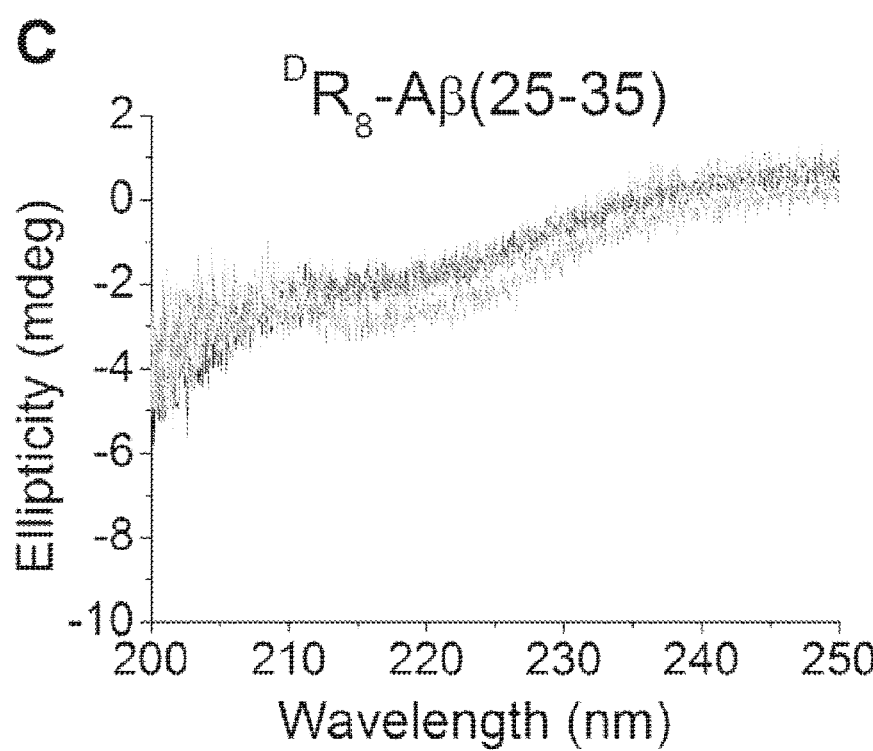
Figure 10:
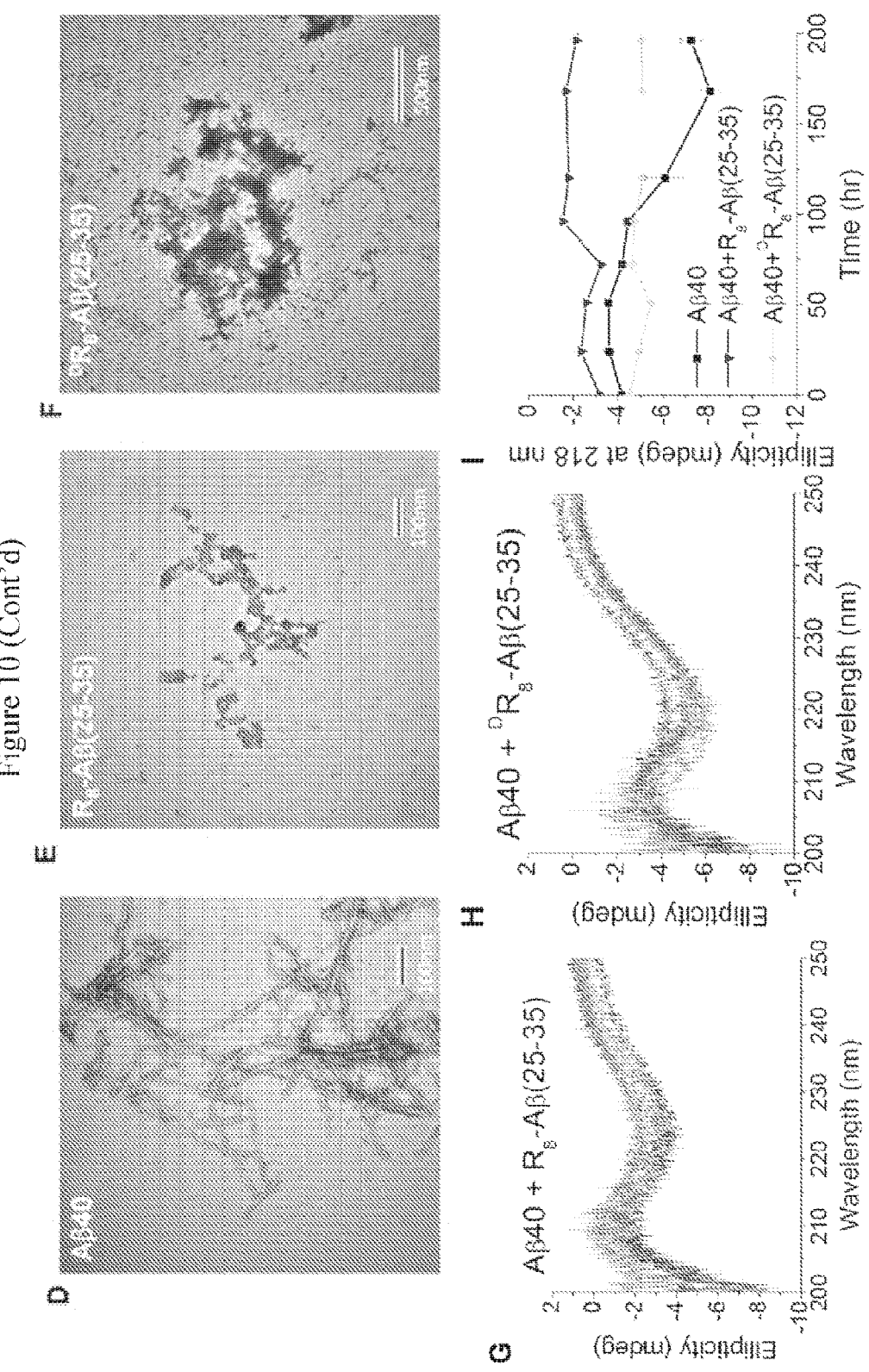
Figure 10:
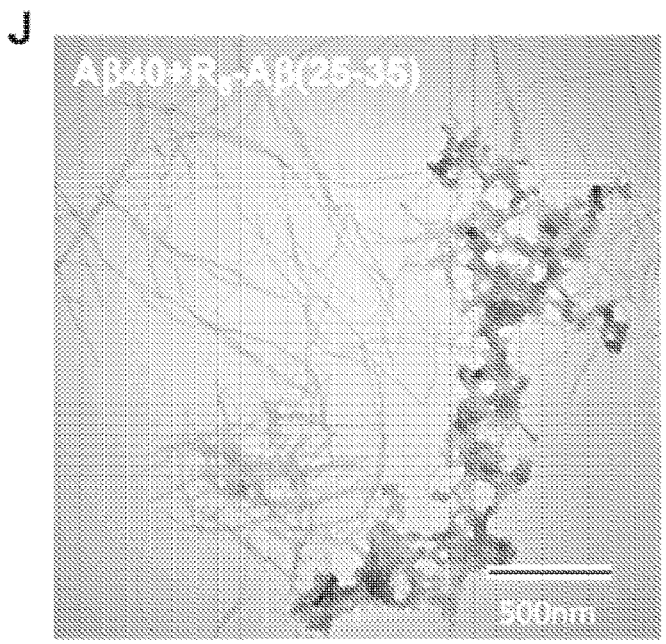
Figure 10:
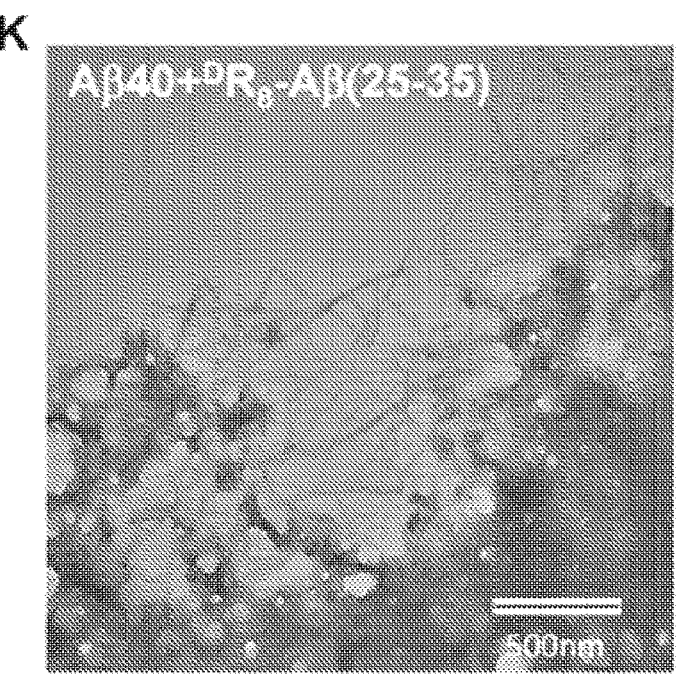

To investigate the biophysical property of these peptides concerning amyloid formation, $A\beta_{40}$, $R_8$-$A\beta$(25-35), and $^D R_8$-$A\beta$(25-35) dissolved in 20 mM sodium phosphate buffer with 150 mM KCl (pH 7) were individually incubated at 25° C. The circular dichroism (CD) spectra were recorded at various time points as indicated. As expected, the intensity of the negative ellipticity at 218 nm of $A\beta_{40}$ spectrum increased with time (FIG. 10, panel A), consistent with its known ability to form amyloid fibrils as shown by the transmission electron microscopy (TEM) (FIG. 10, panel D). In contrast, the CD spectra of $R_8$-$A\beta$(25-35) showed negative ellipticity at 200 nm, indicative of random coil structure (FIG. 10, panel B). Similarly, the $^D R_8$-$A\beta$(25-35) also had CD spectra consistent with random coil structure, which lacked strong negative ellipticity at 200 nm due to the presence of eight D-form arginines in the peptide (FIG. 10, panel C). The CD spectra of both peptides remained largely unchanged with the incubation time. The TEM showed that $R_8$-$A\beta$(25-35) and $^D R_8$-$A\beta$(25-35) formed amorphous aggregates in the same condition (FIG. 10, panels E and F). No amyloid fibrils were observed.

To examine whether $R_8$-$A\beta$(25-35) or $^D R_8$-$A\beta$(25-35) could interfere with the amyloidogenesis of $A\beta_{40}$, the CD spectra of $A\beta_{40}$ mixed with $R_8$-$A\beta$(25-35) or $^D R_8$-$A\beta$(25-35) at a 1:1 ratio were measured. As shown in FIG. 10, panels G and H, the signal at 218 nm is hardly changed when $R_8$-$A\beta$(25-35) or $^D R_8$-$A\beta$(25-35) co-incubated with $A\beta_{40}$. The kinetic traces of amyloidogenesis in FIG. 10, panel I suggested that the existence of $R_8$-$A\beta$(25-35) or $^D R_8$-$A\beta$(25-35) largely increase the lag time. After long time incubation, the TEM images of the peptide mixtures showed hybrids of fibrils and amorphous aggregates (FIG. 10, panels J and K). These results showed that $R_8$-$A\beta$(25-35) and $^D R_8$-$A\beta$(25-35) could interact with $A\beta_{40}$ and interfere with its self-aggregation, hence significantly delay or decrease the formation of $A\beta_{40}$ amyloid fibrils.

Attenuation of Aβ 40 Cytotoxicity by $R_8$-$A\beta$(25-35) and $^D R_8$-$A\beta$(25-35)

Figure 11:
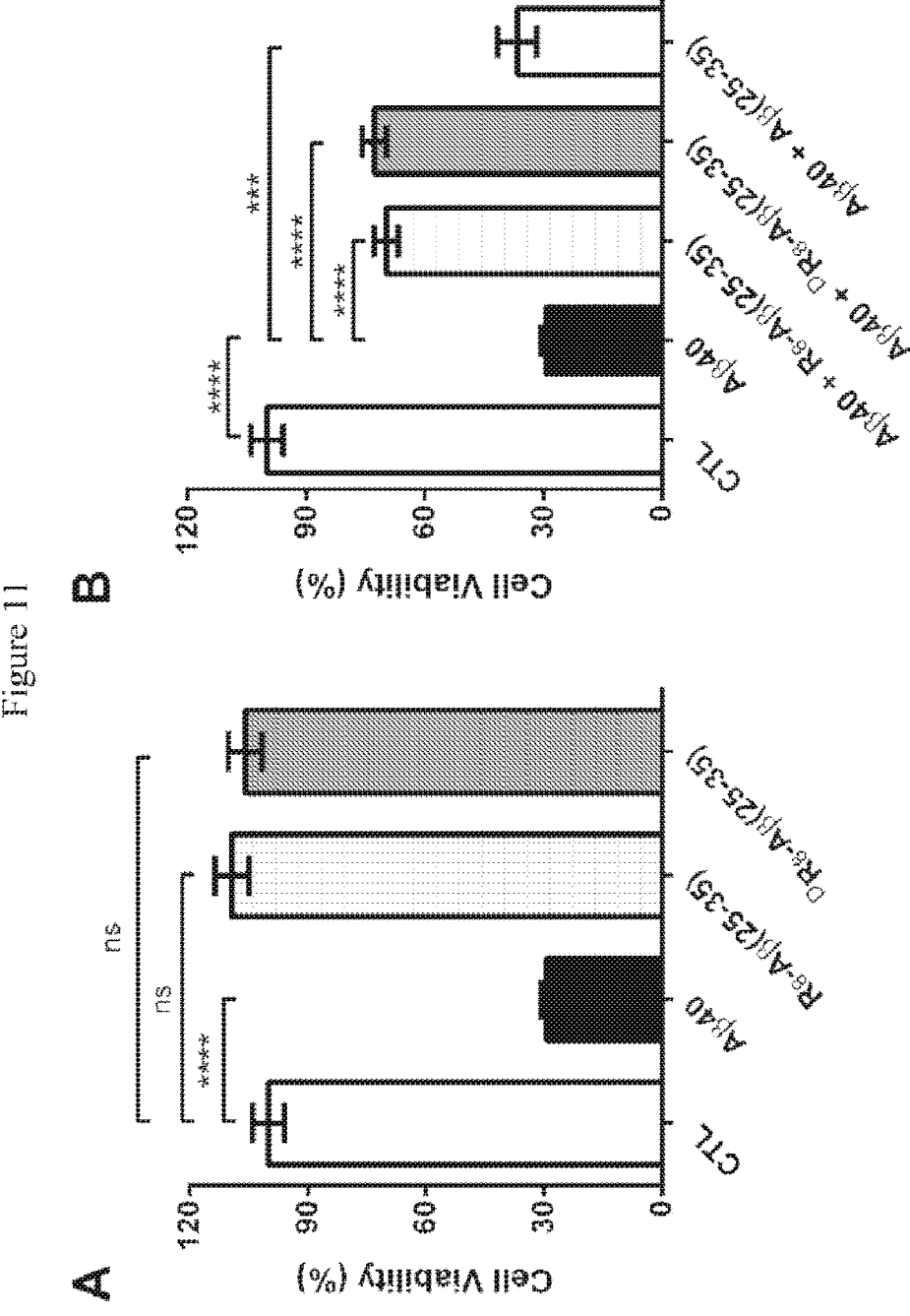
FIG. 11. Cell viability measurement by MTT assays. Panel A: Neuro2a cells treated with DMSO (control), $Aβ_{40}$, $R_8$-Aβ(25-35) or $^DR_8$-Aβ(25-35). Panel B: Neuro2a cells treated with DMSO (control), $Aβ_{40}$, and $Aβ_{40}$ with equal molar $R_8$-Aβ(25-35), $^DR_8$-Aβ(25-35), or Aβ(25-35). Each bar was generated by a triplicate experiment; the study was repeated 3 times. The statistics were performed with one way ANOVA corrected with Fisher's LSD test. $*$: $p<0.001$; $**p<0.0001$; ns, not significant.

To test whether $R_8$-$A\beta$(25-35) or $^D R_8$-$A\beta$(25-35) could attenuate the cytotoxicity of A $\beta_{40}$, the MTT assays were performed to measure the viability of Neuro2a cells (a mouse neuroblastoma cell line) treated with peptides as indicated. $A\beta_{40}$ (µM) exerted significant cytotoxicity and only 30% of cells survived. By contrast, both $R_8$-$A\beta$(25-35) and $^D R_8$-$A\beta$(25-35) had no detectable toxicity to the N2a cells (FIG. 11, panel A). Both $R_8$-$A\beta$(25-35) and $^D R_8$-$A\beta$(25-35) decreased Aβ 40 toxicity and increased the cell viability from 30% to 70-75%. For comparison, when Aβ 40 was mixed with $A\beta$(25-35), no significant change in cell viability was observed. The data showed that both $R_8$-$A\beta$(25-35) and $^D R_8$-$A\beta$(25-35) peptides had therapeutic potential in amyloid-induced toxicity.

Therapeutic Effect of $R_8$-$A\beta$(25-35) in APP/PS1 Transgenic Mice

Figure 12:
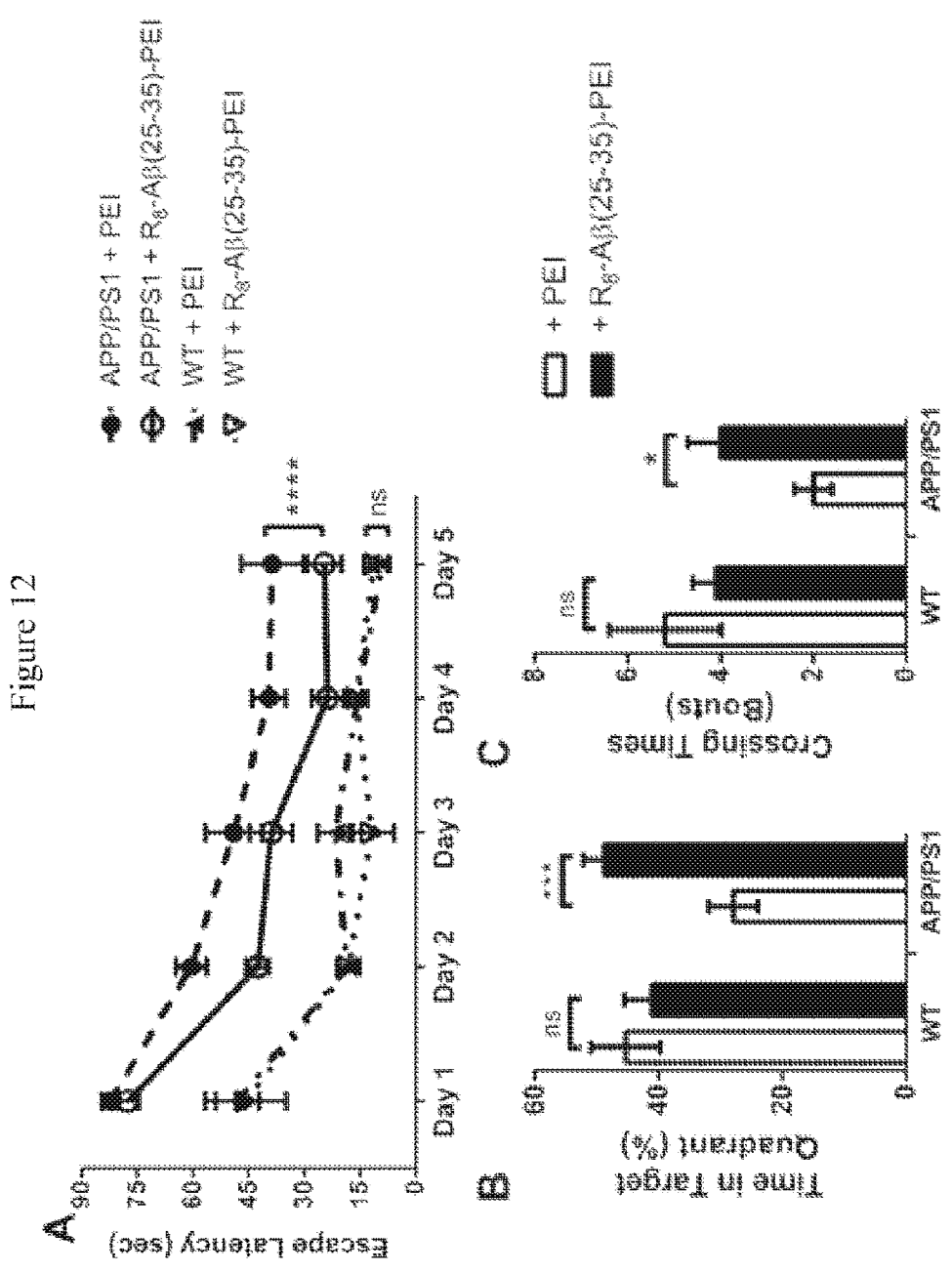
FIG. 12. $R_8$-Aβ(25-35)-PEI improved memory as measured by the Morris water maze assay. Panel A: Plot of the escape latency period of wild type (WT) and APP×PS1 transgenic (Tg) mice of 8 months of age treated with either PEI or $R_8$-Aβ(25-35) peptide from the age of 4 months to 8 months. Note a significant shortening of the latency in Tg mice by the therapeutic peptide. Panel B: Percentage of time of WT or Tg mice treated as indicated spent in swimming in the target quadrant where the hidden platform used to be. The times of the indicated mice crossing the target quadrant. $R_8$-Aβ(25-35)-PEI peptide increased the time of Tg mice in the target quadrant. Panel C: The percentage of time of the WT or Tg mice as indicated crossing the target quadrant. Ten mice per group were used in this study. The statistics were performed with two way ANOVA with Fisher's LSD post-hoc analysis. N=10/group $*<0.05$; $*<0.0005$; $<0.0001$ FIG. 13. ELISA assay for the level of Aβ40 and Aβ42 in the cortex (panel A) and hippocampus (panel B) in the 8 month-old Tg mice treated with PEI or $R_8$-Aβ(25-35)-PEI. The therapeutic peptide significantly reduced the level of both Aβ40 and $**$: Aβ42 in both regions. N=3/group; $*$: $p<0.05$; $$: $p<0.01$; $*$: $p<0.001$; $*$ $p<0.0001$; ns: not significant. Statistics by Student's t-test.

To test the effect of $R_8$-$A\beta$(25-35) to prevent the deterioration of memory in vivo, PEI or PEI-conjugated $R_8$-$A\beta$(25-35) was given intranasally to wild-type or APP/PS1 transgenic mice starting from 3-4 months of age. The water maze assay was performed when the mice reached 8 months of age. As shown in FIG. 12, panel A, the wild-type mice treated with PEI and $R_8$-$A\beta$(25-35)-PEI showed no clear difference in the learning curve of finding the hidden platform. The $R_8$-$A\beta$(25-35)-treated APP/PS1 mice, on the other hand, exhibited significantly faster learning than transgenic mice treated with PEI. In addition, $R_8$-$A\beta$(25-35) peptide-treated APP/PS1 mice performed better at the probe test evidenced by more crossings of (FIG. 12, panel C) and longer time spent in the quadrant where the probe used to be than those treated with PEI (FIG. 12, panel B).

Figure 13:
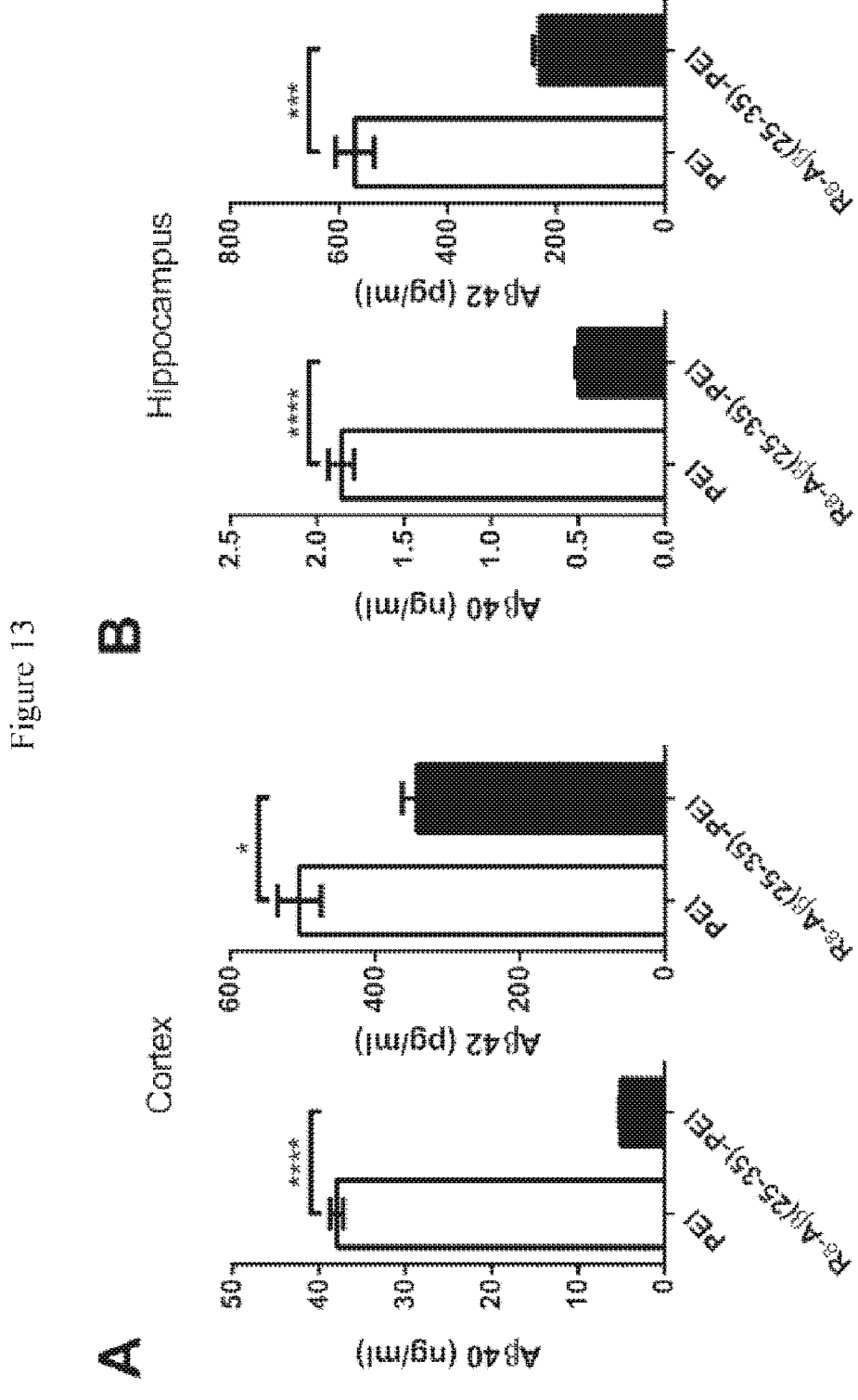

The change in the level of Aβ peptide was next examined via ELISA. As shown in FIG. 13, at 8 months of age, the level of Aβ 40 and Aβ 42 decreased by 86% and 30%, respectively in the cortex of $R_8$-$A\beta$(25-35) peptide-treated APP/PS1 mice as compared with that of PEI-treated transgenic mice. Similarly, the levels of $A\beta_{40}$ and $A\beta_{42}$ decreased by 73% and 60%, respectively in the hippocampus of the former mice compared with the latter.

Figure 14:
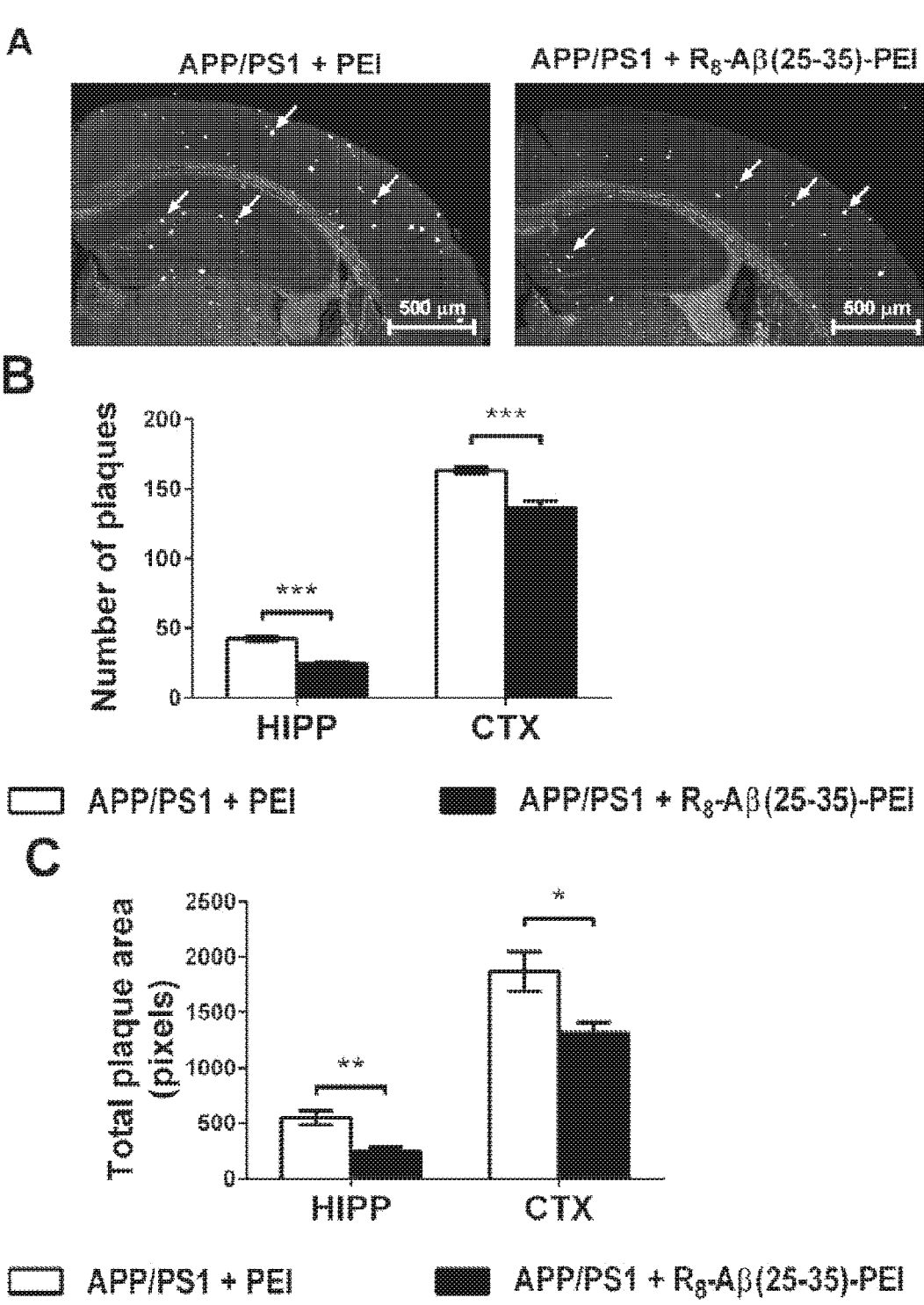
FIG. 14. Effect of intranasally delivered $R_8$-Aβ(25-35)-PEI on APP×PS1 mice on Aβ clearance after 4 months treatment. Wild type (WT) and APP×PS1 transgenic (Tg) mice were treated with either PEI or $R_8$-Aβ(25-35)-PEI from the age of 4 months to 8 months. Panels A-E show ThS-staining of the brain slices.
Figure 14:
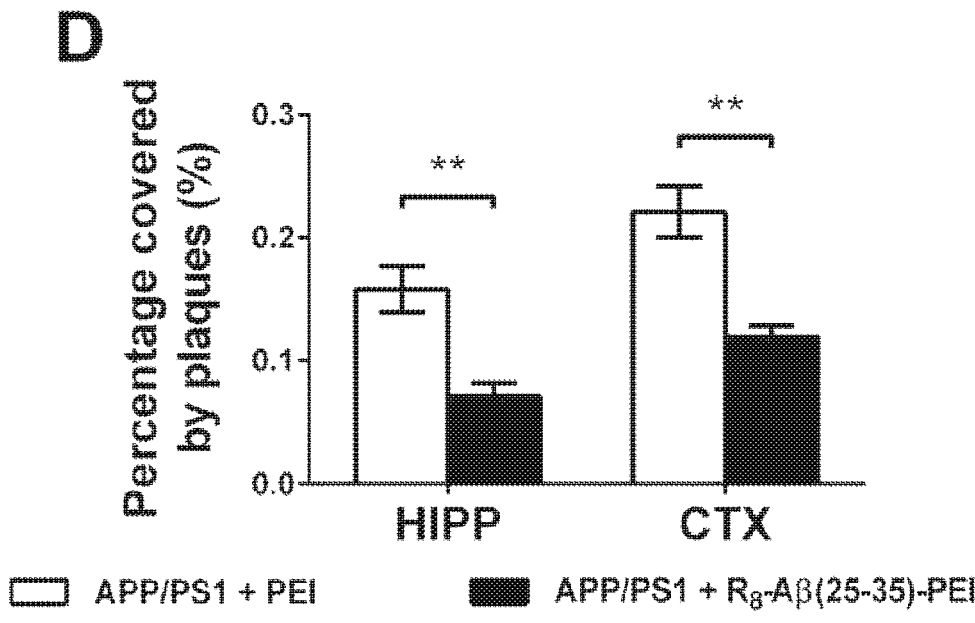
Figure 14:
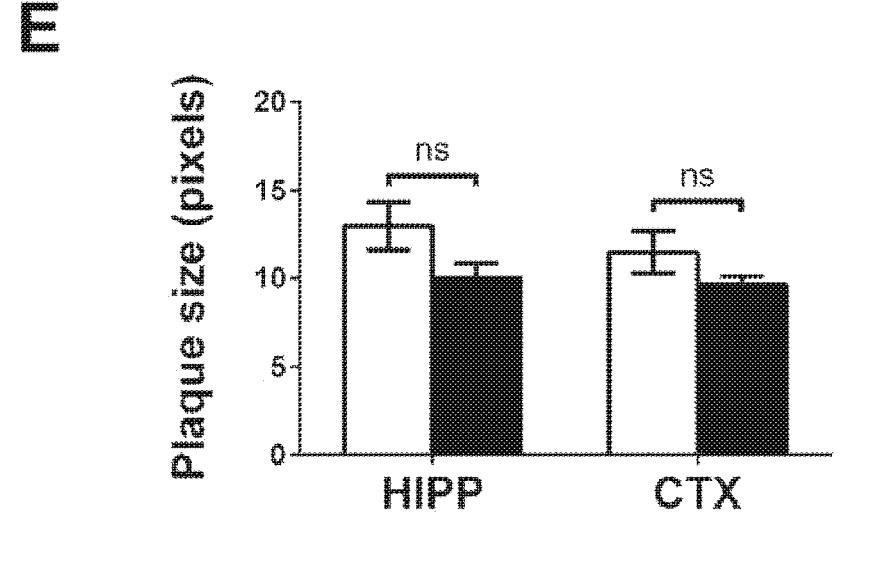
Figure 15:
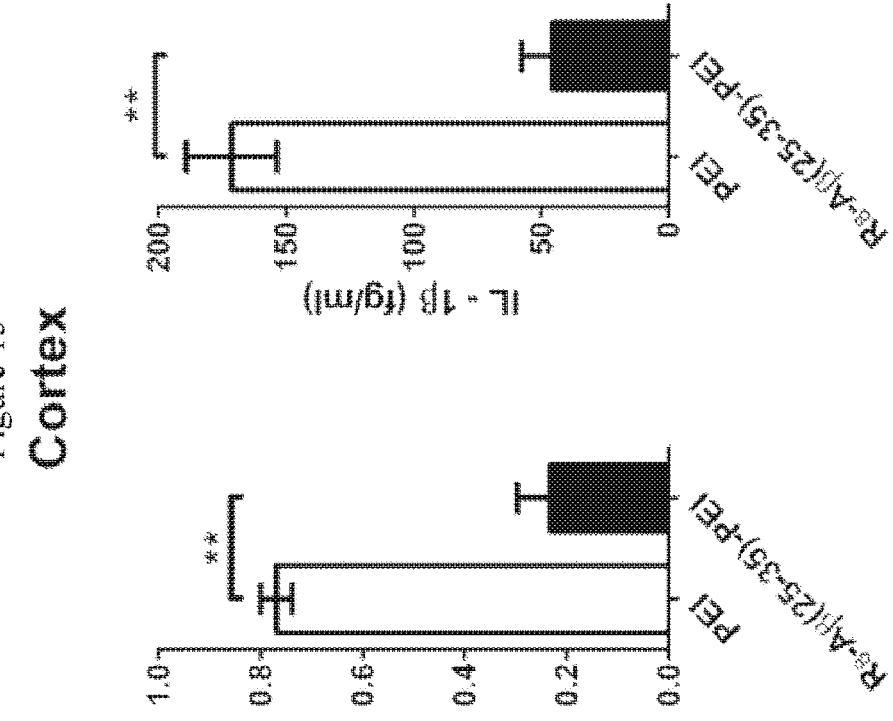
FIG. 15. Assays for the level of level of IL-6 and IL-1B in the cortex (N=3/group) in the 8 month-old Tg mice treated with PEI or R8-Aβ25-35-PEI peptide from the age of 4 months to 8 months. As shown, the therapeutic peptide significantly decreased the level of interleukin IL-6 and IL-1ß in the cortex. N=3/group; $**$: $P<0.01$. Statistics by Student's t-test.

Consistently, histological sections stained with Thioflavin S chemifluorescent dye revealed deposition of multiple green-fluorescent amyloid plaques in both cortex and hippocampus of the 8 month-old PEI-treated APP×PS1 mice, which was significantly reduced in the age-matched peptide-treated APP×PS1 mice (FIG. 14, panel A). As shown in FIG. 14, panel B, the number of plaques was significantly reduced in the cortex and hippocampus of the peptide-treated mice compared with that in the corresponding regions of the PEI-treated mice. The total area of amyloid plaques was correspondingly decreased in the both cortex and hippocampus of the peptide-treated mice vs. that in the PEI-treated controls (FIG. 14, panel C). To further eliminate the effect that might contribute to the positive results by the variation in the size of individual brain sections, the percentage of the area of the cortex and hippocampus that harbored amyloid plaques was calculated; the peptide treatment again significantly decreased the percentage of the plaque areas of both regions in comparison with the PEI control treatment (FIG. 14, panel D). Whether the size of individual plaques were altered by treatment was next examined; as shown in FIG. 14, panel E. Although the peptide treatment decreased the average size of individual plaques, the difference failed to reach statistical significance. The data indicated that the peptide treatment effectively slowed down the accumulation of amyloid plaques and the clinical impairment of the memory. Amyloid deposition induced neuroinflammation which contributed importantly to the diseases in these mice. $R_8$-A$\beta$(25-35)-PEI effectively decreased the level of pro-inflammatory cytokines interleukin (IL)-6 and IL-1$\beta$ in the cortex (FIG. 15).

Therapeutic Effect of Peptide after a Suspension for 4 Weeks

Figure 16:
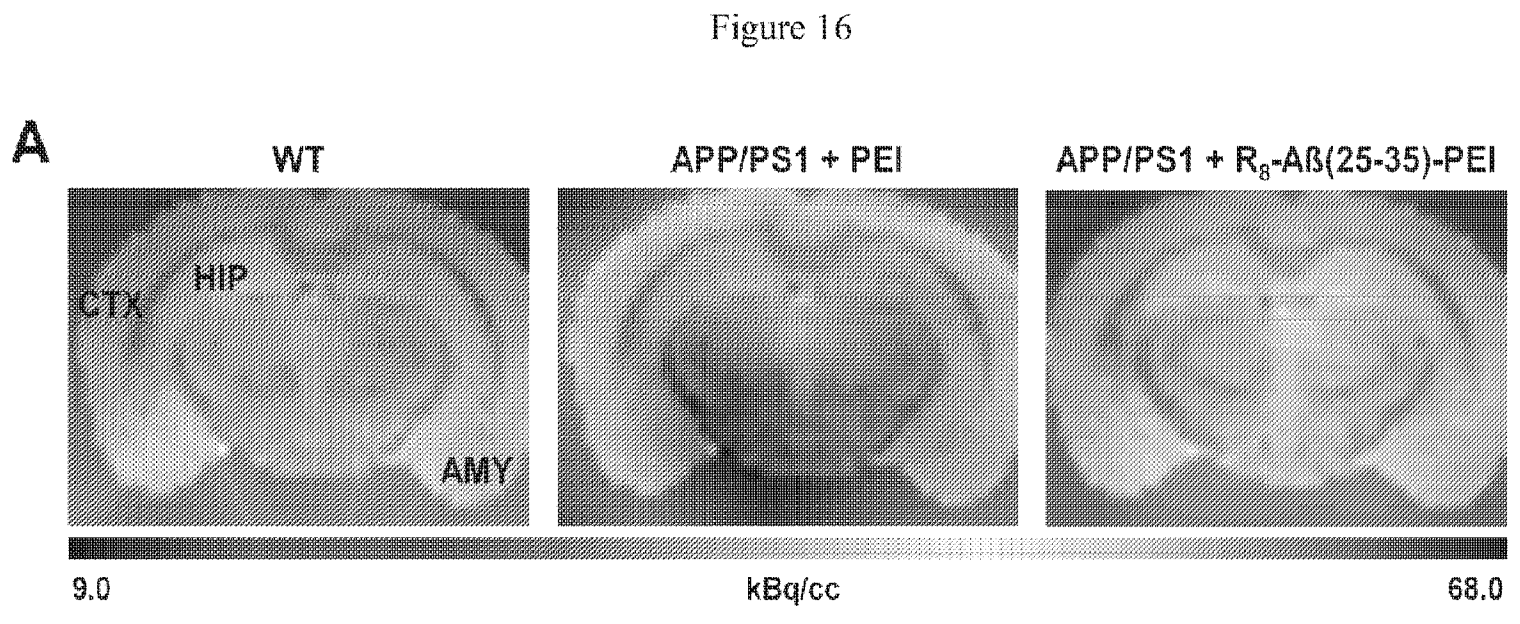
Figure 16:
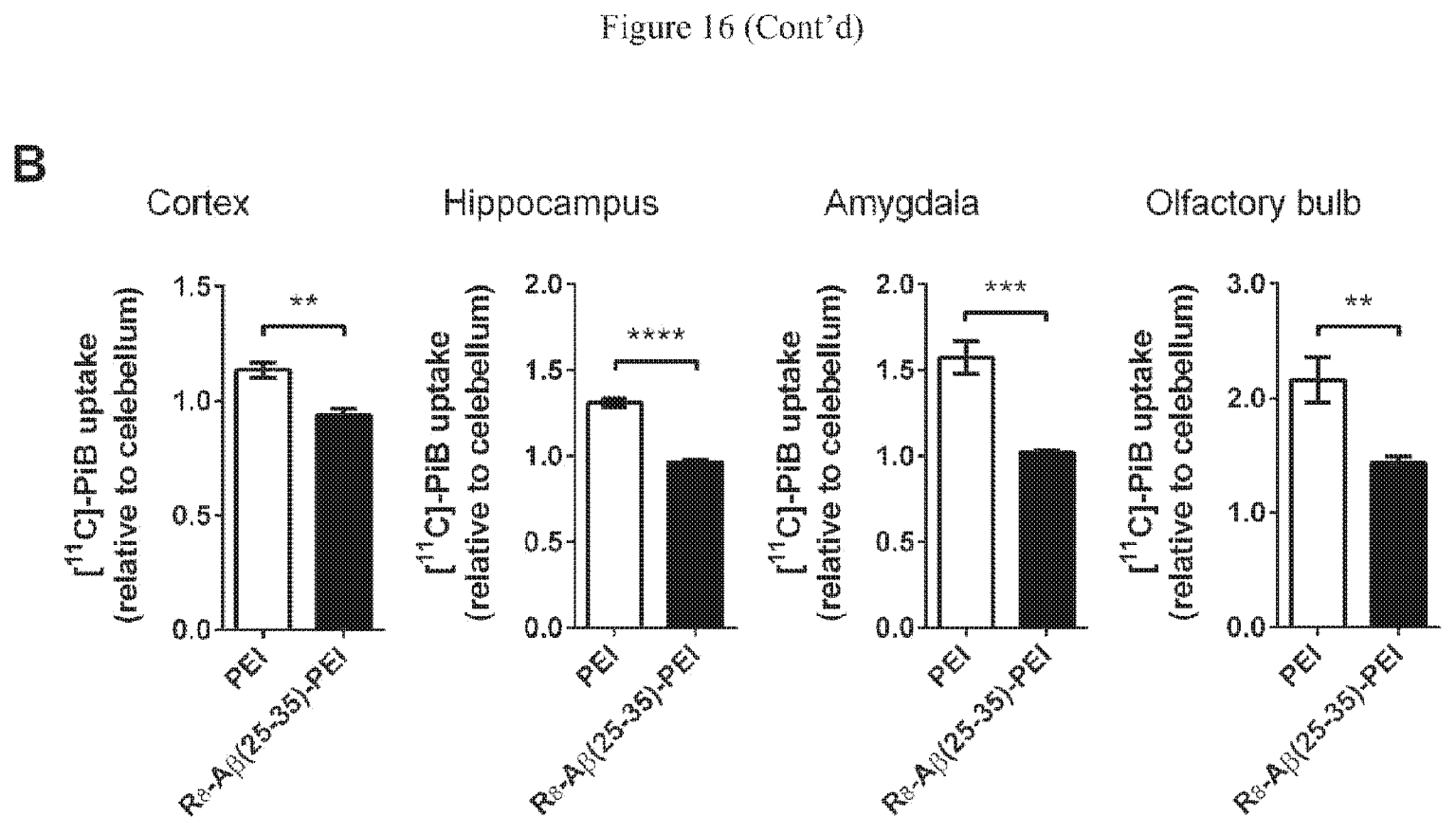
Figure 17:
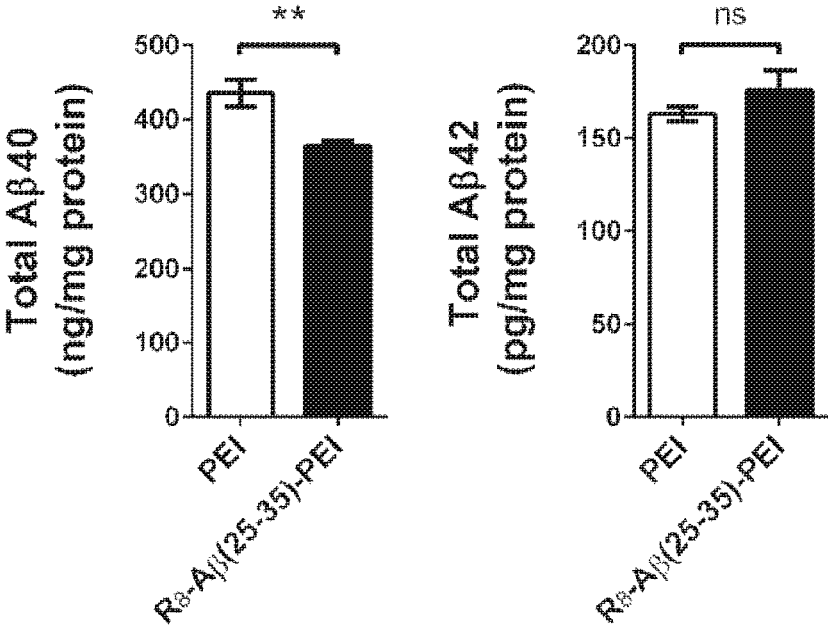
FIG. 17. ELISA assay of the level of total and insoluble Aβ40 and Aβ42 in the cortex and hippocampus in the 12 month-old Tg mice treated with PEI or $R_8$-Aβ(25-35)-PEI for 8 months. ELISA assay of total $Aβ_{40}$ and $Aβ_{42}$ in the cortex (panel A) and hippocampus (panel B) and insoluble $Aβ_{40}$ and $Aβ_{42}$ in the cortex (panel C) and hippocampus (panel D). (N=5 per group). Statistics were conducted with the Student's t test. $$: $p<0.01$; $*$: $p<0.001$; ns, not significant.
Figure 17:
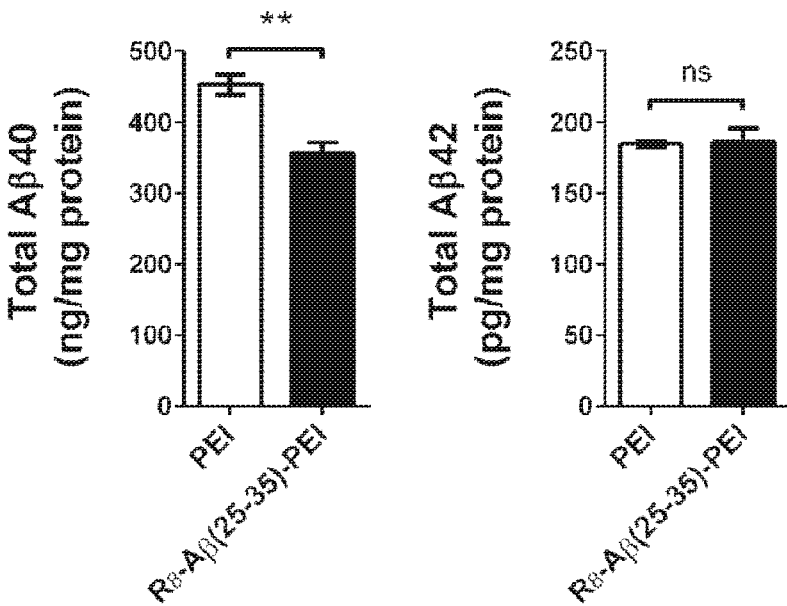
Figure 17:
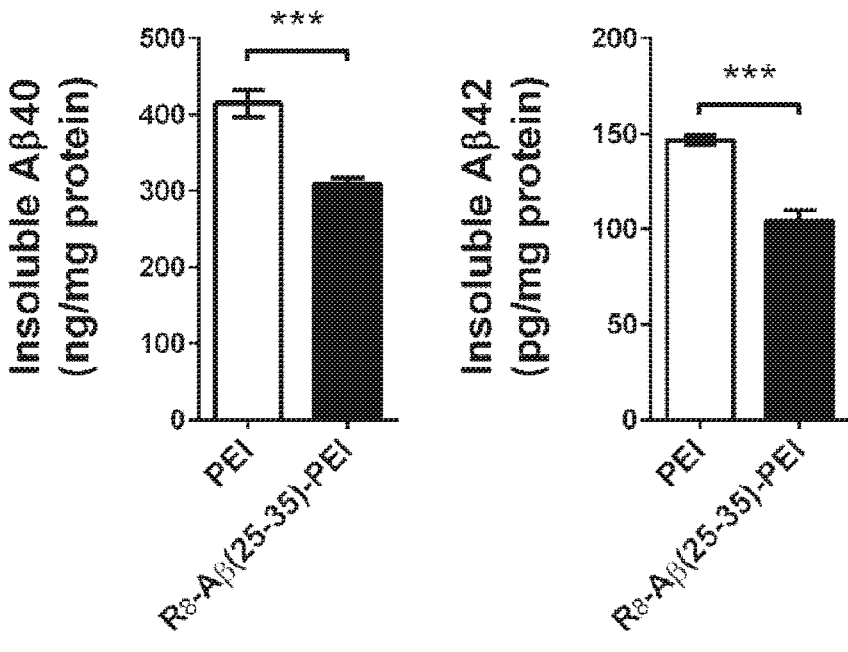
Figure 17:
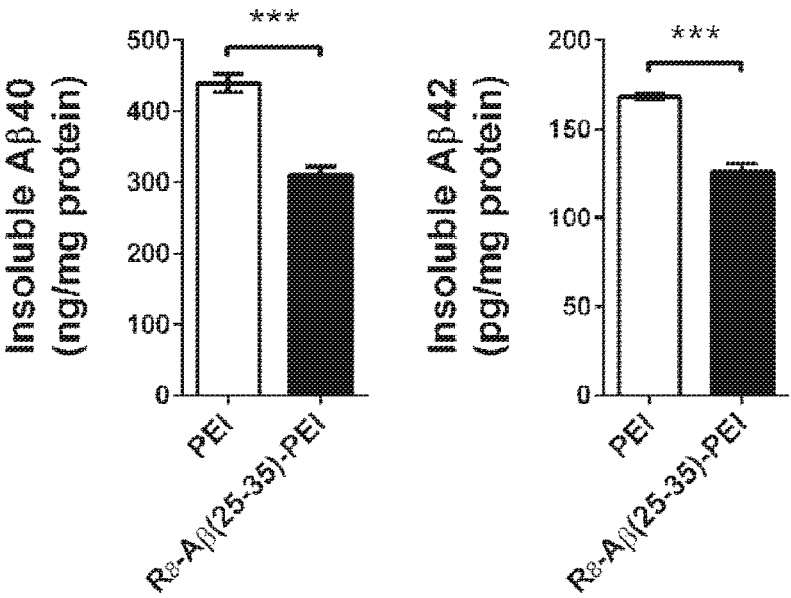

During the water maze tests, the treatment was adjourned for about 4 weeks. To examine whether the therapeutic effect could be maintained or resumed after a suspension of treatment, administration of PEI or peptide was resumed and continued until these mice reached 12 months of age. The burden of amyloid plaques was quantified with microPET using the tracer Pittsburgh compound B (PiB). As shown in FIG. 16, panels A and B, the $R_8$-A$\beta$(25-35) peptide-treated APP×PS1 mice had a much lower signal in the cortex, hippocampus, amygdala and olfactory bulb as compared with the PEI-treated mice, which is consistent with a beneficial therapeutic effect at this age. ELISA analyses revealed a decrease in total A$\beta_{40}$ by 16% and 21% in the cortex and hippocampus, respectively (FIG. 17, panels A and D). No statistical difference was detected in the level of total A$\beta_{42}$. Consistent with the results of microPET (17~35% reduction), the insoluble pools of A$\beta_{40}$ and A$\beta$42 were both decreased by 25~30% in the cortex or hippocampus of the peptide-treated APP×PS1 mice compared with those in PEI-treated mice (FIG. 17, panels C and D).

DISCUSSION

In this study, it was demonstrated that the peptide $R_8$-A$\beta$ (25-35) or its D-form counterpart could reduce the formation of amyloid fibrils by A$\beta_{40}$ peptide in vitro, and amyloid plaques and disease manifestation in vivo. Intranasal administration of $R_8$-A$\beta$(25-35) peptide also exhibited beneficial therapeutic effect in APP/PS1 transgenic mice. Thus, the data indicates that therapeutic peptides designed based on the affinity/charge modular principle described herein would be expected to be therapeutically effective in treating neurodegenerative diseases, particularly those that involve abnormal protein aggregation.

In the present design, the charged sequence not only enhanced cell permeability and bioavailability of the bipartite peptides, but also had an essential role in the peptidic therapy by providing a repulsion force to prevent the misfolded target from further aggregation. The charge moieties were introduced at both N- and C-ends of the peptide. The N-terminal positive charges were introduced by the guanido groups in the side-chains of poly-Arg; while the C-terminal positive charges, by the chemical modification of C-terminal carboxyl group with polyethylenimine. In addition, in comparison with another A$\beta$ aggregation-inhibiting PEI-coupled V24P(10-40) peptide, R8-A$\beta$ (25-35) performed better.

Although many therapeutic peptides have been designed, only few of them were tested in vivo (Shukla et al., *FASEB J* (2013) 27:174-86; Frydman-Marom et al., *Angew Chem Int Ed* (2009) 48:1981-6; Funke et al., *ACS Chem Neurosci* (2010) 1:639-48; Permanne et al., *FASEB J* (2002) 16:860-2; van Groen et al., *Chem Med Chem* (2008) 3:1848-52). In this study, the feasibility of the administration of therapeutic peptidic prodrugs through an intranasal route was demonstrated. When combined with technology in delivery, the study showed a proof of a therapeutic principle for neurodegenerative diseases through intranasal delivery. The dose used in this study was estimated to be 2 nmoles per day, which was quite low compared with previous studies. Frydman-Marom et al., *Angew Chem Int Ed* (2009) 48:1981-6; Funke et al., *ACS Chem Neurosci* (2010) 1:639-48; Permanne et al., *FASEB J* (2002) 16:860-2; van Groen et al., *Chem Med Chem* (2008) 3:1848-52.

Given the fact that amyloid plaques form extraordinarily rapidly in vivo, and might even do so as fast as in 1-2 days (Meyer-Luehmann et al., *Nature* (2008) 451:720-4), it was likely that after a 4-week interruption of treatment, deposition of amyloid plaques in the $R_8$-A$\beta$(25-35)-PEI-treated mice had approached or reached the level in PEI-treated mice. It was encouraging that the resumption of peptide treatment remained beneficial in 12 month-old mice. These findings indicate further prevention of amyloid plaques from deposition can be attained, even after a period of interruption. In fact, the preliminary tests for liver and kidney function indicated no clear toxicity in the mice receiving the peptides. In sum, intranasal administration of the designed bipartite peptides provided an effective and user-friendly preventative and therapeutic approach to treat aggregation-caused neurodegenerative diseases.

Example 3: Intranasal Delivery of a Bipartite Peptide Reduced Amyloid Burden in the Brains of APP/PS1 Transgenic Mice A "scavenger peptide", V24P(10-40), designed to decrease A$\beta$ accumulation in the brain, was conjugated to polyethylenimine (PEI), and tested as a preventive and/or therapeutic strategy for Alzheimer's disease (AD) in this study. This PEI-conjugated V24P(10-40) peptide was delivered intranasally to the APP/PS1 double transgenic mice of 4 months of age as nasal drops for four months. Compared with control values, peptide treatment reduced the amount of A$\beta$ peptides by 72% of A$\beta$40 and 40% of A$\beta$42 in the hippocampus, and by 87% of A$\beta$40 and 32% of A$\beta$42 in the cortex. After treatment for 8 months, amyloid load, as quantified by Pittsburgh compound B microPET imaging, was decreased significantly in the hippocampus, cortex, amygdala, and olfactory bulb. The data demonstrate that the intranasally delivered scavenger peptide is effective in decreasing A$\beta$ plaque formation in the brain. Nasal application of peptide drops is user-friendly, and could be further developed for preventative and therapeutic purposes with respect to AD and other neurodegenerative diseases, including those described herein.

Materials and Methods

Synthesis of the PEI-Conjugated Peptide

All peptides were synthesized by the batch fluorenyl-methoxycarbonyl (fmoc)-polyamide method. Chen et al., *Protein Sci* (2001) 10:1794-1800. To generate PEI-conjugated V24P(10-40), PEI was conjugated to the C-terminal carboxyl group of the peptide, and the N-terminal group of V24P(10-40) was acetylated to avoid dimerization or cyclization of the peptide during PEI-conjugation reaction and to provide protection against exopeptidases. Acetylated V24P (10-40) (4.8 mg) dissolved in 4 mL of dimethyl sulfoxide was slowly mixed with 240 µL of 1-ethyl-3-(3-dimethyl-aminopropyl) carbodiimide (600 mM in 0.1 M MES, 0.5 M NaCl, pH 6), then 240 µL of N-hydroxysuccinimide (1200 mM in 0.1 M MES, 0.5 M NaCl, pH 6) was added, and the mixture was reacted at room temperature for 30 min with gentle shaking (70 rpm). PEI (288 μL) was added and the mixture was incubated overnight at room temperature with gentle shaking (70 rpm). The PEI-conjugated peptide, V24P (10-40)-PEI, was separated from unreacted PEI and V24P (10-40) by reverse-phase HPLC.

Animal Experiment

APP/PS1 transgenic mice (B6C3-Tg (APPswe, PSEN1dE9) 85Dbo/Mmjax), purchased from Jackson Laboratories (USA), were bred and genotyped as described on the Jackson website. Jankowsky et al., *Biomol Eng* (2001) 17:157-65; Borchelt et al., *Neuron* (1996) 17:1005-13. The mice had access to food and water ad libitum and were kept on a 12:12 h light-dark cycle. PEI and V24P(10-40)-PEI were dissolved at a concentration of 400 μM in 100 mM NaH$_2$PO$_4$, 138 mM KCl, pH 5, and 4-month-old mice was given 2.5 μL of PEI (as the control) or V24P(10-40)-PEI in each nostril six days per week for the indicated period.

ELISA assays for Aβ40 and Aβ42

Concentrations of Aβ40 and Aβ42 in mouse brain homogenate were measured using ELISA kits (Invitrogen, MD, USA) according to the manufacturer's instructions. Briefly, the cortical or hippocampal tissue from PEI-treated or V24P(10-40)-PEI-treated APP/PS1 mice was weighed and homogenized at 4° C. in the cell extraction buffer provided in the kit, supplemented with protease inhibitor cocktail (Sigma, St. Louis, USA), then the homogenates in Eppendorf tubes were centrifuged at 13000 rpm at 4° C. for 10 min and the concentration of protein in the supernatant was measured using the microBCA protein assay (Thermo, IL, USA). To perform the ELISA, the supernatants were diluted 10-fold and the Aβ40 and Aβ42 concentrations were normalized to the protein concentration and expressed as ng/mg of protein.

In Vivo microPET

[$^{11}$C] PIB was generated using [$^{11}$C] methyltriflate using a previously described method with minimal modification. Manook et al., *PLOS One* (2012) 7: e31310. PET scans were performed using a Triumph pre-clinical tri-modality (Lab-PET/X-SPECT/X-O CT) imaging system (TriFoil Imaging, USA). The mice were kept warm with a heating lamp before scanning. After induction with 2.0% isoflurane, the mice were placed with their heads in the center of the field of view, fixed in the prone position, and then freshly synthesized [$^{11}$C] PiB (36.7±2.6 MBq; volume <0.25 mL) was injected via the tail vein. After 20 min, static data acquisition was performed for 20 min in 3D list mode with an energy window of 350-650 keV. The emission data were normalized and corrected for the tracer decay time. All list mode data were sorted into 3D sinograms, which were then single-slice Fourier rebinned into 2D sinograms. Summation images from 20 to 40 min after [$^{11}$C] PiB injection were reconstructed using a MLEM algorithm.

All imaging data were processed and analyzed using the PMOD 3.5 software package (Pmod Technologies, Zürich, Switzerland). The PET image dataset was converted to an absolute measure of radioactivity concentration (kBq/cc) using a phantom-derived calibration factor before being normalized to the injected dose of [$^{11}$C] PiB and the body mass of the animal. Static PET images were co-registered with the mouse T2-weighted MRI brain atlas based on PMOD as anatomic reference. Image origins were set to bregma (0, 0) according to the MRI atlas, which was also used for VOI definition. [$^{11}$C] PiB uptake in the cortex, hippocampus, amygdala, and olfactory bulb was evaluated. Standardized uptake values were obtained for each VOI by dividing the mean [$^{11}$C] PiB activity by the injection dose and the body weight (in grams). Thereafter, the regional

[$^{11}$C] PiB uptake in the target region was normalized to [$^{11}$C] PiB uptake in the cerebellum, taken as the reference region. Manook et al., *PLOS One* (2012) 7: e31310; Poisnel et al., *Neurobiol Aging* (2012) 33:2561-71.

Results

Several mutated Aβ40 peptides with different N- and C-terminal truncations were designed and synthesized (Table 3). Their structural properties were first examined by Circular Dichroism (CD) Spectroscopy, the Thioflavin T (ThT) binding assay, and Transmission Electron Microscopy (TEM), and then their effects on the formation of Aβ$_{40}$ fibrils and Aβ$_{40}$ cytotoxicity using a cell viability assay in mouse neuroblastoma Neuro2a (N2a) cells was performed.

TABLE 3

The synthesized peptides used in this study.

| Peptide | Sequence |
|---|---|
| Aβ40 | DAEFRHDSGY EVHHQKLVFF AED$\underline{V}$GSNKGA IIGLMVGGVV |
| V24P(1-28) | DAEFRHDSGY EVHHQKLVFF AED$^D$PGSNK |
| V24P(10-40) | Y BVHHQKLVFF AED$^D$PGSNKGA I$\overline{IG}$LMVGGVV |
| V24P(13-36) | HHQKLVFF AED$^D$PG$\overline{SN}$KGA IIGLMV |
| V24P(16-33) | KLVFF AED$^D$PG$\overline{SN}$KGA IIG |
| V24P(19-30) | FF AED$^D$PG$\overline{SN}$KGA |

$^D$P represents D-proline

The sequences in Table 3, from top to bottom, correspond to SEQ ID NOs: 20-25.

C-Terminal-Truncated Peptide V24P(1-28)

Figure 18:
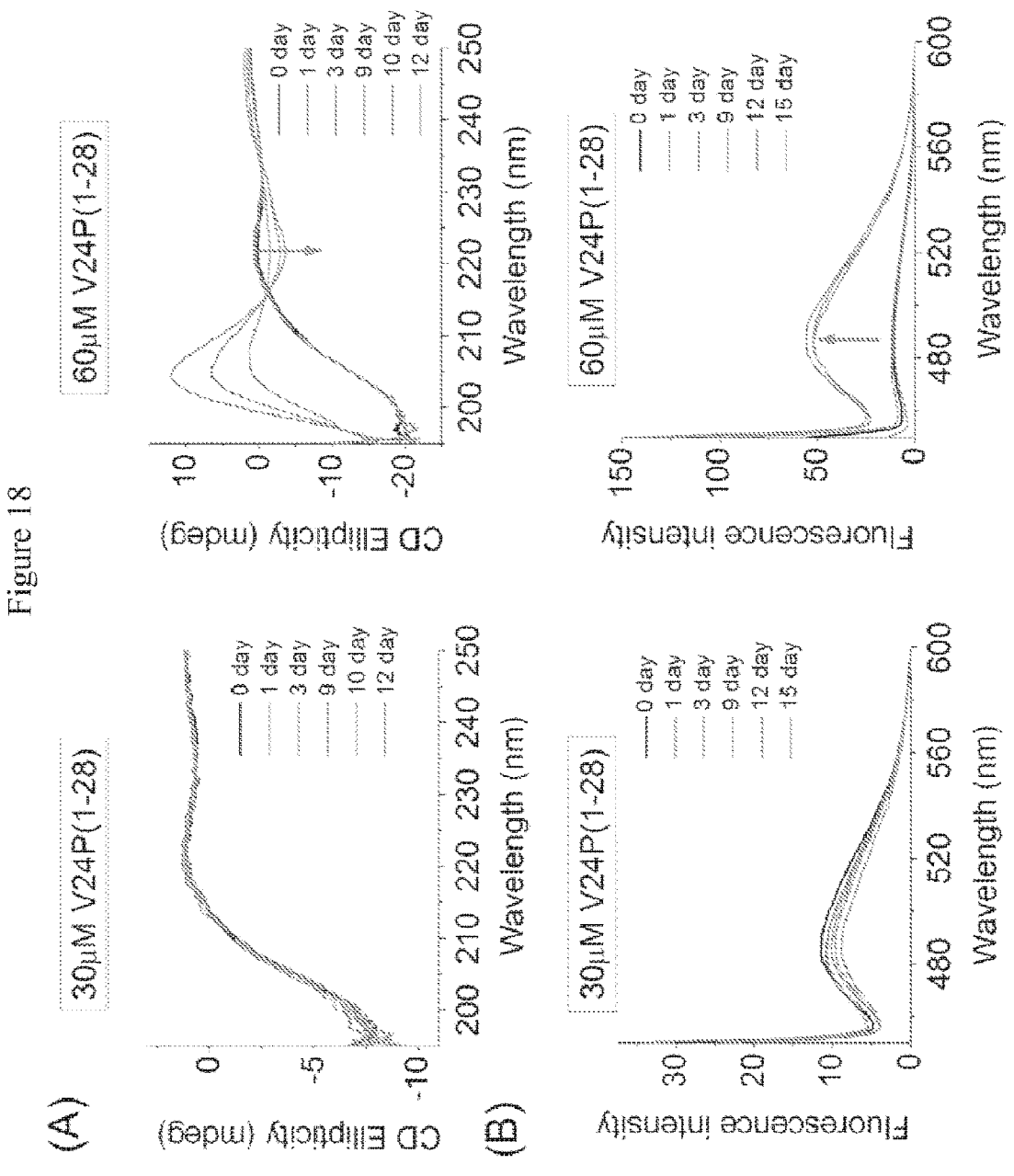
FIG. 18. Structural studies on V24P(1-28) and V24P(10-40). The peptides at concentrations of 30 or 60 μM were incubated at 25° C. for the indicated times (0-12 days), then the CD spectra (panels A and C) and fluorescence spectra after binding ThT (panels B and D) were recorded. Panel E.

According to the structural model of the Aβ 40 fibrils (Petkova et al., *Proc Natl Acad Sci* (2002) 99:16742-7), K28 is located at the beginning of the second β-strand. Without the C-terminal hydrophobic tail following K28, V24P(1-28) had increased hydrophilicity compared with A β 40. V24P (1-28) was dissolved in 20 mM sodium phosphate buffer, pH 7, containing 150 mM KCl (incubation buffer) and then incubated at 25° C. At different time points (Day 0 was the time immediately after dissolution), its CD spectra and fluorescence spectra after ThT binding were recorded. The CD spectrum of the 30 μM V24P(1-28) solution was typical of a random coil structure and was identical at all tested time points (0-12 days) (FIG. 18, panel A, left); consistently, the measurement of fluorescence showed no ThT binding (FIG. 18, panel B, left). When the peptide concentration was increased to 60 μM, V24P(1-28) remained as a random structure at days 0-3, but gradually formed a β-sheet structure (FIG. 18, panel A, right), which bound ThT, as shown by the increased fluorescence (FIG. 18, panel B, right). TEM showed that 60 μM V24P(1-28) formed amyloid fibrils (FIG. 18, panel E, left). The fibrils were straight and laterally associated, in contrast with the twisted morphology commonly reported for A β 40 fibrils. Chang et al., *J Mol Biol* (2009) 385:1257-65; Meinhardt et al., *J Mol Biol* (2009) 386:869-77; Goldsbury et al., *J Struct Biol* (2000) 130:217-31.

N-Terminal-Truncated Peptide V24P(10-40)

The N-terminal region of Aβ 40 is hydrophilic and was reported not to be involved in the amyloid cross-β structure. Petkova et al., *Proc Natl Acad Sci USA* (2002) 99:16742-7. To verify whether this hydrophilic segment was important in the design of a peptide inhibitor, a V24P mutant peptide, denoted V24P(10-40), with the first 9 N-terminal amino acid residues truncated was chemically synthesized and dissolved in the incubation buffer. Unlike 30 μM V24P forming a random coil structure (Chang et al., *J Mol Biol* (2009) 385:1257-65), the CD spectra of 30 μM V24P(10-40) exhibited a characteristic β-sheet signal evidenced by negative ellipticity at 218 nm (FIG. 18, panel C, left) and, consistently, fluorescence emission at 487 nm appeared in the ThT binding assay (FIG. 18, panel D, left). These data showed that V24P(10-40) was more prone to aggregate than V24P. At the concentration of 60 μM, more β-aggregates were formed (FIG. 18, panels C and D, right). TEM showed that V24P(10-40) formed amorphous aggregates (FIG. 18, panel E, right).

Structural Studies on Shorter Peptide

In order to determine the shortest sequence for self-aggregation, an additional three peptides with shorter lengths, V24P(13-36), V24P(16-33), and V24P(19-30) were designed, and their CD spectra and fluorescence spectra after binding ThT immediately after dissolution at concentrations of 30, 60, and 90 μM were examined.

The CD spectra showed that V24P(13-36) formed a random coil structure at 30 μM (FIG. 19, panel A, top) and the ThT fluorescence spectra showed that β-aggregates formed at 90 μM (FIG. 19, panel B, top). V24P(13-36) lacked several hydrophobic residues (Y10, V12,V39, V40) present in the V24P(10-40), and thus required a higher peptide concentration (90 μM) to form β-aggregates compared with V24P(60μ) or V24P(10-40) (30 μM).

In contrast, the CD spectrum of V24P(16-33) showed a strong peak at 204 nm and a trough at 228 nm (FIG. 19, panel A, center panel), a pattern indicative of a type I β-turn (Kelly et al., *Curr Protein Pept Sci* (2000) 1:349-84; Kelly et al., *BBA-Protein Proteom* (2005) 1751:119-39). The weak fluorescence of 90 μM V24P(16-33) suggested that only a small amount of β-aggregates formed (FIG. 19, panel B, center).

V24P(19-30) showed a random coil structure. When the peptide concentration was 60 μM or higher, the CD spectra showed a peak at around 220 nm (FIG. 19, panel A, bottom), similar to that of an extended 310 helix or a poly(Pro) II helix (Kelly et al., *BBA-Protein Proteom* (2005) 1751:119-3930). No fluorescence emission at 487 nm was observed at any concentration (FIG. 19, panel B, bottom), suggesting that L17, V18, 131, and 132 were responsible for ThT binding to V24P(16-33) aggregates.

Selection of Scavenger Peptide

A single substitution (V24→$^D$P) in Aβ40 dramatically affects the structural behavior and decreases the toxicity of Aβ 40. (Chang et al., *J Mol Biol* (2009) 385:1257-65). FIG. 20, panel A shows that all of the $^D$P-containing peptides tested were much less cytotoxic than Aβ 40. Compared with V24P, V24P(10-40) formed β-aggregates at a lower peptide concentration, suggesting that it had a higher propensity to aggregate and might have a greater inhibitory effect on Aβ 40 cytotoxicity. In the cytotoxicity assay, Aβ 40 peptide, when mixed with V24P(10-40) at an equi-molar ratio, had the lowest cytotoxicity. FIG. 20, panel B. Therefore, V24P (10-40) was chosen as the scavenger peptide in the following animal studies.

The Inhibitory Effect of V24P(10-40) on Amyloid Formation was Specific for Aβ40

Many peptide inhibitors were designed based on a short recognition sequence, such as "KLVFF" (SEQ ID NO: 26), but the target specificity of this sequence for different amyloid-forming peptides had rarely been examined. Therefore, hamster prion peptide PrP(108-144) was used to explore the association specificity of V24P(10-40). PrP(108-144) formed amyloid fibrils when incubated in 20 mM NaOAc buffer, pH 3.7/140 mM NaCl. Chen et al., *Proc Natl Acad Sci USA* (2002) 99:12633-8. As shown in FIG. 21, whether equimolar V24P(10-40) was added or not, the fluorescence intensity increase in the ThT binding assay showed that PrP(108-144) formed amyloid fibrils during incubation, and V24P(10-40) failed to inhibit amyloid formation of PrP(108-144). These results indicated that the inhibitory effect of V24P(10-40) was target-specific.

Scavenger Peptide V24P(10-40) Decreased Aβ Accumulation in the Brains of APP/PS1 Transgenic Mice In the design of peptide inhibitors, D-form amino acids, end capping, and methylation of amide hydrogens are often used to combat digestions by exopeptidases and endopeptidases in the serum in order to extend the lifetime of the peptide in vivo. Findeis et al., *Biochem* (1999) 38:6791-800; Gordon et al., *Biochem* (2001) 40:8237-45; Gordon et al., *J Pept Res* (2002) 60:37-55. Modifications to putrescine, a naturally occurring polyamine, have been used to increase the ability of a designed peptide D-YiAβ11 to cross the blood brain barrier. Poduslo et al., *J Neurobiol* (1999) 39:371-82. Polyethylenimine (PEI) cationized proteins were also found to be able to cross the cell membrane. Futami et al. *J. Biosci. Bioeng.* (2005) 99 (2): 95-103; Futami et al., *Expert. Opin. Drug. Discov.* (2007) 2:261-269; Kitazoe et al., *J. Biochem.* (2005) 137:693-701; Kitazoe et al., *Biotechnol. J.* (2010) 5:385-392; Murata et al., *J. Biochem.* (2008) 144:447-455; Murata et al., *J. Biosci. Bioeng.* (2008) 105:34-38.

In this study, PEI was added to the C-terminus of the scavenger peptide V24P(10-40). 4-month-old APP/PS1 transgenic mice were administered with V24P(10-40)-PEI or PEI alone by nasal drops to both nostrils (1 nmole or 4 μg per nostril) six times per week. The mice were then sacrificed 4 months later and the A β contents of the brain were analyzed by ELISA. As shown in FIG. 22, the mice treated with V24P(10-40)-PEI clearly had decreased A β40 and A β42 levels in both the cortex (panel A) and hippocampus (panel B), the effect being greater with Aβ40, probably because the scavenger peptide does not contain residues 41 and 42.

The effect of the scavenger peptide on reducing amyloid plaque accumulation was examined in APP/PS1 mice treated with V24P(10-40)-PEI or PEI from the age of 4 months to 12 months, using micro positron emission tomography (microPET) with the radiotracer $^{11}$C-labeled Pittsburgh compound B ([$^{11}$C] PiB), which binds to A β plaques. The microPET images (FIG. 23, panel A) taken at the end of treatment showed that A β plaque deposition was decreased significantly by the peptide treatment. Quantification of [$^{11}$C] PiB levels in the cortex, hippocampus, amygdala, and olfactory bulb in APP/PS1 mice with or without peptide treatment revealed that peptide treatment resulted in a significant reduction in amyloid plaque formation in all four brain regions (FIG. 23, panel B).

DISCUSSION

All the peptides with the V24→DP replacement were less toxic than Aβ40 for N2a cells, suggesting that V24 is an important residue for Aβ40 to form toxic species. In addition, the data showed that, without the C-terminal hydrophobic tail, V24P(1-28) still retained the ability to form amyloid fibrils as an Aβ 40 peptide, whereas peptides without the N-terminal hydrophilic tail increased the aggregation propensity of V24P(10-40) to form amyloid-like β-aggregates. Shorter peptides V24P(13-36), V24P(16-33), and V24P(19-30) had lower aggregation propensity and a higher peptide concentration was required for them to form amyloid-like β-aggregates.

The results of these peptide inhibitors tested in the transgenic mouse models described herein were summarized and compared in Table 4. In the present study, non-invasive intranasal administration and less peptide (~200 µg of V24P (10-40)-PEI per mouse per month) were used. Treatment for four months resulted in a reduction of 72% and 40% in the $A\beta_{40}$ and $A\beta_{42}$ content of the hippocampus, respectively. In terms of total peptide used in transgenic mouse models, 0.8 mg of V24P(10-40)-PEI was used, while previous studies used 2.5 mg of iAβ5p (icv infusion), 24 mg of iAβ5p (ip), 0.27 mg of D3 (hippocampal infusion), 28-56 mg of D3 (oral), or 3 mg of D-Trp-Aib. The present peptide markedly reduced both the Aβ level and amyloid accumulation in the brain at a much lower dosage when given via a non-invasive route. Thus, the present data shows the therapeutic effects of the bipartite peptides described herein for delaying the onset and/or reducing the progression of AD.

Questions have been raised about peptide therapy in terms of immunogenicity, low stability, low solubility, poor bioavailability, and low BBB permeability. The present study proved that intranasal administration is an effective method of delivering peptide drugs into the brain. Since this administration route is much more user-friendly than the invasive routes such as intracerebral infusion or ip injection, peptide drugs can be given daily in this manner. Intranasal peptide administration could be used to deliver other peptide inhibitors targeting other functions in the brain, for example, the 24-aa peptide TFP5 derived from p35 (the cdk5 activator) which has been reported to reduce cdk5 hyperactivation and inhibit tau hyperphosphorylation in mice via ip injection. Shukla et al., *FASEB J* (2013) 27:74-86.

TABLE 4

Comparison of different peptides used in APP transgenic mice.

| Peptide | Administration route and mouse age at start and end of treatment[a] | Total peptide (mg) | Total peptide (µmol) | Aβ in hippocampus (% of control) |
|---|---|---|---|---|
| V24P(10-40)-PEI | Intranasal delivery 6 times a week for 4 months; 4-m to 8-m | 0.8 | 0.2 | Aβ40 28%[b] Aβ42 60% |
| V24P(10-40)-PEI | Intranasal delivery 6 times a week for 8 months; 4-m to 12-m | 1.6 | 0.4 | 81%[c] |
| iAβ5p (40) | Icv infusion for 8 weeks: 6/7-m to 8/9-m | 2.5 | 3.6 | 33%[d] |
| iAβ5p (40) | Ip injection 3 times a week for 8 weeks: 8/9-m to 10/11-m | 24 | 34.6 | 54%[a] |
| D3 (42) | Hippocampal infusion for 30 days; 8-m to 9-m | 0.27 | 0.17 | 67%[d] |

TABLE 4-continued

Comparison of different peptides used in APP transgenic mice.

| Peptide | Administration route and mouse age at start and end of treatment[a] | Total peptide (mg) | Total peptide (µmol) | Aβ in hippocampus (% of control) |
|---|---|---|---|---|
| D3 (43) | Oral daily for 8 weeks; 4-m to 6-m | 28-56 | 17.5-35 | 68%[d] |
| D-Trp-Aib (44) | Ip injection 3 times daily for 120 days; 4.5-m to 8.5-m | 3 | 10.4 | 53%[e] |

[a]intracerebroventricular (icv); intraperitoneal (ip)
[b]quantified by ELISA
[c]quantified by microPET
[d]quantified by immunohistochemistry
[e]quantified by thioflavin S staining
40 Permanne et al. FASEB J. (2002) 16(8):860-862.
42 van Groen et al., ChemMedChem (2008) 3:1848-1852.
43 Funke et al. ACS Chem. Neurosci. (2010) 1(9):639-648.
44 Frydman-Marom et al., Angew. Chem. Int. Ed. (2009) 48:1981-1986.

(Relevant teachings of these references are incorporated herein by reference.)

MicroPET images showed that THE amyloid load in the olfactory bulb was significantly decreased. It has been reported that senile plaques and neurofibrillary tangles accumulate in the olfactory bulb and olfaction is damaged in the early stage of AD. Christen-Zaech et al., *Can J Neurol Sci* (2003) 30:20-5; Arnold et al., *Ann Neurol* (2010) 67:462-9. In APP transgenic mice, non-fibrillar Aβ deposition can be detected in the olfactory bulb earlier than in other brain regions, and olfactory dysfunction correlates with A β burden. Wesson et al., *J Neurosci* (2010) 30:505-14. Thus, A β deposition in the olfactory epithelium may serve as a biomarker for identifying AD patients at the preclinical stage. Attems et al., *Acta Neuropathol* (2014) 127:459-75. Since the present peptide was delivered to the brain intranasally, it has the advantage of inhibiting Aβ deposition in the olfactory bulb at the early stage of AD progression.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating Alzheimer's disease (AD), comprising administering to a subject in need thereof an effective amount of a pharmaceutical composition, wherein the pharmaceutical composition comprises a bipartite molecule and a pharmaceutically acceptable carrier, and the bipartite molecule is (a) a molecule comprising the amino acid sequences of RRRRRRRRGSNKGAHGLM-PEI (SEQ ID NO: 4), wherein the C-terminal PEI is polyethylenimine; or (b) a molecule comprising the amino acid sequences of YEVHHOKLYFFAED$^D$PGSNKGANGLMYGGVV-PEI (SEQ ID NO: 5), wherein the C-terminal PEI is polyethylenimine.

2. The method of claim 1, wherein the subject is a human.

3. The method of claim 1, wherein the bipartite molecule is administered by an intranasal route.

4. A method for treating Huntington's disease (HD), comprising administering to a subject in need thereof an effective amount of a pharmaceutical composition, wherein the pharmaceutical composition comprises a bipartite molecule and a pharmaceutically acceptable carrier, and the bipartite molecule is (a) a molecule comprising the amino acid sequences of RRRRRRRRWDQQQQQQQQQQ (SEO ID NO: 6); or (b) a molecule comprising the amino acid sequences of RRRRRRRRWDQQQQQQQQQQQQQQQQ (SEO ID NO: 7).

5. The method of claim 4, wherein the subject is a human.

6. The method of claim 4, wherein the bipartite molecule is administered by an intranasal route.

* * * * *

SEQUENCE LISTING

```
<160> NUMBER OF SEQ ID NOS: 26

<210> SEQ ID NO 1
<211> LENGTH: 11
<212> TYPE: PRT
<213> ORGANISM: Artificial Sequence
<220> FEATURE:
<223> OTHER INFORMATION: Synthetic Polypeptide
```

```
<400> SEQUENCE: 1

Gly Ser Asn Lys Gly Ala Ile Ile Gly Leu Met
1               5                   10

<210> SEQ ID NO 2
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 2

Tyr Glu Val His His Gln Lys Leu Val Phe Phe Ala Glu Asp Asp Pro
1               5                   10                  15

Gly Ser Asn Lys Gly Ala Ile Ile Gly Leu Met Val Gly Gly Val Val
            20                  25                  30

<210> SEQ ID NO 3
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 3

Arg Arg Arg Arg Arg Arg Arg Arg Gly Ser Asn Lys Gly Ala Ile Ile
1               5                   10                  15

Gly Leu Met

<210> SEQ ID NO 4
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 4

Arg Arg Arg Arg Arg Arg Arg Arg Gly Ser Asn Lys Gly Ala Ile Ile
1               5                   10                  15

Gly Leu Met

<210> SEQ ID NO 5
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (15)..(15)
<223> OTHER INFORMATION: Xaa is the D-form of proline

<400> SEQUENCE: 5

Tyr Glu Val His His Gln Lys Leu Val Phe Phe Ala Glu Asp Xaa Gly
1               5                   10                  15

Ser Asn Lys Gly Ala Ile Ile Gly Leu Met Val Gly Gly Val Val
            20                  25                  30

<210> SEQ ID NO 6
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 6

Arg Arg Arg Arg Arg Arg Arg Trp Asp Gln Gln Gln Gln Gln Gln
1               5                   10                  15

Gln Gln Gln Gln
            20

<210> SEQ ID NO 7
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 7

Arg Arg Arg Arg Arg Arg Arg Arg Trp Asp Gln Gln Gln Gln Gln
1               5                   10                  15

Gln Gln Gln Gln Gln Gln Gln Gln Gln
            20                  25

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

Arg Pro Arg Thr Arg Leu His Thr His Arg Asn Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

Arg Arg Arg Arg Arg Arg Arg Arg
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 10

Gly Arg Lys Lys Arg Arg Gln Arg Arg Arg Pro Gln
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 11

Arg Arg Arg Arg Arg Arg Arg Arg Trp Asp
1               5                   10

<210> SEQ ID NO 12
```

```
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 12

Arg Arg Arg Arg Arg Arg Arg Arg Trp Asp Gln Gln Gln Gln Gln
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 13

Arg Arg Arg Arg Arg Arg Arg Arg Trp Asp Gln Gln Gln Gln Gln
1               5                   10                  15

Gln Gln Gln Gln
            20

<210> SEQ ID NO 14
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 14

Arg Arg Arg Arg Arg Arg Arg Arg Trp Asp Gln Gln Gln Gln Gln
1               5                   10                  15

Gln Gln Gln Gln Gln Gln Gln Gln Gln
            20                  25

<210> SEQ ID NO 15
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 15

Arg Arg Arg Arg Arg Arg Arg Arg Trp Asp Gln Gln Gln Gln Gln
1               5                   10                  15

Gln Gln Gln Gln Gln Gln Gln Gln Gln Gln Gln Gln Gln Gln Gln
            20                  25                  30

<210> SEQ ID NO 16
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 16

Arg Gln Gln Arg Arg Gln Gln Asp Gln Arg Gln Trp Gln Arg Gln Arg
1               5                   10                  15

Gln Gln Arg

<210> SEQ ID NO 17
<211> LENGTH: 10
<212> TYPE: PRT
<213> ORGANISM: Artificial Sequence
```

```
<220> FEATURE:
<223> OTHER INFORMATION: Synthetic Polypeptide

<400> SEQUENCE: 17

Arg Arg Arg Arg Arg Arg Arg Arg Trp Asp
1               5               10

<210> SEQ ID NO 18
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 18

Arg Arg Arg Arg Arg Arg Arg Arg Trp Asp Gln Gln Gln Gln Gln Gln
1               5               10              15

Gln Gln Gln Gln
        20

<210> SEQ ID NO 19
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 19

Arg Gln Gln Arg Arg Gln Gln Asp Gln Arg Gln Trp Gln Arg Gln Arg
1               5               10              15

Gln Gln Arg Arg
        20

<210> SEQ ID NO 20
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 20

Asp Ala Glu Phe Arg His Asp Ser Gly Tyr Glu Val His His Gln Lys
1               5               10              15

Leu Val Phe Phe Ala Glu Asp Val Gly Ser Asn Lys Gly Ala Ile Ile
        20              25              30

Gly Leu Met Val Gly Gly Val Val
        35              40

<210> SEQ ID NO 21
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (24)..(24)
<223> OTHER INFORMATION: Xaa is the D-form of proline

<400> SEQUENCE: 21

Asp Ala Glu Phe Arg His Asp Ser Gly Tyr Glu Val His His Gln Lys
1               5               10              15

Leu Val Phe Phe Ala Glu Asp Xaa Gly Ser Asn Lys
        20              25
```

```
<210> SEQ ID NO 22
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (15)..(15)
<223> OTHER INFORMATION: Xaa is the D-form of proline

<400> SEQUENCE: 22

Tyr Glu Val His His Gln Lys Leu Val Phe Phe Ala Glu Asp Xaa Gly
1               5                   10                  15

Ser Asn Lys Gly Ala Ile Ile Gly Leu Met Val Gly Gly Val Val
            20                  25                  30

<210> SEQ ID NO 23
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12)..(12)
<223> OTHER INFORMATION: Xaa is the D-form of proline

<400> SEQUENCE: 23

His His Gln Lys Leu Val Phe Phe Ala Glu Asp Xaa Gly Ser Asn Lys
1               5                   10                  15

Gly Ala Ile Ile Gly Leu Met Val
            20

<210> SEQ ID NO 24
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa is the D-form of proline

<400> SEQUENCE: 24

Lys Leu Val Phe Phe Ala Glu Asp Xaa Gly Ser Asn Lys Gly Ala Ile
1               5                   10                  15

Ile Gly

<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is the D-form of proline

<400> SEQUENCE: 25

Phe Phe Ala Glu Asp Xaa Gly Ser Asn Lys Gly Ala
1               5                   10

<210> SEQ ID NO 26
<211> LENGTH: 5
```

-continued

```
<212> TYPE: PRT
<213> ORGANISM: Artificial Sequence
<220> FEATURE:
<223> OTHER INFORMATION: Synthetic Polypeptide

<400> SEQUENCE: 26

Lys Leu Val Phe Phe
1               5
```